(12) United States Patent
Zhong

(10) Patent No.: US 9,828,409 B2
(45) Date of Patent: Nov. 28, 2017

(54) BRIDGED-CYCLO-PROTIDES AS PRODRUGS OF THERAPEUTIC NUCLEOSIDES AND NUCLEOTIDES

(71) Applicant: Minghong Zhong, Altamont, NY (US)

(72) Inventor: Minghong Zhong, Altamont, NY (US)

( * ) Notice: Subject to any disclaimer, the term of this patent is extended or adjusted under 35 U.S.C. 154(b) by 15 days.

(21) Appl. No.: 14/658,194

(22) Filed: Mar. 15, 2015

(65) Prior Publication Data

US 2015/0266918 A1    Sep. 24, 2015

Related U.S. Application Data

(60) Provisional application No. 61/955,240, filed on Mar. 19, 2014.

(51) Int. Cl.
| | |
|---|---|
| *C07H 19/10* | (2006.01) |
| *C07H 19/11* | (2006.01) |
| *C07H 19/213* | (2006.01) |
| *C07H 19/04* | (2006.01) |
| *C07H 19/14* | (2006.01) |
| *C07H 19/12* | (2006.01) |
| *C07H 19/16* | (2006.01) |
| *C07H 19/06* | (2006.01) |
| *C07H 19/056* | (2006.01) |
| *C07H 19/20* | (2006.01) |
| *C07F 9/6561* | (2006.01) |
| *C07F 9/6584* | (2006.01) |
| *C07F 9/6574* | (2006.01) |
| *C07F 9/6571* | (2006.01) |
| *A61K 31/7068* | (2006.01) |
| *A61K 31/7072* | (2006.01) |
| *A61K 45/06* | (2006.01) |
| *A61K 31/708* | (2006.01) |
| *A61K 31/7076* | (2006.01) |
| *A61K 31/706* | (2006.01) |

(52) U.S. Cl.
CPC ........ *C07H 19/10* (2013.01); *A61K 31/706* (2013.01); *A61K 31/708* (2013.01); *A61K 31/7068* (2013.01); *A61K 31/7072* (2013.01); *A61K 31/7076* (2013.01); *A61K 45/06* (2013.01); *C07F 9/65616* (2013.01); *C07F 9/65744* (2013.01); *C07F 9/65842* (2013.01); *C07F 9/65844* (2013.01); *C07F 9/657154* (2013.01); *C07H 19/04* (2013.01); *C07H 19/056* (2013.01); *C07H 19/06* (2013.01); *C07H 19/11* (2013.01); *C07H 19/12* (2013.01); *C07H 19/14* (2013.01); *C07H 19/16* (2013.01); *C07H 19/20* (2013.01); *C07H 19/213* (2013.01)

(58) Field of Classification Search
CPC ...... C07H 19/10; C07H 19/11; C07H 19/213; C07H 19/04; C07H 19/14; C07H 19/12; C07H 19/16; C07H 19/06; C07H 19/056; C07H 19/20; C07F 9/65616; C07F 9/65844; C07F 9/65744; C07F 9/657154; C07F 9/65842; A61K 31/7068; A61K 31/7072; A61K 45/06; A61K 31/708; A61K 31/7076; A61K 31/706

See application file for complete search history.

(56) References Cited

U.S. PATENT DOCUMENTS

| | | | |
|---|---|---|---|
| 6,339,151 B1 * | 1/2002 | Shepard | A61K 47/48023 536/26.8 |
| 2014/0235566 A1 * | 8/2014 | Amblard | C07H 19/06 514/49 |

* cited by examiner

*Primary Examiner* — Jonathan S Lau

(57) ABSTRACT

Provided herein are bridged cyclic phosphates and phosphoramidates (bc-ProTides) of nucleosides, which is a compound, its stereoisomers, isotope-enriched analogs, pharmaceutically acceptable salts, hydrates, solvates, or crystalline or polymorphic forms thereof, with the following structure:

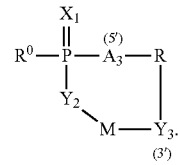

These compounds can be used for the treatment of viral infections and/or neoplastic diseases in mammals. By optimizing combinations of $Y_2$, $Y_3$, $R^o$, and M, the cleavability of these compounds as prodrugs can be attuned for different tissue targeting with various functional combinations. Also disclosed are processes and methods for preparation of these compounds.

6 Claims, No Drawings

BRIDGED-CYCLO-PROTIDES AS PRODRUGS OF THERAPEUTIC NUCLEOSIDES AND NUCLEOTIDES

CROSS REFERENCE TO RELATED APPLICATIONS

The present applications claims the benefits of U.S. Provisional Application Ser. No. 61/955,240, the entire said invention being incorporated herein by reference.

TECHNICAL FIELD OF THE INVENTION

The present invention relates to compounds, their preparation methods, and uses as medicinal agents in treatment of viral infections and/or neoplastic diseases. 3',5'-Bridged cyclic phosphates and phosphoramidates formed by a 5'-P, 3'-O-linker of tunable cleavability as prodrugs (bc-ProTides) for active nucleotides, usually nucleotide triphosphates, are provided which allow concentration of active drugs in diseased tissues such as infected hepatic tissues.

BACKGROUND OF THE INVENTION

Nucleoside analogues are highly effective agents for treatment of viral infectious diseases such as AIDS, hepatitis B, herpes virus, herpes zoster, cytomegalovirus and the like. A large number of significant known compounds include Entecavir, Abacavir, Lamivudine, Tenofovir, Adefovir, Acyclovir, Ganciclovir, Famciclovir, Lobucavir and the like. Nucleoside analogues, such as Gemcitabine, Cladribine (2-CdA), Fludarabine, Clofarabine, Nelarabine and the like, are effective for treatment of neoplastic diseases. It is expected that nucleoside analogues should also play a pivotal role in anti-HCV and anti-DENV treatment with one recently approved nucleotide (Sofosbuvir) of this kind and several nucleoside analogues in late stage clinical developments at the present time.

Most of anticancer and antiviral nucleoside analogs require metabolic activation to the 5'-mono, di-, and triphosphates via sequential phosphorylation by nucleoside and nucleotide kinases. Inefficient metabolic activation has been known to be among causes of the lack of therapeutic effectiveness of many nucleoside analogs, and as an important mechanism of nucleoside drug resistance. In these cases, usually the first phosphorylation step is rate limiting, thus the activity of these nucleosides can be rescued by various phosphate and phosphonate prodrug strategies. A variety of nucleoside monophosphate prodrugs (pronucleotides or ProTides), such as aryloxy phosphoramidate diesters, bisPOM, cycloSAL, hepDirect, and SATE, have been developed to improve their therapeutic activity by increasing the intracellular uptake of mono-phosphorylated nucleoside drugs. Prominent examples include Adefovir dipivoxil, Tenofovir disoproxil, and Sofosbuvir (GS-7977). However, existing ProTides have issues such as intracellular release of toxic agents (aryl alcohols, aryl vinyl ketone, ethylene sulfide, etc.), poor stability, varieties in intra- and interpatient pharmacokinetic and pharmacodynamic profiles, and low yields in synthesis. As an example, INX-189 produces intracellularly 1-naphthol, which, in addition to postulated mitochondrial toxicity of the resulting nucleotide, potentially caused the failure of this compound. As another example, Sofosbuvir, a clinical anti-HCV drug, is an aryloxy phosphoramidate diester and releases toxic phenol.

3',5'-Cyclic phosphates and phosphoramidates of nucleotides have been developed as uncommon prodrug structures to deliver nucleoside 5'-phosphates into cells with the expectation of improved cellular uptake by reducing the rotational degrees of freedom with a conformationally constrained structure and blocking the 3'-hydroxyl group to reduce polarity, and also removing toxic phenol or 1-naphthol. A variety of derived prodrug forms include phosphoramidate, SATE, pivaloyloxymethyl (POM), and simple alkyl ester groups as substituents of such 3',5'-cyclic phosphates and phosphoramidates. One notable example is PSI-352938, a suspended investigational drug for anti-HCV treatment because of the observed elevated level of liver enzymes in patients in clinical trials. It was reported that PSI-352938 was activated to nucleoside 5'-phosphates via a key step of selective ring opening by phosphodiester cleavage of the 3'-phosphate-oxygen bond catalyzed by cyclic nucleotide phosphodiesterase (PDE) enzymes. We believe this PDE-mediated hydrolytic activation be shared by all 3',5'-cyclic phosphate and phosphoramidate prodrugs, may impact the tightly regulated cellular cyclic nucleotide signaling pathways, which are temporally, spatially, and functionally compartmentalized, and result in abnormal intracellular concentrations of cyclic nucleotides (such as cAMP and cGMP), and, consequently, myriad biological responses leading to human diseases. These cyclic nucleotides may also act as secondary messengers and lead to undesired physiological changes, with their median effective concentrations ($EC_{50}$) in or close to the range of apparent activation constants ($K_a$) of protein kinase A (PKA RI$\beta_2$:$C_2$, 29 nm; RI$\alpha_2$:$C_2$, 101 nm; RII$\alpha_2$:$C_2$, 137 nm; and RII$\beta_2$:$C_2$, 584 nm) for cAMP and of protein kinase G (PKG-I$\alpha$, 67 nm and PKG-I$\beta$, 133 nm) for cGMP.

Therefore, there are needs for better pronucleotides. To minimize cytotoxicity, properties of tissue targeting (i.e. concentration of active drugs in liver tissues based on ProTide strategy), no release of cytotoxic metabolites, and clearance of disrupting nontargeted vital cellular/biological processes (off-target effects) by the prodrug and its intermediates are extremely attractive.

SUMMARY OF THE INVENTION

This invention provides novel compounds of nucleoside bridged cyclic phosphate and phosphoramidates with a cleavable linker/bridge for use as prodrugs in treatment of viral infections and/or anti-neoplastic diseases in mammals, which is a compound, its stereoisomers, isotope-enriched analogues, salts (acid or basic addition salts), hydrates, solvates, or crystalline forms thereof, represented by the following structure (Formula I):

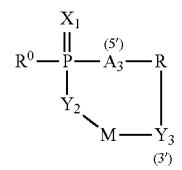

$R^0 = Y_4R^2, Y_1[C(R^{1a}R^{1b})]_dC(=X_2)Y_4R^2$ $M = CR^{5a}R^{5b}, (CR^{5a}R^{5b})_dOC(=O), (CR^{5a}R^{5b})_dC(=O)$ $d = 1$ to $4$ wherein (a) R is a moiety derivable by removal of 3'- and 5'-hydroxyl radicals from a therapeutic nucleoside or its equivalents, $CH_2$—R' wherein R' is a moiety derivable by removal of both a hydroxyl (OH) and a hydroxylmethyl (CH$_2$OH) radicals or both a hydroxyl and a phosphonate radical

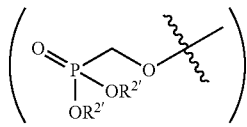

from a therapeutic nucleoside.

(b) A$_3$ is selected as follows: (i) A$_3$ is O, S, Se, or NR$^6$ where R$^6$ is H, OR$^{6'}$, alkyl, aryl, COR$^{6'}$, or CO$_2$R$^{6'}$, where R$^{6'}$ is H, alkyl, aryl, or heteroaryl; (ii) A$_3$CH$_2$ can be optionally replaced with CH$_2$A$_3$, or CF$_2$A$_3$, so as to represent a phosphonate or phosphonamidate;

(c) X$_1$ is O, S or Se;

(d) PR$^0$ is selected from: (i) phosphate, or phosphoramidate represented by PY$_4$R$^2$ where Y$_4$ is O, S, Se, or NR$^{8'''}$; (ii) phosphoramidate of amino acid esters or amides, or of esters or amides of modified amino acids, represented by PY$_1$[C(R$^{1a}$R$^{1b}$)]$_d$C(=X$_2$)Y$_4$R$^2$ where Y$_1$ is NR$^8$, X$_2$ is O, S or Se, and Y$_4$ is O, S, Se, or NR$^{8'''}$;

(e) M is a molecular bridge selected from CR$^{5a}$R$^{5b}$, (CR$^{5a}$R$^{5b}$)$_d$OC(=O), and (CR$^{5a}$R$^{5b}$)$_d$C(=O), where d is 1 to 4;

(f) Y$_1$, Y$_2$, Y$_3$, and Y$_4$ are selected as follows: (i) Y$_1$ is selected from O, S, Se, and NR$^8$; (ii) Y$_2$ is selected from O, S, Se, and NR$^{8'}$; (iii) Y$_3$ is selected from O, S, Se, and NR$^{8''}$; (iv) Y$_4$ is selected from O, S, Se, and NR$^{8'''}$; (v) R$^8$ and R$^{1a}$ or R$^{1b}$ together are (CH$_2$)$_n$ so as to form a cyclic ring that includes the adjoining N and C atoms, where n is 2 to 4, and Y$_1$ is NR$^8$; (vi) R$^{8'}$ and R$^{5a}$ or R$^{5b}$ together are (CH$_2$)$_n$ so as to form a cyclic ring that includes the adjoining N and C atoms, where n is 2 to 4 and Y$_2$ is NR$^{8'}$; (vii) R$^{8''}$ and R$^{5a}$ or R$^{5b}$ together are (CH$_2$)$_n$ so as to form a cyclic ring that includes the adjoining N and C atoms, where n is 2 to 4, and Y$_3$ is NR$^{8''}$; (viii) Y$_3$ is O, M is CR$^{5a}$R$^{5b}$C(=O), and Y$_2$ is NR$^{8'}$, so that Y$_2$CR$^{5a}$R$^{5b}$C(=O)Y$_3$ represents an ester of a natural or modified α-amino acid such as glycinyl (NHCH$_2$CO$_2$), or Y$_2$ is O or S; (ix) the said modified α-amino acids can be a β-, γ-, or δ-amino acid or its analogues represented by Y$_2$(CR$^{5a}$R$^{5b}$)$_d$C(=O)Y$_3$ where d is 2 to 4; (x) Y$_2$ can be O or S of an α-amino acid residue as in serine (OH), threonine (OH), and cysteine (SH), and the amino can be substituted or unsubstituted;

(g) R$^2$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, and substituted heteroaryl;

(h) R$^8$, R$^{8'}$, R$^{8''}$, and R$^{8'''}$ are independently selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; R$^8$, R$^{8'}$, R$^{8''}$, or R$^{8'''}$ in Y$_x$ can be the same or different groups where x is 1 to 4;

(i) R$^{1a}$ and R$^{1b}$ are selected as follows: (i) R$^{1a}$ and R$^{1b}$ are independently selected from hydrogen, C$_1$-C$_{10}$ alkyl, cycloalkyl, —(CH$_2$)$_c$NR$^{1'}{}_2$, hydroxy(C$_1$-C$_6$)alkyl, —CH$_2$SH, —(CH$_2$)$_2$S(=O)$_d$Me, —(CH$_2$)$_3$NHC(=NH)NH$_2$, (1H-indol-3-yl)methyl, (1H-imidazol-4-yl)methyl, —(CH$_2$)$_e$COR$^{1'''}$, aryl, heteroaryl, arylalkyl(C$_1$-C$_3$), and heteroarylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^{1'}$ is hydrogen or alkyl, which includes, but is not limited to, C$_1$-C$_{20}$ alkyl, and R$^{1'''}$ is —OR$^{1'}$ or —N(R$^{1'}$)$_2$; (ii) R$^{1a}$ is H and R$^{1b}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(=O)NH$_2$, CH$_2$CH$_2$COOH, CH$_2$CH$_2$C(=O)NH$_2$, CH$_2$CH$_2$CH$_2$CH$_2$NH$_2$, —CH$_2$CH$_2$CH$_2$NHC(=NH)NH$_2$, CH$_2$Ph, CH$_2$((4'-OH)-Ph), CH$_2$-imidazol-4-yl, or lower cycloalkyl; or (iii) R$^{1b}$ is H and R$^{1a}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(=O)NH$_2$, CH$_2$CH$_2$COOH, CH$_2$CH$_2$C(=O)NH$_2$, CH$_2$CH$_2$CH$_2$CH$_2$NH$_2$, —CH$_2$CH$_2$CH$_2$NHC(=NH)NH$_2$, CH$_2$Ph, CH$_2$((4'-OH)-Ph), CH$_2$-imidazol-4-yl, or lower cycloalkyl; (iv) R$^{1a}$ and R$^{1b}$ both are C$_1$-C$_6$ alkyl; (v) R$^{1a}$ and R$^{1b}$ together are (CH$_2$)$_m$ so as to form a spiro ring, where m is 2 to 5; (vi) R$^{1a}$ is hydrogen and R$^{1b}$ and R$^8$ together are (CH$_2$)$_n$ so as to form a cyclic ring that includes the adjoining N and C atoms, where n is 2 to 4 and Y$_1$ is NR$^8$; (vii) R$^{1b}$ is hydrogen and R$^{1a}$ and R$^8$ together are (CH$_2$)$_n$ so as to form a cyclic ring that includes the adjoining N and C atoms, where n is 2 to 4 and Y$_1$ is NR$^8$;

(j) R$^{5a}$ and R$^{5b}$ are selected as follows: (i) R$^{5a}$ and R$^{5b}$ are independently selected from hydrogen, C$_1$-C$_{10}$ alkyl, cycloalkyl, —(CH$_2$)$_c$(NR$^{1'}$)$_2$, hydroxyalkyl (C$_1$-C$_6$), —CH$_2$SH, —(CH$_2$)$_2$S(=O)$_d$Me, —(CH$_2$)$_3$NHC(=NH) NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^{1'}$ is independently hydrogen or C$_1$-C$_6$ alkyl and R$^{1'''}$ is —OR$^{1'}$ or —N(R$^{1'}$)$_2$; (ii) R$^{5a}$ and R$^{5b}$ both are C$_1$-C$_6$ alkyl; (iii) R$^{5a}$ and R$^{5b}$ together are (CH$_2$)$_m$ so as to form a spiro ring, where m is 2 to 5; (iv) R$^{5a}$ is hydrogen and R$^{5b}$ and R$^{8'}$ together are (CH$_2$)$_n$ so as to form a cyclic ring that includes the adjoining N and C atoms where Y$_2$ is NR$^{8'}$, and n is 2 to 4; (v) R$^{5b}$ is hydrogen and R$^{5a}$ and R$^{8'}$ together are (CH$_2$)$_n$ so as to form a cyclic ring that includes the adjoining N and C atoms, where Y$_2$ is NR$^{8'}$, and n is 2 to 4; (vi) R$^{5a}$ is hydrogen and R$^{5b}$ and R$^{8''}$ together are (CH$_2$)$_n$ so as to form a cyclic ring that includes the adjoining N and C atoms where Y$_3$ is NR$^{8''}$, and n is 2 to 4; (vii) R$^{5b}$ is hydrogen and R$^{5a}$ and R$^{8''}$ together are (CH$_2$)$_n$ so as to form a cyclic ring that includes the adjoining N and C atoms, where Y$_3$ is NR$^{8''}$, and n is 2 to 4;

Provided herein are compounds, comprising 3',5'-bridged cyclic phosphates or phosphoramidates. The molecular bridge (M) can be selected from acetal, ketal, thioacetal, thioketal, oxymethylamide, and N-Mannich base of a general structure (Y$_2$—C(R$^{5a}$R$^{5b}$)-3'-Y$_3$), or be a lactone (Y$_2$—C(R$^{5a}$R$^{5b}$)C(=O)-3'-O) or a carbonate ester (Y$_2$—C(R$^{5a}$R$^{5b}$)OC(=O)-3'-O). The other substituent on the phosphorus center can be an alkoxyl, a thioalkoxyl, a cycloalkyloxyl, a heterocyclyloxyl, an aryloxyl, a heteroaryloxyl, an alkylamino, a cycloalkylamino, a heterocyclylamino, an arylamino, a heteroarylamino, or a natural amino acid or modified amino acid so as to form a phosphoramidate or a phosphate ester. The oxo- of this phosphate or phosphoramidate group can be substituted by sulfur and selenium. Embodiments of these groups are described in detail herein.

Each of the compounds further comprises a structure moiety effective against viral infections or for treatment of neoplastic diseases, which is a nucleoside with 3'-$Y_3$H and 5'-$A_3$H, or 5'-phosphonate or 5'-phosophonamidate. It is believed that these compounds can be transformed into nucleotide monophosphate by enzyme mediated processes or spontaneous hydrolysis (Activation mechanism in FIGURE 1 as an example). With appropriate substituents, these masked drugs can selectively concentrate in diseased tissues such as infected liver tissue, and be activated on site by tissue specific enzymes. Thus, potentially undesired distribution of the active drugs, and thus their toxicity in tissues such as gastrointestinal tract can be reduced.

In certain embodiments, compounds provided herein may be selectively concentrated to liver tissues, lymphatic tissues, or other targeted tissues after oral administration, and metabolized to nucleotide monophosphates, which are further phosphorylated by cellular kinases to the active nucleotide phosphates. These phosphates can inhibit the targeted enzymes. Thus optimal dose amounts can be reduced.

In certain embodiments, the structure moiety of antiviral or anti-neoplastic agent is a therapeutic nucleoside or potent nucleoside recognized by persons skilled in the art for the treatments of such conditions. The two moieties are bonded to form an 8-membered ring fused with sugar via a linker ($Y_2$—C($R_5R_6$)-3'-$Y_3$) or to form a 9 to 12-membered ring fused with sugar via a linker ($Y_2$—(C($R_5R_6$))$_d$C(=O)-3'-$Y_3$) or ($Y_2$—C($R_5R_6$) OC(=O)-3'-$Y_3$), or the like, where $Y_2$ and $Y_3$ is independently O, S, or $NR^{8''}$, and d is 1 to 4.

FIG. 1

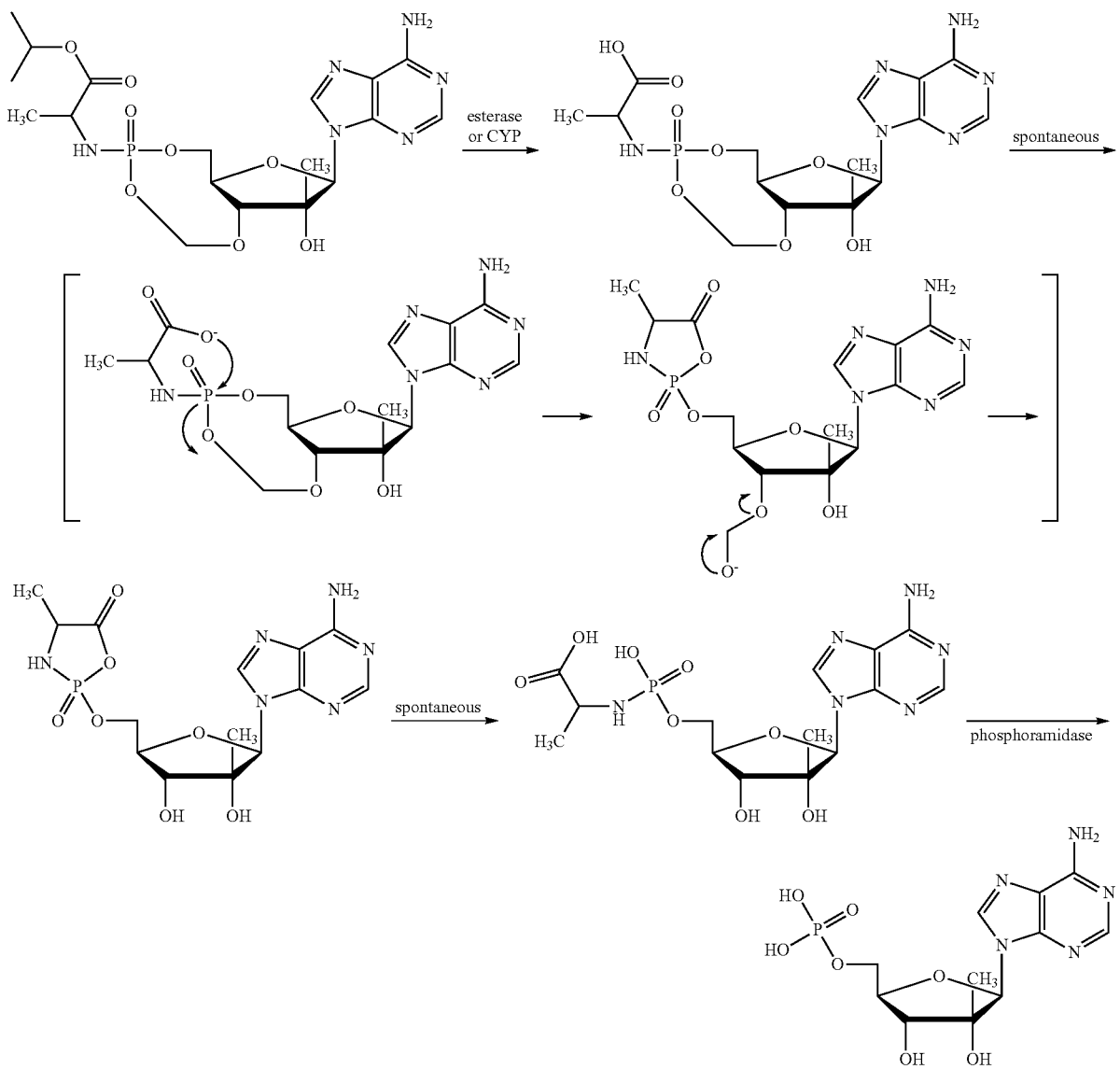

DETAILED DESCRIPTION OF THE INVENTION

This invention pertains to novel bridged cyclic phosphate and phosphoramidate compounds, their compositions, methods of preparations, and use in the treatments of viral infections and neoplastic diseases in humans and animals.

Definition

The definitions of terms used herein are consistent to those known to those of ordinary skill in the art, and in case of any differences the definitions are used as specified herein instead.

The term "alkyl", as used herein refers to a monovalent saturated straight or branched hydrocarbon radical, including both unsubstituted and substituted alkyl groups. In certain embodiments, the alkyl group includes one to twenty carbon atoms, i.e., $C_1$-$C_{20}$ alkyl, more preferably $C_1$-$C_{10}$ alkyl. In certain embodiments, the alkyl group is a primary, secondary, or tertiary hydrocarbon radical. In certain embodiments, the alkyl group is a halogenated alkyl group. In certain embodiments, the alkyl group is selected from the group consisting of methyl, $CF_3$, $CF_2Cl$, $CFCl_2$, $CCl_3$, ethyl, $CH_2CF_3$, $CF_2CF_3$, propyl, isopropyl, butyl, isobutyl, sec-butyl, tert-butyl, pentyl, isopentyl, neopentyl, hexyl, isohexyl, neohexyl, 3-methylpentyl, 2,2-dimethylbutyl, 2,3-dimethylbutyl, heptyl, octyl, isooctyl, nonyl, decyl, and dodecyl. Non-limiting examples of optional substituents are selected from the group consisting of hydroxyl, amino, halogen (fluoro, chloro, bromo or iodo), alkylamino, arylamino, alkoxy, aryloxy, nitro, cyano, sulfonic acid, sulfate, phosphonic acid, phosphate, or phosphonate, either unprotected, or protected as necessary, as known to those skilled in the art.

The term "cycloalkyl", as used herein refers to a saturated cyclic hydrocarbon radical. In certain embodiments, the cycloalkyl group may be bridged, and/or a fused bicyclic group. In certain embodiments, the cycloalkyl group includes three to ten carbon atoms, i.e., $C_3$-$C_{10}$ cycloalkyl. Non-limiting examples are selected from the group consisting of cyclopropyl, cyclobutyl, cyclopentyl, cyclohexyl, cycloheptyl, bicyclo[2.1.1]hexyl, bicyclo[3.1.0]hexyl, bicyclo[2.2.1]heptyl, decalinyl, or adamantyl.

The term "cycloalkylalkyl", as used herein refers to an acyclic alkyl group substituted by a cycloalkyl comprising of three to eight carbon atoms. Non-limiting examples are selected from the group consisting of cyclopropylmethyl, 2-cyclopropylethyl, 3-cyclopropylpropyl, cyclobutylmethyl, cyclopentylmethyl, cyclohexylmethyl.

"Alkenyl" refers to straight, branched, acyclic monovalent olefinically unsaturated hydrocarbon groups, having up to about 20 carbon atoms, preferably $C_2$-$C_6$, having at least one C=C bond. The term includes both substituted and unsubstituted moieties. Non-limiting examples are selected from the group consisting of vinyl (—CH=$CH_2$), n-propenyl (—$CH_2$CH=$CH_2$), isopropenyl (—C($CH_3$)=$CH_2$), butenyl, pentenyl, hexenyl, and the like.

The term "cycloalkenyl", as used herein refers to monovalent cyclic hydrocarbon groups, having at least one C=C bond. In certain embodiments, cycloalkenyl refers to mono- or multicyclic ring systems that include at least one C=C bond. In certain embodiments, the cycloalkenyl group may be a bridged, non-bridged, and/or a fused bicyclic group. In certain embodiments, the cycloalkenyl group includes three to ten carbon atoms, i.e., $C_3$-$C_{10}$ cycloalkenyl.

"Alkynyl" refers to monovalent unsaturated hydrocarbon groups having at least one C≡C bond. In certain embodiments, alkynyl refers to hydrocarbon radicals having up to about 20 carbon atoms which can be straight-chained, branched, or cyclic, and having at least one C≡C bond. Non-limiting examples of alkynyl groups include ethynyl (—C≡CH), propargyl (—$CH_2$C≡CH), and the like.

The term "aryl", as used herein, and unless otherwise specified, refers to a monovalent unsaturated aromatic carbocyclic group such as phenyl, naphthyl, biphenyl, and the like. The aryl can be substituted or unsubstituted. An aryl group can be substituted with one or more moieties selected from the group consisting of halogen (fluoro, chloro, bromo or iodo), alkyl, haloalkyl, hydroxyl, amino, alkylamino, arylamino, acyl, acyloxy, carboxyl, alkoxy, aryloxy, nitro, cyano, sulfonic acid, sulfate, phosphonic acid, phosphate, phosphonate, thiol, thioalkoxy, or other moieties as known to those skilled in the art.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(=O)—OR' where OR' is alkoxy as defined herein.

"Amino" refers to the radical —$NH_2$. The term "alkylamino" or "arylamino" refers to an amino group that has one or two alkyl or aryl substituents, respectively. In certain embodiments, the alkyl substituent is lower alkyl. In certain embodiments, the alkyl or lower alkyl is substituted or unsubstituted. "Monoalkylamino" refers to the group —NR'H, wherein R' is selected from alkyl, cycloalkyl, and aryl.

"Carboxyl" or "carboxy" refers to the radical —C(=O)OH.

"Thioalkoxy" refers to the group —SR' where R' is alkyl or cycloalkyl.

The term "heterocyclyl" refers to a monovalent radical of monocyclic non-aromatic ring group and/or multicyclic ring group that contains at least one non-aromatic ring, wherein one or more of the non-aromatic ring atoms are heteroatoms independently selected from O, S, N or P, and the remaining ring atoms are carbon atoms. The heterocyclyl groups are bonded to the rest of the molecule through the non-aromatic ring, and may be attached to the main structure at any heteroatom or carbon atom which results in the creation of a stable compound, and heterocyclic may also be optionally substituted. The heteroatoms (nitrogen, phosphorus, or sulfur) in a heterocyclyl group may be optionally oxidized, the nitrogen atoms may be optionally quaternized, and some rings may be partially or fully saturated, or aromatic. In certain embodiments, the heterocyclyl or heterocyclic group has 3 to 20 ring atoms. In certain embodiments, the heterocyclyl may be monocyclic, bicyclic, tricyclic, or tetracyclic, which may include bridged rings or fused rings.

The term "heteroaryl" or "hetaryl" refers to a monovalent monocyclic and/or multicyclic aromatic group that contain at least one aromatic ring, wherein at least one aromatic ring contains one or more heteroatoms independently selected from O, S, N, and P in the ring, and which is bonded to the rest of the molecule through the aromatic ring, and may also be optionally substituted. Each ring of a heteroaryl group can contain one or two O atoms, one or two S atoms, one to four N atoms, and/or one to four P atoms, provided that the total number of heteroatoms in each ring is four or less and each ring contains at least one carbon atom. In certain embodiments, the heteroaryl has 5 to 20 ring atoms.

The term "alkylaryl" refers to an aryl group with an alkyl substituent. The term "arylalkyl" includes an alkyl group with an aryl substituent.

The term "alkylheterocyclyl" refers to a heterocyclyl group with an alkyl substituent. The term "heterocyclylalkyl" includes an alkyl group with a heterocyclyl substituent.

The term "alkylheteroaryl" refers to a heteroaryl group with an alkyl substituent. The term alkylheteroaryl includes an alkyl group with a heteroaryl substituent.

The term "acyl group", "alkanoyl group", or "aroyl group" as used herein refers to a chemical entity comprising the general formula R—C(=O)— where R represents any aliphatic, alicyclic, or aromatic group and C(=O) represents a carbonyl group.

The term "acylation" as used herein refers to any process whereby an acid, or an acid derivative such as an acid halide or an acid anhydride is used to convert a hydroxyl group into an ester, or an amine into an amide.

"Halogen" or "halo" refers to fluoro, chloro, bromo or iodo; and the term "halide" refers to fluoride, chloride, bromide and iodide.

The term of "phosphoramidate" as used herein refers to a phosphate that has an $NR_2$ instead of an OH or OR group where R represents any aliphatic, alicyclic, or aromatic group. In case of "phosphorodiamidate" two OHs or ORs are replaced with $NR_2$.

The terms of "phosphates" and "phosphate ester" as used herein refer to esters of phosphoric acid.

"Phosphonates" and "phosphonate esters" as used herein refer to esters of phosphonic acids containing C—P(=O)(OR)$_2$ groups where R is alkyl, aryl and the like.

The term of "phosphonamidate" as used herein refers to a phosphonate that has an $NR_2$ instead of an OH or OR group where R represents any aliphatic, alicyclic, or aromatic group. In case of "phosphonodiamidate" two OHs or ORs are replaced with $NR_2$.

The term "nucleoside" as used herein refers to a molecule composed of a heterocyclic nitrogenous base, particularly a purine or pyrimidine, containing an N-glycosidic linkage with a sugar, particularly a pentose. Nucleosides include both L- and D-nucleoside enantiomers.

The term "nucleoside analogue" as used herein refers to a non-natural nucleoside, a "nucleoside" derivative, a "carbocyclic nucleoside", a "C-nucleoside", or an "acyclic nucleoside".

The term "carbocyclic nucleoside" as used herein refers to a nucleoside or nucleoside analog containing a sugar-like moiety with 4'-oxo displaced by methylene or substituted methylene or methine such as cyclopentanes, cyclobutanes and the like, which are not N-glycosides and include phosphorylation site(s) or phosphate, or phosphonate, or their precursors.

The term "C-nucleoside" as used herein refers to nucleosides in which the ribofuranosyl moiety is linked to a heterocyclic base through a carbon-to-carbon bond instead of the traditional carbon-to-nitrogen bond.

The term "acyclic nucleoside" as used herein refers to a nucleoside or nucleoside analog containing an alkyl as a sugar-like moiety, which includes phosphorylation site(s) or phosphate, or phosphonate, or their precursors. Examples related to this invention include, but not limiting to, ganciclovir, famciclovir, and cidofovir.

The term "pronucleotides" or "ProTides" as used herein refers to phosphorylated nucleoside analogues in which the phosphate moiety has been masked by various chemical entities to increase hydrophobicity, bypass first phosphorylation, and to allow targeted delivery to diseased tissues and selective inhibition of viral enzymes.

The term "nucleophile" as used herein refers to an electron-rich reagent that is an electron pair donor (contains an unshared pair of electrons) and forms a new bond to a carbon atom. Nucleophiles can be anions or neutrally charged. Examples include, but are not limited to, carbanions, oxygen anions, halide anions, sulfur anions, nitrogen anions, nitrogen bases, alcohols, ammonia, water, and thiols.

The term "leaving group" as used herein refers to a weakly basic chemical entity that is readily released from carbon, and takes the pair of bonding electrons binding it with said carbon atom. Leaving groups are chemical functional groups that can be displaced from carbon atoms by nucleophilic substitution. Examples include, but are not limited to, alkylsulfonates, substituted alkylsulfonates, arylsulfonates, substituted arylsulfonates, heterocyclicsulfonates, trichloroacetimidate, alkoxide, and aryloxide groups. Preferred leaving groups include, but are not limited to, chloride, bromide, iodide, p-nitrobenzenesulfonate (nosylate), p-(2,4-dinitroanilino)benzenesulfonate, benzenesulfonate, methylsulfonate (mesylate), p-methylbenzenesulfonate (tosylate), p-bromobenzenesulfonate (brosylate), trifluoromethylsulfonate (triflate), 2,2,2-trifluoroethanesulfonate, imidazolesulfonate, trichloroacetimidate, trifluoroacetate and other acylates, alkoxide, and aryloxide, i.e., 4-nitrophenoxide, pentafluorophenoxide, and 2,4,6-trichlorophenoxide.

The synonymous terms "hydroxyl protecting group" and "alcohol-protecting group" as used herein refer to substituents attached to the oxygen of an alcohol group commonly employed to block or protect the alcohol functionality while reacting other functional groups on the compound. Examples of such alcohol-protecting groups include the 2-tetrahydropyranyl group, 2-(bisacetoxyethoxy)methyl group, trityl group, trichloroacetyl group, carbonate-type blocking groups such as benzyloxycarbonyl (Cbz), trialkylsilyl groups, examples of such being trimethylsilyl, tert-butyldimethylsilyl, tert-butyldiphenylsilyl, phenyldimethylsilyl, triiospropylsilyl and thexyldimethylsilyl, ester groups such as formyl, ($C_1$-$C_{10}$) alkanoyl (optionally mono-, di- or tri-enriched with ($C_1$-$C_6$) alkyl, ($C_1$-$C_6$) alkoxy, halo, aryl, aryloxy or haloaryloxy), and the like, the aroyl group (including optionally mono-, di- or tri-enriched on the ring carbons with halo, ($C_1$-$C_6$) alkyl, ($C_1$-$C_6$) alkoxy wherein aryl is phenyl, 2-furyl, and the like), carbonates, sulfonates, and ethers such as benzyl, p-methoxybenzyl, methoxymethyl, 2-ethoxyethyl, benzyloxymethyl (BOM) group, and etc. The choice of alcohol-protecting group employed is not critical so long as the derivatized alcohol group is stable to the conditions of subsequent reaction(s) on other positions of the compound of the formula and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and G. M. Wuts, T. W. Greene, "Protective Groups in Organic Synthesis", John Wiley & Sons Inc., Hoboken, N.J., 2007, which are hereby incorporated by reference. The related terms "protected hydroxyl" or "protected alcohol" define a hydroxyl group substituted with a hydroxyl protecting group as discussed above.

The term "nitrogen protecting group," as used herein, refers to groups known in the art that are readily introduced on to and removed from a nitrogen atom. Examples of nitrogen protecting groups include acetyl (Ac), trifluoroacetyl, benzoyl (Bz), Boc, Cbz, trityl, DMTr, and benzyl (Bn). See also G. M. Wuts, T. W. Greene, "Protective Groups in Organic Synthesis", John Wiley & Sons Inc., Hoboken, N.J., 2007, and related publications.

The term "purine" or "pyrimidine" base refers to, but is not limited to, adenine, $N^6$-alkyl adenines, $N^6$-cycloalkyl adenines, $N^6$-acyl adenines (wherein acyl is C(=O)(alkyl, aryl, alkylaryl, or arylalkyl), 6-alkylaminopurine, 6-halopurine, 6-vinylpurine, 6-acetylenic purine, 6-acyl purine, 6-alkoxyl purine, 6-aryloxyl purine, 6-alkylthio purine, 2-akylaminopurines, 2-akylamino-6-oxopurine, 2-akylamino-6-thiopurines, 2-heteroaryl purine, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, 5-alkylpyrimidines, 5-benzylpyrimidines, 5-halopyrimidines, 5-vinylpyrimidine, 5-acetylenic pyrimidine, 5-acyl pyrimidine, 5-hydroxyalkyl pyrimidine, 5-amidopyrimidine, 5-cyanopyrimidine, 5-iodopyrimidine, 6-iodo-pyrimidine, 5-bromovinyl pyrimidine, 6-bromovinyl pyrimidine, 5-nitropyrimidine, 5-aminopyrimidine, 5-azacytidinyl, 5-azauracilyl, triazolopyridinyl, imidazolopyridinyl, furanopyrimidinyl, pyrrolopyrimidinyl, pyrazolopyrimidinyl, and triazolopyrimidinyl. Purine bases further include, but are not limited to, guanine, hypoxanthine, 7-deazaguanine, 7-deazaadenine, 4-aza-7,9-dideazaadenine, 2,6-diaminopurine, 6-amino-2-fluoropurine, 6-amino-2-chloropurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, dimethylformamidine group, and acyl groups such as acetyl, benzoyl, isobutyryl and propionyl, methanesulfonyl, and p-toluenesulfonyl.

The term "amino acid" refers to naturally occurring and synthetic α-, β-, γ-, or δ-amino acids, and includes but is not limited to, natural amino acids, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the D- or L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The compounds of this invention can contain one or more asymmetric carbon or phosphorus atoms (chiral centers), so that the compounds can exist in different stereoisomeric forms such as racemic mixtures, diastereomeric mixtures, optically active non-racemic mixtures, or single enantiomers. The single enantiomers, i.e., in optically pure forms, can be obtained by asymmetric synthesis or by resolution of racemic mixtures by conventional methods well-known to those skilled in the art.

The term of "Solvate" refers to a compound provided herein or a salt thereof that further includes a stoichiometric or non-stoichiometric amount of solvent bound by non-covalent intermolecular forces. The solvate is a hydrate, where the solvent is water.

The term of "Isotopically enriched" refers to a compound containing at least one atom having an isotopic composition other than the natural isotopic composition of that atom. The term of "Isotopic composition" refers to the amount of each isotope present for a given atom, and "natural isotopic composition" refers to the naturally occurring isotopic composition or abundance for a given atom. As used herein, an isotopically enriched compound optionally contains deuterium, carbon-13, nitrogen-15, and/or oxygen-18 at amounts other than their natural isotopic compositions.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent known to be useful for, or which has been or is currently being used for the treatment or prevention of a disorder or one or more symptoms thereof.

The term of "Pharmaceutically acceptable salt" refers to any nontoxic salt of a compound provided herein which retains the biological properties of the compound and has no undesirable properties for pharmaceutical use. Such salts may be derived from a variety of organic and inorganic counter-ions well known in the art, and include, but are not limited to: (1) acid addition salts formed when the compound contains one or more basic functionalities such as amine, purine, and pyrimidine, with organic or inorganic acids; or (2) salts formed when an acidic proton present in the parent compound such as carboxylic acid, phosphoric acid, and phosphonic acid, is either replaced by a metal ion, such as sodium, potassium, and ammonium, or coordinated with an organic base, such as aliphatic, alicyclic, or aromatic organic amines. It should be understood that all references to pharmaceutically acceptable salts include solvent addition forms (solvates) or crystal forms (polymorphs) as defined herein, of the same acid addition salt.

Compounds

An aspect of the invention is directed to a compound, its isotope-enriched analogues, its salts, hydrates, solvates, crystalline forms, and the like represented by formula I:

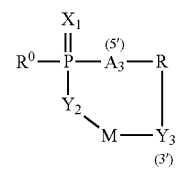

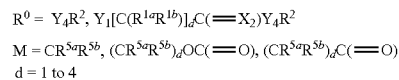

wherein (a) R is a moiety derivable by removal of 3'- and 5'-hydroxyl radicals from a therapeutic nucleoside or its equivalents, $CH_2$—R' wherein R' is a moiety derivable by removal of both a hydroxyl (OH) and a hydroxylmethyl ($CH_2OH$) radicals or both a hydroxyl and a phosphonate radical

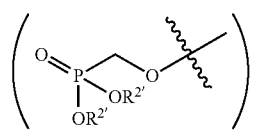

from a therapeutic nucleoside.

(b) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to represent a phosphonate or phosphonamidate;

(c) $X_1$ is O, S or Se;

(d) $PR^0$ is selected as follows: (i) phosphate, or phosphoramidate represented by $PY_4R^2$ where $Y_4$ is O, S, Se, or $NR^{8'''}$; (ii) phosphoramidate of amino acid esters or amides, or of esters or amides of modified amino acids, represented by $PY_1[C(R^{1a}R^{1b})]_dC(=X_2)Y_4R^2$ where $Y_1$ is $NR^8$, $X_2$ is O, S or Se, and $Y_4$ is O, S, Se, or $NR^{8'''}$;

(e) M is a molecular bridge selected from $CR^{5a}R^{5b}$, $(CR^{5a}R^{5b})_dOC(=O)$, and $(CR^{5a}R^{5b})_dC(=O)$, where d is 1 to 4;

(f) $Y_1$, $Y_2$, $Y_3$, and $Y_4$ are selected as follows: (i) $Y_1$ is selected from O, S, Se, and $NR^8$; (ii) $Y_2$ is selected from O, S, Se, and $NR^{8'}$; (iii) $Y_3$ is selected from O, S, Se, and $NR^{8''}$; (iv) $Y_4$ is selected from O, S, Se, and $NR^{8'''}$; (v) $R^8$ and $R^{1a}$ or $R^{1b}$ together are $(CH_2)_n$ so as to form a cyclic ring that includes the adjoining N and C atoms, where n is 2 to 4, and $Y_1$ is $NR^8$; (vi) $R^{8'}$ and $R^{5a}$ or $R^{5b}$ together are $(CH_2)_n$ so as to form a cyclic ring that includes the adjoining N and C atoms, where n is 2 to 4 and $Y_2$ is $NR^{8'}$; (vii) $R^{8''}$ and $R^{5a}$ or $R^{5b}$ together are $(CH_2)_n$ so as to form a cyclic ring that includes the adjoining N and C atoms, where n is 2 to 4, and $Y_3$ is $NR^{8''}$; (viii) $Y_3$ is O, and $Y_2$ is $NR^{8'}$, so that $Y_2CR^{5a}R^{5b}C(=O)Y_3$ represents an ester of a natural or modified α-amino acid such as glycinyl ($NHCH_2CO_2$), or $Y_2$ is O or S; (ix) the said modified α-amino acids can be a β-, γ-, or δ-amino acid or its analogues represented by $Y_2(CR^{5a}R^{5b})_dC(=O)Y_3$ where d is 2 to 4; (x) $Y_2$ can be O or S of an α-amino acid residue as in serine (OH), threonine (OH), and cysteine (SH), and the amino can be substituted or unsubstituted;

(g) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(h) $R^8$, $R^{8'}$, $R^{8''}$, and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$, $R^{8'}$, $R^{8''}$, or $R^{8'''}$ in $Y_x$ can be the same or different groups where x is 1 to 4;

(i) $R^{1a}$ and $R^{1b}$ are selected as follows: (i) $R^{1a}$ and $R^{1b}$ are independently selected from hydrogen, $C_1$-$C_{10}$ alkyl, cycloalkyl, $-(CH_2)_cNR^{1'}_2$, hydroxy($C_1$-$C_6$)alkyl, $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl, heteroaryl, arylalkyl($C_1$-$C_3$), and heteroarylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1'''}$ is $-OR^{1'}$ or $-N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4 and $Y_1$ is $NR^8$; (vii) $R^{1b}$ is hydrogen and $R^{1a}$ and $R^8$ together are $(CH_2)_n$ so as to form a cyclic ring that includes the adjoining N and C atoms, where n is 2 to 4 and $Y_1$ is $NR^8$;

(j) $R^{5a}$ and $R^{5b}$ are selected as follows: (i) $R^{5a}$, $R^{5b}$ are independently selected from hydrogen, $C_1$-$C_{10}$ alkyl, cycloalkyl, $-(CH_2)_c(NR^{1'})_2$, hydroxyalkyl ($C_1$-$C_6$), $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is $-OR^{1'}$ or $-N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where $Y_2$ is $NR^{8'}$, and n is 2 to 4; (v) $R^{5b}$ is hydrogen and $R^{5a}$ and $R^{8'}$ together are $(CH_2)_n$ so as to form a cyclic ring that includes the adjoining N and C atoms, where $Y_2$ is $NR^{8'}$, and n is 2 to 4; (vi) $R^{5a}$ is hydrogen and $R^{5b}$ and $R^{8''}$ together are $(CH_2)_n$ so as to form a cyclic ring that includes the adjoining N and C atoms where $Y_3$ is $NR^{8''}$, and n is 2 to 4; (vii) $R^{5b}$ is hydrogen and $R^{5a}$ and $R^{8''}$ together are $(CH_2)_n$ so as to form a cyclic ring that includes the adjoining N and C atoms, where $Y_3$ is $NR^{8''}$, and n is 2 to 4;

(k) The $Y_2$-M-$Y_3$ linker is represented as $Y_2-(CR^{5a}R^{5b})$-3'-$Y_3$, where $Y_3$ is O, S, or $NR^{8''}$, forming a 8-membered ring fused with pentose sugar at 3' and 5'-P or equivalent positions in acyclic and carbocyclic nucleoside analogues, or $Y_2-(CR^{5a}R^{5b})_dC(=O)$-3'-$Y_3$, or $Y_2-(CR^{5a}R^{5b})_dOC(=O)-Y-Y_3$, or the like, and d is 1 to 4, forming a 9 to 12-membered ring.

As can be appreciated from the structure represented by formula I above, there are myriad ways to express the several embodiments and aspects of each embodiment of the present invention. As seen below, the inventors have disclosed certain embodiments directed to the compound of formula I, each having several aspects, based on the identity of molecular bridges. This is not intended to be an explicit or implicit admission that these embodiments are independent or distinct nor should it be interpreted as such. Rather, it is intended to convey information so that the full breadth of the present invention can be understood. Furthermore, the following embodiments, and aspects thereof, are not meant to be limiting on the full breadth of the invention as recited by the structure of formula I.

A first embodiment of the invention is directed to a compound represented by formula I-1:

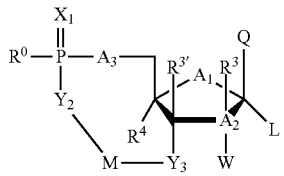

I-1 wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, aryl, and heteroaryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to represent a phosphonate or phosphonamidate;

(g) L and $R^4$ are independently selected from H, a lower alkyl, CN, vinyl, O-(lower alkyl), hydroxyl lower alkyl (i.e., $-(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $PR^0$ is selected as follows: (i) phosphate, or phosphoramidate represented by $PY_4R^2$ where $Y_4$ is O, S, Se, or $NR^{8'''}$; (ii) phosphoramidate of amino acid esters or amides, or of esters or amides of modified amino acids, represented by $PY_1[C(R^{1a}R^{1b})]_dC(=X_2)Y_4R^2$ where $Y_1$ is $NR^8$, $X_2$ is O, S or Se, and $Y_4$ is O, S, Se, or $NR^{8'''}$;

(i) $X_1$ is O, S or Se;

(j) M is a molecular bridge selected from $CR^{5a}R^{5b}$, $(CR^{5a}R^{5b})_dOC(=O)$, and $(CR^{5a}R^{5b})_dC(=O)$, where d is 1 to 4;

(k) $Y_1$, $Y_2$, $Y_3$, and $Y_4$ are selected as follows: (i) $Y_1$ is selected from O, S, Se, and $NR^8$; (ii) $Y_2$ is selected from O, S, Se, and $NR^8$; (iii) $Y_3$ is selected from O, S, Se, and $NR^{8''}$; (iv) $Y_4$ is selected from O, S, Se, and $NR^{8'''}$; (v) $R^8$ and $R^{1a}$ or $R^{1b}$ together are $(CH_2)_n$ so as to form a cyclic ring that includes the adjoining N and C atoms, where n is 2 to 4, and $Y_1$ is $NR^8$; (vi) $R^{8'}$ and $R^{5a}$ or $R^{5b}$ together are $(CH_2)_n$ so as to form a cyclic ring that includes the adjoining N and C atoms, where n is 2 to 4 and $Y_2$ is $NR^{8'}$; (vii) $R^{8''}$ and $R^{5a}$ or $R^{5b}$ together are $(CH_2)_n$ so as to form a cyclic ring that includes the adjoining N and C atoms, where n is 2 to 4, and $Y_3$ is $NR^{8''}$; (viii) $Y_3$ is O, and $Y_2$ is $NR^{8'}$, so that $Y_2CR^{5a}R^{5b}C(=O)Y_3$ represents an ester of a natural or modified α-amino acid such as glycinyl ($NHCH_2CO_2$), or $Y_2$ is O or S; (ix) the said modified α-amino acids can be a β-, γ-, or δ-amino acid or its analogues represented by $Y_2(CR^{5a}R^{5b})_dC(=O)Y_3$ where d is 2 to 4; (x) $Y_2$ can be O or S of an α-amino acid residue as in serine (OH), threonine (OH), and cysteine (SH), and the amino can be substituted or unsubstituted;

(l) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(m) $R^8$, $R^{8'}$, $R^{8''}$, and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$, $R^{8'}$, $R^{8''}$, or $R^{8'''}$ in $Y_x$ can be the same or different groups where x is 1 to 4;

(n) $R^{1a}$ and $R^{1b}$ are selected as follows: (i) $R^{1a}$ and $R^{1b}$ are independently selected from hydrogen, $C_1$-$C_{10}$ alkyl, cycloalkyl, $-(CH_2)_cNR^{1'}_2$, hydroxy($C_1$-$C_6$)alkyl, $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_cCOR^{1'''}$, aryl, heteroaryl, arylalkyl($C_1$-$C_3$), and heteroarylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^1$ is independently hydrogen or alkyl, which includes, but is not limited to, $C_1$-$C_{20}$ alkyl, and $R^{1'''}$ is $-OR^{1'}$ or $-N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4 and $Y_1$ is $NR^8$; (vii) $R^{1b}$ is hydrogen and $R^{1a}$ and $R^8$ together are $(CH_2)_n$ so as to form a cyclic ring that includes the adjoining N and C atoms, where n is 2 to 4 and $Y_1$ is $NR^8$;

(o) $R^{5a}$ and $R^{5b}$ are selected as follows: (i) $R^{5a}$, $R^{5b}$ are independently selected from hydrogen, $C_1$-$C_{10}$ alkyl, cycloalkyl, $-(CH_2)_c(NR^{1'})_2$, hydroxyalkyl $(C_1$-$C_6)$, $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is $-OR^{1'}$ or $-N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where $Y_2$ is $NR^{8'}$, and n is 2 to 4; (v) $R^{5b}$ is hydrogen and $R^{5a}$ and $R^{8'}$ together are $(CH_2)_n$ so as to form a cyclic ring that includes the adjoining N and C atoms, where $Y_2$ is $NR^{8'}$, and n is 2 to 4; (vi) $R^{5a}$ is hydrogen and $R^{5b}$ and $R^{8''}$ together are $(CH_2)_n$ so as to form a cyclic ring that includes the adjoining N and C atoms where $Y_3$ is $NR^{8'}$, and n is 2 to 4; (vii) $R^{5b}$ is hydrogen and $R^{5a}$ and $R^{8''}$ together are $(CH_2)_n$ so as to form a cyclic ring that includes the adjoining N and C atoms, where $Y_3$ is $NR^{8''}$, and n is 2 to 4;

(p) Q is any nucleic acid base and analogues, either a naturally occurring or modified purine or pyrimidine base represented by, but not limited to, the following structures:

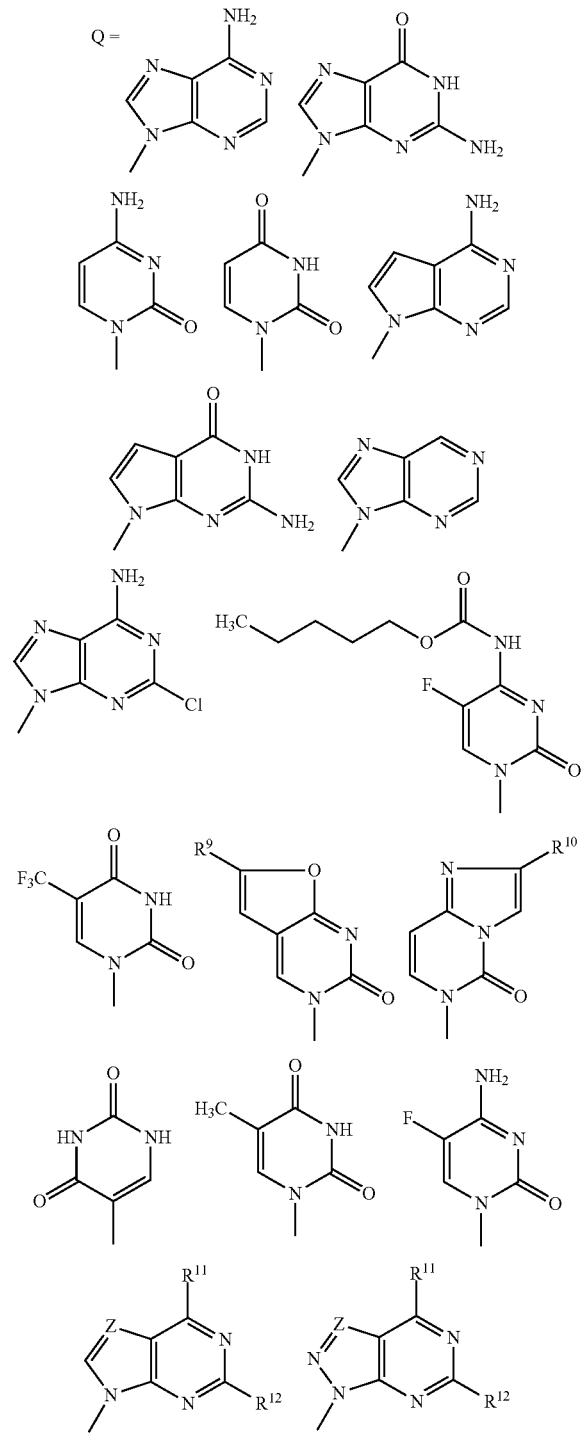

wherein (i) Z is N or $CR^{16}$;

(ii) $R^9$, $R^{10}$, $R^{11}$, $R^{12}$, $R^{13}$, $R^{14}$ and $R^{15}$ are independently H, F, Cl, Br, I, OH, OR', SH, SR', SeH, SeR', $NH_2$, NHR', $NR'_2$, $NHNH_2$, $NR'NH_2$, NR'NHR', $NHNR'_2$, $NR'NR'_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, $CH=CHCO_2H$, or $CH=CHCO_2R'$, wherein R' is an optionally substituted alkyl, which includes, but is not limited to, an optionally substituted $C_1$-$C_{20}$ alkyl, an optionally substituted lower alkyl, an optionally substituted cycloalkyl, an optionally substituted alkynyl of $C_2$-$C_6$, an optionally substituted lower alkenyl of $C_2$-$C_6$, an optionally substituted aryl, an optionally substituted heteroaryl, an optionally substituted sulfonyl, or optionally substituted acyl, which includes but is not limited to C(=O) alkyl, or alternatively, in the instance of $NR'_2$, each R' comprise at least one C atom that are joined to form a heterocycle comprising at least two carbon atoms;

(iii) $Y_5$ is selected from O, S, and Se;

(iv) $R^{16}$ is H, halogen (including F, Cl, Br, I), OH, OR', SH, SR', $NH_2$, NHR', $NR'_2$, $NO_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $C(=O)NH_2$, $C(=O)NHR'$, $C(=O)NR'_2$, $CH=CHCO_2H$, or $CH=CHCO_2R'$, aryl, or heteroaryl.

A second embodiment of the invention is directed to a compound represented by formula I-2:

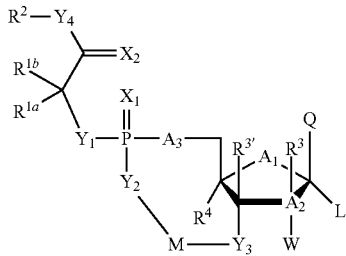

I-2 wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, or $C_1$-$C_6$ alkyl, aryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to form a phosphonate or phosphonamidate;

(g) L and $R^4$ are independently selected from H, a lower alkyl, CN, vinyl, O-(lower alkyl), hydroxyl lower alkyl (i.e., $-(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $X_1$ and $X_2$ are independently selected from O, S or Se;

(i) M is a molecular bridge selected from $CR^{5a}R^{5b}$, $(CR^{5a}R^{5b})_dOC(=O)$, and $(CR^{5a}R^{5b})_dC(=O)$, where d is 1 to 4;

(j) $Y_1$, $Y_2$, $Y_3$, and $Y_4$ are selected as follows: (i) $Y_1$ is selected from O, S, Se, and $NR^8$; (ii) $Y_2$ is selected from O, S, Se, and $NR^{8'}$; (iii) $Y_3$ is selected from O, S, Se, and $NR^{8''}$; (iv) $Y_4$ is selected from O, S, Se, and $NR^{8'''}$; (v) $R^8$ and $R^{1a}$ or $R^{1b}$ together are $(CH_2)_n$ so as to form a cyclic ring that includes the adjoining N and C atoms, where n is 2 to 4, and $Y_1$ is $NR^8$; (vi) $R^{8'}$ and $R^{5a}$ or $R^{5b}$ together are $(CH_2)_n$ so as to form a cyclic ring that includes the adjoining N and C atoms, where n is 2 to 4 and $Y_2$ is $NR^{8'}$; (vii) $R^{8''}$ and $R^{5a}$ or $R^{5b}$ together are $(CH_2)_n$ so as to form a cyclic ring that includes the adjoining N and C atoms, where n is 2 to 4 and $Y_3$ is $NR^{8''}$; (viii) $Y_3$ is O, and $Y_2$ is $NR^{8'}$, so that $Y_2CR^{5a}R^{5b}C(=O)Y_3$ represents an ester of a natural or modified α-amino acid such as glycinyl ($NHCH_2CO_2$), or $Y_2$ is O or S; (ix) the said modified α-amino acids can be a β-, γ-, or δ-amino acid or its analogues represented by $Y_2(CR^{5a}R^{5b})_dC(=O)Y_3$ where d is 2 to 4; (x) $Y_2$ can be O or S of an α-amino acid residue as in serine (OH), threonine (OH), and cysteine (SH), and the amino can be substituted or unsubstituted;

(k) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(l) $R^8$, $R^{8'}$, $R^{8''}$, and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$, $R^{8'}$, $R^{8''}$, or $R^{8'''}$ in $Y_x$ can be the same or different groups where x is 1 to 4;

(m) $R^{1a}$ and $R^{1b}$ are selected as follows: (i) $R^{1a}$ and $R^{1b}$ are independently selected from hydrogen, $C_1$-$C_{10}$ alkyl, cycloalkyl, $-(CH_2)_c NR^{1'}{}_2$, hydroxy($C_1$-$C_6$)alkyl, $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl, heteroaryl, arylalkyl($C_1$-$C_3$), and heteroarylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1'''}$ is $-OR^{1'}$ or $-N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $-CH_2OH$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4 and $Y_1$ is $NR^8$; (vii) $R^{1b}$ is hydrogen and $R^{1a}$ and $R^8$ together are $(CH_2)_n$ so as to form a cyclic ring that includes the adjoining N and C atoms, where n is 2 to 4 and $Y_1$ is $NR^8$;

(n) $R^{5a}$ and $R^{5b}$ are selected as follows: (i) $R^{5a}$, $R^{5b}$ are independently selected from hydrogen, $C_1$-$C_{10}$ alkyl, cycloalkyl, $-(CH_2)_c(NR^{1'})_2$, hydroxyalkyl ($C_1$-$C_6$), $-CH_2SH$, $-(CH_2)_2S(=O)_dMe$, $-(CH_2)_3NHC(=NH)$ $NH_2$, (1H-indol-3-yl)methyl, (1H-imidazol-4-yl)methyl, —$(CH_2)_cCOR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where $Y_2$ is $NR^{8'}$, and n is 2 to 4; (v) $R^{5b}$ is hydrogen and $R^{5a}$ and $R^{8'}$ together are $(CH_2)_n$ so as to form a cyclic ring that includes the adjoining N and C atoms, where $Y_2$ is $NR^{8'}$, and n is 2 to 4; (vi) $R^{5a}$ is hydrogen and $R^{5b}$ and $R^{8''}$ together are $(CH_2)_n$ so as to form a cyclic ring that includes the adjoining N and C atoms where $Y_3$ is $NR^{8''}$, and n is 2 to 4; (vii) $R^{5b}$ is hydrogen and $R^{5a}$ and $R^{8''}$ together are $(CH_2)_n$ so as to form a cyclic ring that includes the adjoining N and C atoms, where $Y_3$ is $NR^{8''}$, and n is 2 to 4;

(o) Q is any nucleic acid base and analogues, either a naturally occurring or modified purine or pyrimidine base.

A third embodiment of the invention is directed to a compound represented by formula I-3:

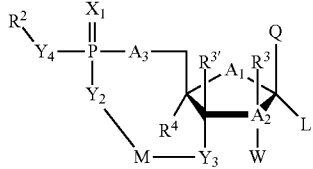

I-3 wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to form a phosphonate or phosphonamidate;

(g) L and $R^4$ are independently selected from H, a lower alkyl, CN, vinyl, O-(lower alkyl), hydroxyl lower alkyl (i.e., —$(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $X_1$ is selected from O, S or Se;

(i) M is a molecular bridge selected from $CR^{5a}R^{5b}$, $(CR^{5a}R^{5b})_dOC(=O)$, and $(CR^{5a}R^{5b})_dC(=O)$, where d is 1 to 4;

(j) $Y_2$, $Y_3$, and $Y_4$ are selected as follows: (i) $Y_2$ is selected from O, S, Se, and $NR^{8'}$; (ii) $Y_3$ is selected from O, S, Se, and $NR^{8''}$; (iii) $Y_4$ is selected from O, S, Se, and $NR^{8'''}$; (iv) $R^{8'}$ and $R^{5'}$ or $R^{5b}$ together are $(CH_2)_n$ so as to form a cyclic ring that includes the adjoining N and C atoms, where n is 2 to 4 and $Y_2$ is $NR^{8'}$; (v) $R^{8''}$ and $R^{5a}$ or $R^{5b}$ together are $(CH_2)_n$ so as to form a cyclic ring that includes the adjoining N and C atoms, where n is 2 to 4, and $Y_3$ is $NR^{8''}$; (vi) $Y_3$ is O, and $Y_2$ is $NR^{8'}$, so that $Y_2CR^{5a}R^{5b}C(=O)Y_3$ represents an ester of a natural or modified α-amino acid such as glycinyl ($NHCH_2CO_2$), or $Y_2$ is O or S; (vii) the said modified α-amino acids can be a β-, γ-, or δ-amino acid or its analogues represented by $Y_2(CR^{5a}R^{5b})_dC(=O)Y_3$ where d is 2 to 4; (viii) $Y_2$ can be O or S of an α-amino acid residue as in serine (OH), threonine (OH), and cysteine (SH), and the amino can be substituted or unsubstituted;

(k) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(l) $R^{8'}$, $R^{8''}$, and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^{8'}$, $R^{8''}$, or $R^{8'''}$ in $Y_x$ can be the same or different groups where x is 2 to 4;

(m) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_cCOR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where $Y_2$ is $NR^{8'}$, and n is 2 to 4; (v) $R^{5b}$ is hydrogen and $R^{5a}$ and $R^{8'}$ together are $(CH_2)_n$ so as to form a cyclic ring that includes the adjoining N and C atoms, where $Y_2$ is $NR^{8'}$, and n is 2 to 4; (vi) $R^{5a}$ is hydrogen and $R^{5b}$ and $R^{8''}$ together are $(CH_2)_n$ so as to form a cyclic ring that includes the adjoining N and C atoms where $Y_3$ is $NR^{8''}$, and n is 2 to 4; (vii) $R^{5b}$ is hydrogen and $R^{5a}$ and $R^{8''}$ together are $(CH_2)_n$ so as to form a cyclic ring that includes the adjoining N and C atoms, where $Y_3$ is $NR^{8''}$, and n is 2 to 4;

(n) Q is any nucleic acid base and analogues, either a naturally occurring or modified purine or pyrimidine base.

A fourth embodiment of the invention is directed to a compound represented by formula I-2-1:

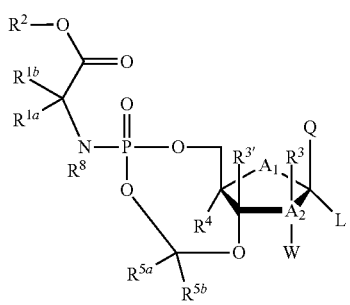

I-2-1 wherein (a) $A_1$ is selected from O, S, Se, $NR^6$, C=$CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, C=$CH_2$, or C=$CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) L and $R^4$ are independently selected from H, a lower alkyl, CN, vinyl, O-(lower alkyl), hydroxyl lower alkyl (i.e., —$(CH_2)_p$OH, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(f) $R^{1a}$ and $R^{1b}$ are selected as follows: (i) $R^{1a}$ and $R^{1b}$ are independently selected from hydrogen, $C_1$-$C_{10}$ alkyl, cycloalkyl, —$(CH_2)_c NR^{1''}_2$, hydroxy($C_1$-$C_6$)alkyl, —$CH_2SH$, —$(CH_2)_2S(=O)_d$Me, —$(CH_2)_3NHC(=NH)NH_2$, (1H-indol-3-yl)methyl, (1H-imidazol-4-yl)methyl, —$(CH_2)_e COR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^1$ is independently hydrogen or alkyl, which includes, but is not limited to, $C_1$-$C_{20}$ alkyl, and $R^{1'''}$ is —$OR^{1'}$ or —$N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4; (vii) $R^{1b}$ is hydrogen and $R^{1a}$ and $R^8$ together are $(CH_2)_n$ so as to form a cyclic ring that includes the adjoining N and C atoms, where n is 2 to 4;

(g) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_d$Me, —$(CH_2)_3NHC(=NH)NH_2$, (1H-indol-3-yl)methyl, (1H-imidazol-4-yl)methyl, —$(CH_2)_e COR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(h) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(i) $R^8$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(j) Q is any nucleic acid base and analogues, either a naturally occurring or modified purine or pyrimidine base.

A fifth embodiment of the invention is directed to a compound represented by formula I-2-2:

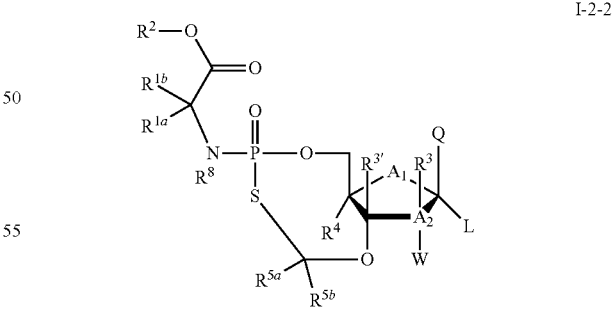

I-2-2 wherein (a) $A_1$ is selected from O, S, Se, $NR^6$, C=$CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ independently selected from are H, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) L and $R^4$ are independently selected from H, a lower alkyl, CN, vinyl, O-(lower alkyl), hydroxyl lower alkyl (i.e., —$(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(f) $R^{1a}$ and $R^{1b}$ are selected as follows: (i) $R^{1a}$ and $R^{1b}$ are independently selected from hydrogen, $C_1$-$C_{10}$ alkyl, cycloalkyl, —$(CH_2)_cNR^{1'}{}_2$, hydroxy($C_1$-$C_6$)alkyl, —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1''}$ is —$OR^{1'}$ or —$N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'$-$OH)$-$Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'$-$OH)$-$Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4; (vii) $R^{1b}$ is hydrogen and $R^{1a}$ and $R^8$ together are $(CH_2)_n$ so as to form a cyclic ring that includes the adjoining N and C atoms, where n is 2 to 4;

(g) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(h) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(i) $R^8$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(j) Q is any nucleic acid base and analogues, either a naturally occurring or modified purine or pyrimidine base.

A sixth embodiment of the invention is directed to a compound represented by formula I-2-3:

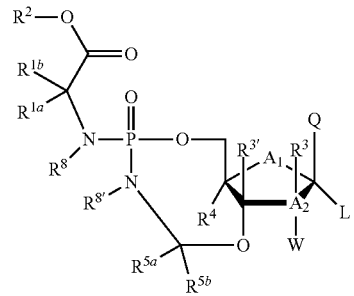

I-2-3

(a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) L and $R^4$ are independently selected from H, a lower alkyl, CN, vinyl, O-(lower alkyl), hydroxyl lower alkyl (i.e., —$(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(g) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(h) $R^8$ and $R^{8'}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$ and $R^{8'}$ can be the same or different groups;

(i) $R^{1a}$ and $R^{1b}$ are selected as follows: (i) $R^{1a}$ and $R^{1b}$ are independently selected from hydrogen, $C_1$-$C_{10}$ alkyl, cycloalkyl, —$(CH_2)_c NR^{1'}_2$, hydroxyl $(C_1$-$C_6)$alkyl, —$CH_2SH$, —$(CH_2)_2S(\!=\!O)_d Me$, —$(CH_2)_3 NHC(\!=\!NH)NH_2$, (1H-indol-3-yl)methyl, (1H-imidazol-4-yl)methyl, —$(CH_2)_e COR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1''}$ is —$OR^{1'}$ or —$N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(\!=\!O)NH_2$, $CH_2CH_2COOH$, $CH_2CH_2C(\!=\!O)NH_2$, $CH_2CH_2CH_2CH_2NH_2$, —$CH_2CH_2CH_2NHC(\!=\!NH)NH_2$, $CH_2Ph$, $CH_2((4'\text{-}OH)\text{-}Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(\!=\!O)NH_2$, $CH_2CH_2COOH$, $CH_2CH_2C(\!=\!O)NH_2$, $CH_2CH_2CH_2CH_2NH_2$, —$CH_2CH_2CH_2NHC(\!=\!NH)NH_2$, $CH_2Ph$, $CH_2((4'\text{-}OH)\text{-}Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ and $R^8$ together are $(CH_2)_m$ so as to form a spiro ring, where m is 2 to 5; (vi) $R^{1a}$ is hydrogen, and $R^{1b}$ and $R^8$ together are $(CH_2)_n$ so as to form a cyclic ring that includes the adjoining N and C atoms, where n is 2 to 4; (vii) $R^{1b}$ is hydrogen, and $R^{1a}$ and $R^8$ together are $(CH_2)_n$ so as to form a cyclic ring that includes the adjoining N and C atoms, where n is 2 to 4;

(j) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl $(C_1$-$C_6)$, —$CH_2SH$, —$(CH_2)_2S(\!=\!O)_d Me$, —$(CH_2)_3 NHC(\!=\!NH)NH_2$, (1H-indol-3-yl)methyl, (1H-imidazol-4-yl)methyl, —$(CH_2)_e COR^{1''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen, and $R^{5b}$ and $R^{8'}$ together are $(CH_2)_n$ so as to form a cyclic ring that includes the adjoining N and C atoms where n is 2 to 4; (v) $R^{5b}$ is hydrogen, and $R^{5a}$ and $R^{8'}$ together are $(CH_2)_n$ so as to form a cyclic ring that includes the adjoining N and C atoms, where n is 2 to 4;

(k) Q is any nucleic acid base and analogues, either a naturally occurring or modified purine or pyrimidine base.

A seventh embodiment of the invention is directed to a compound represented by formula I-2-4:

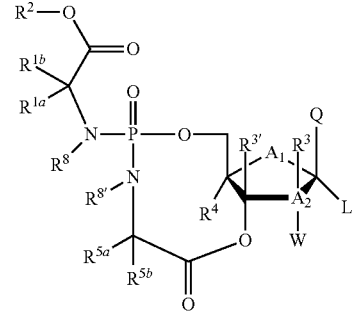

I-2-4

(a) $A_1$ is selected from O, S, Se, $NR^6$, $C\!=\!CH_2$, and $CR^{7a}R^{7b}$, where (i) $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, aryl, and heteroaryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C\!=\!CH_2$, or $C\!=\!CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, OH, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) L and $R^4$ are independently selected from H, a lower alkyl, CN, vinyl, O-(lower alkyl), hydroxyl lower alkyl (i.e., —$(CH_2)_p OH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(g) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(h) $R^8$ and $R^{8'}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$ and $R^{8'}$ can be the same or different groups;

(i) $R^{1a}$ and $R^{1b}$ are selected as follows: (i) $R^{1a}$ and $R^{1b}$ are independently selected from hydrogen, $C_1$-$C_{10}$ alkyl, cycloalkyl, —(CH$_2$)$_c$NR$^{1'}$$_2$, hydroxyl (C$_1$-C$_6$)alkyl, —CH$_2$SH, —(CH$_2$)$_2$S(═O)$_d$Me, —(CH$_2$)$_3$NHC(═NH)NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^{1'}$ is independently hydrogen or alkyl, which includes, but is not limited to, C$_1$-C$_{20}$ alkyl, and R$^{1'''}$ is —OR$^{1'}$ or —N(R$^{1'}$)$_2$; (ii) R$^{1a}$ is H and R$^{1b}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(═O)NH$_2$, CH$_2$CH$_2$COOH, CH$_2$CH$_2$C(═O)NH$_2$, CH$_2$CH$_2$CH$_2$CH$_2$NH$_2$, —CH$_2$CH$_2$CH$_2$NHC(═NH)NH$_2$, CH$_2$Ph, CH$_2$((4'-OH)-Ph), CH$_2$-imidazol-4-yl, or lower cycloalkyl; or (iii) R$^{1b}$ is H and R$^{1a}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(═O)NH$_2$, CH$_2$CH$_2$COOH, CH$_2$CH$_2$C(═O)NH$_2$, CH$_2$CH$_2$CH$_2$CH$_2$NH$_2$, —CH$_2$CH$_2$CH$_2$NHC(═NH)NH$_2$, CH$_2$Ph, CH$_2$((4'-OH)-Ph), CH$_2$-imidazol-4-yl, or lower cycloalkyl; (iv) R$^{1a}$ and R$^{1b}$ both are C$_1$-C$_6$ alkyl; (v) R$^{1a}$ and R$^{1b}$ together are (CH$_2$)$_m$ so as to form a spiro ring, where m is 2 to 5; (vi) R$^{1a}$ is hydrogen and R$^{1b}$ and R$^8$ together are (CH$_2$)$_n$ so as to form a cyclic ring that includes the adjoining N and C atoms, where n is 2 to 4; (vii) R$^{1b}$ is hydrogen and R$^{1a}$ and R$^8$ together are (CH$_2$)$_n$ so as to form a cyclic ring that includes the adjoining N and C atoms, where n is 2 to 4;

(j) R$^{5a}$ and R$^{5b}$ are selected as follows: (i) R$^{5a}$, R$^{5b}$ are independently selected from hydrogen, C$_1$-C$_{10}$ alkyl, cycloalkyl, —(CH$_2$)$_c$(NR$^{1'}$)$_2$, hydroxyalkyl (C$_1$-C$_6$), —CH$_2$SH, —(CH$_2$)$_2$S(═O)$_d$Me, —(CH$_2$)$_3$NHC(═NH)NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^{1'}$ is independently hydrogen or C$_1$-C$_6$ alkyl and R$^{1'''}$ is —OR$^{1'}$ or —N(R$^{1'}$)$_2$; (ii) R$^{5a}$ and R$^{5b}$ both are C$_1$-C$_6$ alkyl; (iii) R$^{5a}$ and R$^{5b}$ together are (CH$_2$)$_m$ so as to form a spiro ring, where m is 2 to 5; (iv) R$^{5a}$ is hydrogen and R$^{5b}$ and R$^{8'}$ together are (CH$_2$)$_n$ so as to form a cyclic ring that includes the adjoining N and C atoms where n is 2 to 4; (v) R$^{5b}$ is hydrogen and R$^{5a}$ and R$^{8'}$ together are (CH$_2$)$_n$ so as to form a cyclic ring that includes the adjoining N and C atoms, where n is 2 to 4;

(k) Q is any nucleic acid base and analogues, either a naturally occurring or modified purine or pyrimidine base.

A seventh embodiment of the invention is directed to a compound represented by formula I-3-1:

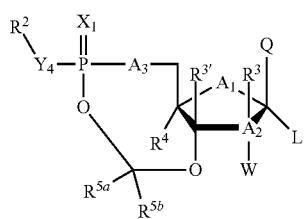

I-3-1 wherein
(a) A$_1$ is selected from O, S, Se, NR$^6$, C═CH$_2$, and CR$^{7a}$R$^{7b}$, where (i) R$^6$ is R$^{6'}$ or COR$^{6'}$ where R$^{6'}$ is H, alkyl, aryl, OH, alkoxy, aryloxy, heteroaryloxy, alkylamino, arylamino, or heteroarylamino, and R$^{7a}$ and R$^{7b}$ are independently selected from H, OH, SH, F, Cl, alkyl, aryl, and heteroaryl; (ii) CR$^{7a}$R$^{7b}$ is C(CH$_2$)$_m$ so as to form a spiro ring where m is 2 to 5, or is a substituted or unsubstituted spiro epoxide, aziridine, or oxetane; (iii) R$^4$ is CH$_2$ so as to form a substituted bicyclo[3.1.0]hexane including A$_1$CR$^4$;

(b) A$_2$R$^3$W is selected as follows: (i) A$_2$R$^3$W is (H)$_2$ (so as to form an acyclic nucleoside), CH$_2$, C═CH$_2$, or C═CR$^{7a}$R$^{7b}$ where R$^{7a}$ and R$^{7b}$ are defined as in (a); (ii) A$_2$R$^3$W is C(CH$_2$)$_m$ where m is 2 to 5 so as to form a spiro ring or is a substituted or unsubstituted spiro epoxide, aziridine, or oxetane;

(c) W is H, F, halogen, OH, OMe, NHR$^6$ or N$_3$ where A$_2$R$^3$ is CR$^3$, and R$^6$ is R$^{6'}$ or COR$^{6'}$ where R$^{6'}$ is H, OH, alkyl, aryl, heteroaryl, alkoxy, aryloxy, heteroaryloxy, alkylamino, arylamino, or heteroarylamino;

(d) R$^3$ is H, CH$_3$, CH$_2$F, CHF$_2$, CF$_3$, F, CN, C$_1$-C$_6$ alkyl, aryl or heteroaryl, where A$_2$W is CW;

(e) R$^{3'}$ is H, CH$_3$, CH$_2$F, CHF$_2$, CF$_3$, F, CN, C$_1$-C$_6$ alkyl, aryl, alkoxy carbonyl, or thioalkoxy carbonyl, C$_1$-C$_{10}$ alkylcarbamoyl (C$_1$-C$_{10}$ alkylaminocarbonyl), arylcarbamoyl, or heteroarylcarbamoyl;

(f) A$_3$ is selected as follows: (i) A$_3$ is O, S, Se, or NR$^6$ where R$^6$ is H, OR$^{6'}$, alkyl, aryl, COR$^{6'}$, or CO$_2$R$^{6'}$, where R$^{6'}$ is H, alkyl, aryl, or heteroaryl; (ii) A$_3$CH$_2$ can be optionally replaced with CH$_2$A$_3$, or CF$_2$A$_3$, so as to represent a phosphonate or phosphonamidate;

(g) L and R$^4$ are independently selected from H, a lower alkyl, CN, vinyl, O-(lower alkyl), hydroxyl lower alkyl (i.e., —(CH$_2$)$_p$OH, where p is 1 to 6, including hydroxyl methyl (CH$_2$OH)), CH$_2$F, N$_3$, CH$_2$CN, CH$_2$NH$_2$, CH$_2$NHCH$_3$, CH$_2$N(CH$_3$)$_2$, alkynyl (optionally substituted), or halogen, including F, Cl, Br, or I;

(h) Y$_4$ is O, S, Se, or NR$^{8''''}$ where R$^{8''''}$ is hydrogen, alkyl, or aryl as defined below;

(i) R$^2$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, and substituted heteroaryl;

(j) R$^{8''''}$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(k) X$_1$ is O, S or Se;

(l) R$^{5a}$ and R$^{5b}$ are selected as follows: (i) R$^{5a}$, R$^{5b}$ are independently selected from hydrogen, C$_1$-C$_{10}$ alkyl, cycloalkyl, —(CH$_2$)$_c$(NR$^{1'}$)$_2$, hydroxyalkyl (C$_1$-C$_6$), —CH$_2$SH, —(CH$_2$)$_2$S(═O)$_d$Me, —(CH$_2$)$_3$NHC(═NH)NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^{1'}$ is independently hydrogen or C$_1$-C$_6$ alkyl and R$^{1'''}$ is —OR$^{1'}$ or —N(R$^{1'}$)$_2$; (ii) R$^{5a}$ and R$^{5b}$ both are C$_1$-C$_6$ alkyl; (iii) R$^{5a}$ and R$^{5b}$ together are (CH$_2$)$_m$ so as to form a spiro ring, where m is 2 to 5;

(m) Q is any nucleic acid base and analogues, either a naturally occurring or modified purine or pyrimidine base.

An eighth embodiment of the invention is directed to a compound represented by formula I-3-2:

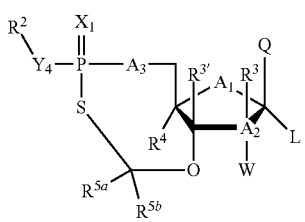

wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is $R^{6'}$ or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to form a phosphonate or phosphonamidate;

(g) L and $R^4$ are independently selected from H, a lower alkyl, CN, vinyl, O-(lower alkyl), hydroxyl lower alkyl (i.e., $—(CH_2)_pOH$, where p is 1 to 6, including hydroxyl methyl $(CH_2OH)$), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $Y_4$ is O, S, Se, or $NR^{8'''}$ where $R^{8'''}$ is hydrogen, alkyl, or aryl as defined below;

(i) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(j) $R^{8'''}$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(k) $X_1$ is O, S or Se;

(l) $R^{5a}$ and $R^{5b}$ are selected as follows: (i) $R^{5a}$, $R^{5b}$ are independently selected from hydrogen, $C_1$-$C_{10}$ alkyl, cycloalkyl, $—(CH_2)_c(NR^{1'})_2$, hydroxyalkyl $(C_1$-$C_6)$, $—CH_2SH$, $—(CH_2)_2S(=O)_dMe$, $—(CH_2)_3NHC(=NH)NH_2$, (1H-indol-3-yl)methyl, (1H-imidazol-4-yl)methyl, $—(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is $—OR^{1'}$ or $—N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(m) Q is any nucleic acid base and analogues, either a naturally occurring or modified purine or pyrimidine base.

A ninth embodiment of the invention is directed to a compound represented by formula I-3-3:

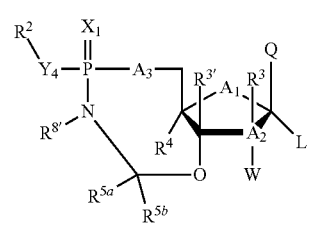

wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, aryl, and heteroaryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is H, OH, alkyl, aryl, heteroaryl, or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to represent a phosphonate or phosphonamidate;

(g) L and $R^4$ are independently selected from H, a lower alkyl, CN, vinyl, O-(lower alkyl), hydroxyl lower alkyl (i.e., $—(CH_2)_pOH$, where p is 1 to 6, including hydroxyl methyl $(CH_2OH)$), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $Y_4$ is O, S, Se, or $NR^{8'''}$ where $R^{8'''}$ is hydrogen, alkyl, or aryl as defined below;

(i) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(j) $R^{8'}$ and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$ and $R^{8'}$ can be the same or different groups;

(k) $X_1$ is O, S or Se;

(l) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where n is 2 to 4; (v) $R^{5b}$ is hydrogen and $R^{5a}$ and $R^{8'}$ together are $(CH_2)_n$ so as to form a cyclic ring that includes the adjoining N and C atoms, where n is 2 to 4;

(m) Q is any nucleic acid base and analogues, either a naturally occurring or modified purine or pyrimidine base.

A tenth embodiment of the invention is directed to a compound represented by formula I-3-4:

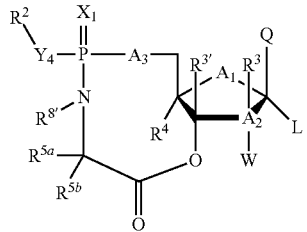

wherein (a) $A_1$ is selected from O, S, Se, $NR^6$, $C=CH_2$, and $CR^{7a}R^{7b}$, where (i) $R^6$ is $R^{6'}$ or $COR^{6'}$ where $R^{6'}$ is H, alkyl, aryl, OH, alkoxy, aryloxy, heteroaryloxy, alkylamino, arylamino, or heteroarylamino, and $R^{7a}$ and $R^{7b}$ are independently selected from H, OH, SH, F, Cl, alkyl, and aryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

(b) $A_2R^3W$ is selected as follows: (i) $A_2R^3W$ is $(H)_2$ (so as to form an acyclic nucleoside), $CH_2$, $C=CH_2$, or $C=CR^{7a}R^{7b}$ where $R^{7a}$ and $R^{7b}$ are defined as in (a); (ii) $A_2R^3W$ is $C(CH_2)_m$ where m is 2 to 5 so as to form a spiro ring or is a substituted or unsubstituted spiro epoxide, aziridine, or oxetane;

(c) W is H, F, halogen, OH, OMe, $NHR^6$ or $N_3$ where $A_2R^3$ is $CR^3$, and $R^6$ is H, OH, alkyl, aryl, heteroaryl, or $COR^{6'}$ where $R^{6'}$ is H, alkyl, aryl, heteroaryl, alkoxy, aryloxy, heteroaryloxy, alkylamino, arylamino, or heteroarylamino;

(d) $R^3$ is H, $CH_3$, $CH_2F$, $CHF_2$, $CF_3$, F, CN, $C_1$-$C_6$ alkyl, aryl or heteroaryl, where $A_2W$ is CW;

(e) $R^{3'}$ is H, $CH_3$, $CH_2F$, $CHF_2$, $CF_3$, F, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;

(f) $A_3$ is selected as follows: (i) $A_3$ is O, S, Se, or $NR^6$ where $R^6$ is H, $OR^{6'}$, alkyl, aryl, $COR^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to form a phosphonate or phosphonamidate;

(g) L and $R^4$ are independently selected from H, a lower alkyl, CN, vinyl, O-(lower alkyl), hydroxyl lower alkyl (i.e., —$(CH_2)_pOH$, where p is 1 to 6, including hydroxyl methyl ($CH_2OH$)), $CH_2F$, $N_3$, $CH_2CN$, $CH_2NH_2$, $CH_2NHCH_3$, $CH_2N(CH_3)_2$, alkynyl (optionally substituted), or halogen, including F, Cl, Br, or I;

(h) $Y_4$ is O, S, Se, or $NR^{8'''}$ where $R^{8'''}$ is hydrogen, alkyl, or aryl as defined below;

(i) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(j) $R^{8'}$ and $R^{8'''}$ are independently selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino; $R^8$ and $R^{8'}$ can be the same or different groups;

(k) $X_1$ is O, S or Se;

(l) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a Spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where n is 2 to 4; (v) $R^{5b}$ is hydrogen and $R^{5a}$ and $R^{8'}$ together are $(CH_2)_n$ so as to form a cyclic ring that includes the adjoining N and C atoms, where n is 2 to 4;

(m) Q is any nucleic acid base and analogues, either a naturally occurring or modified purine or pyrimidine base.

An eleventh embodiment of the invention is directed to a compound represented by formula I-2-1-1:

35

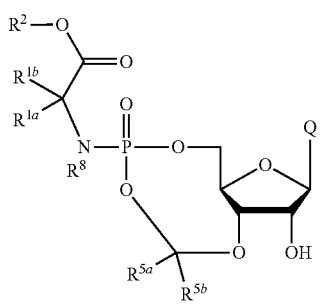

I-2-1-1 wherein (a) (i) $R^{1a}$ and $R^{1b}$ are independently selected from hydrogen, $C_1$-$C_{10}$ alkyl, cycloalkyl, —$(CH_2)_cNR^{1'}{}_2$, hydroxyl ($C_1$-$C_6$)alkyl, —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1'''}$ is —$OR^{1'}$ or —$N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(COH_2)_m$ so as to form a spiro ring; (vi) $R^{1a}$ is hydrogen and $R^{1b}$ and $R^8$ together are $(CH_2)_n$ so as to form a cyclic ring that includes the adjoining N and C atoms, where n is 2 to 4; (vii) $R^{1b}$ is hydrogen and $R^{1a}$ and $R^8$ together are $(CH_2)_n$ so as to form a cyclic ring that includes the adjoining N and C atoms, where n is 2 to 4;

(b) (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^1$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(c) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(d) $R^8$ is selected from hydrogen, $C_1$-$C_{10}$ alkyl, $C_1$-$C_{10}$ alkyl optionally substituted with a lower alkyl, alkoxyalkyl,

36 di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(e) Q is any nucleic acid base and analogues, either a naturally occurring or modified purine or pyrimidine base.

A twelfth embodiment of the invention is directed to a compound represented by formula I-2-1-2:

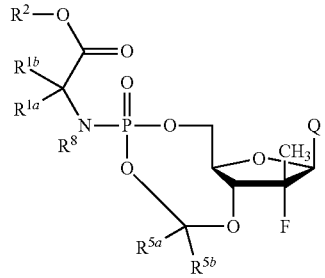

I-2-1-2 wherein (a) (i) $R^{1a}$ and $R^{1b}$ are independently selected from hydrogen, $C_1$-$C_{10}$ alkyl, cycloalkyl, —$(CH_2)_xNR^{1'}{}_2$, hydroxy($C_1$-$C_6$)alkyl, —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or alkyl, which includes, but is not limited to, $C_1$-$C_{20}$ alkyl, and $R^{1'''}$ is —$OR^{1'}$ or —$N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, —$CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, —$CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1$-$C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4; (vii) $R^{1b}$ is hydrogen and $R^{1a}$ and $R^8$ together are $(CH_2)_n$ so as to form a cyclic ring that includes the adjoining N and C atoms, where n is 2 to 4;

(b) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —N(R$^{1'}$)$_2$; (ii) R$^{5a}$ and R$^{5b}$ both are C$_1$-C$_6$ alkyl; (iii) R$^{5a}$ and R$^{5b}$ together are (CH$_2$)$_m$ so as to form a spiro ring, where m is 2 to 5;

(c) R$^2$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, and substituted heteroaryl;

(d) R$^8$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(e) Q is any nucleic acid base and analogues, either a naturally occurring or modified purine or pyrimidine base.

A thirteenth embodiment of the invention is directed to a compound represented by formula I-2-1-3:

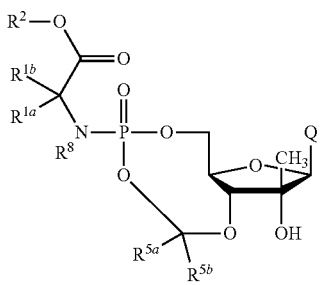

I-2-1-3 wherein (a) (i) R$^{1a}$ and R$^{1b}$ are independently selected from hydrogen, C$_1$-C$_{10}$ alkyl, cycloalkyl, —(CH$_2$)$_c$NR$^{1'}{}_2$, hydroxy(C$_1$-C$_6$)alkyl, —CH$_2$SH, —(CH$_2$)$_2$S(═O)$_d$Me, —(CH$_2$)$_3$NHC(═NH)NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^1$ is independently hydrogen or alkyl, which includes, but is not limited to, C$_1$-C$_{20}$ alkyl, and R$^{1'''}$ is —OR$^{1'}$ or —N(R$^{1'}$)$_2$; (ii) R$^{1a}$ is H and R$^{1b}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(═O)NH$_2$, CH$_2$CH$_2$COOH, CH$_2$CH$_2$C(═O)NH$_2$, CH$_2$CH$_2$CH$_2$NH$_2$, —CH$_2$CH$_2$CH$_2$NHC(═NH)NH$_2$, CH$_2$Ph, CH$_2$((4'-OH)-Ph), CH$_2$-imidazol-4-yl, or lower cycloalkyl; or (iii) R$^{1b}$ is H and R$^{1a}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$) CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(═O)NH$_2$, CH$_2$CH$_2$COOH, CH$_2$CH$_2$C(═O)NH$_2$, CH$_2$CH$_2$CH$_2$NH$_2$, —CH$_2$CH$_2$CH$_2$NHC(═NH)NH$_2$, CH$_2$Ph, CH$_2$((4'-OH)-Ph), CH$_2$-imidazol-4-yl, or lower cycloalkyl; (iv) R$^{1a}$ and R$^{1b}$ both are C$_1$-C$_6$ alkyl; (v) R$^{1a}$ and R$^{1b}$ together are (CH$_2$)$_m$ so as to form a spiro ring, where m is 2 to 5; (vi) R$^{1a}$ is hydrogen and R$^{1b}$ and R$^8$ together are (CH$_2$)$_n$ so as to form a cyclic ring that includes the adjoining N and C atoms, where n is 2 to 4; (vii) R$^{1b}$ is hydrogen and R$^{1a}$ and R$^8$ together are (CH$_2$)$_n$ so as to form a cyclic ring that includes the adjoining N and C atoms, where n is 2 to 4;

(b) R$^{5a}$ and R$^{5b}$ are selected as follows: (i) R$^{5a}$, R$^{5b}$ are independently selected from hydrogen, C$_1$-C$_{10}$ alkyl, cycloalkyl, —(CH$_2$)$_c$(NR$^{1'}$)$_2$, hydroxyalkyl (C$_1$-C$_6$), —CH$_2$SH, —(CH$_2$)$_2$S(═O)$_d$Me, —(CH$_2$)$_3$NHC(═NH) NH$_2$, (1H-indol-3-yl)methyl, (1H-imidazol-4-yl)methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^1$ is independently hydrogen or C$_1$-C$_6$ alkyl and R$^{1'''}$ is —OR$^{1'}$ or —N(R$^{1'}$)$_2$; (ii) R$^{5a}$ and R$^{5b}$ both are C$_1$-C$_6$ alkyl; (iii) R$^{5a}$ and R$^{5b}$ together are (CH$_2$)$_m$ so as to form a spiro ring, where m is 2 to 5;

(c) R$^2$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, and substituted heteroaryl;

(d) R$^8$ is selected from hydrogen, C$_1$-C$_{10}$ alkyl, C$_1$-C$_{10}$ alkyl optionally substituted with a lower alkyl, alkoxyalkyl, di(lower alkyl)-aminoalkyl, C$_1$-C$_{10}$ haloalkyl, C$_3$-C$_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(e) Q is any nucleic acid base and analogues, either a naturally occurring or modified purine or pyrimidine base.

A fourteenth embodiment of the invention is directed to a compound represented by formula I-2-1-4:

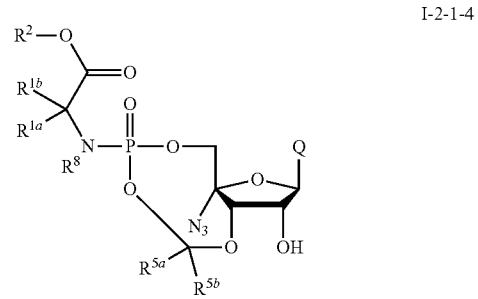

I-2-1-4 wherein (a) (i) R$^{1a}$ and R$^{1b}$ are independently selected from hydrogen, C$_1$-C$_{10}$ alkyl, cycloalkyl, —(CH$_2$)$_c$NR$^{1'}{}_2$, hydroxy(C$_1$-C$_6$)alkyl, —CH$_2$SH, —(CH$_2$)$_2$S(═O)$_d$Me, —(CH$_2$)$_3$NHC(═NH)NH$_2$, (1H-indol-3-yl)methyl, (1H-imidazol-4-yl) methyl, —(CH$_2$)$_e$COR$^{1'''}$, aryl and arylalkyl(C$_1$-C$_3$), where c is 1 to 6, d is 0 to 2, e is 0 to 3, and said aryl groups are optionally substituted with a group selected from hydroxyl, C$_1$-C$_{10}$ alkyl, C$_1$-C$_6$ alkoxy, halogen, nitro and cyano, and where R$^1$ is independently hydrogen or alkyl, which includes, but is not limited to, C$_1$-C$_{20}$ alkyl, and R$^{1'''}$ is —OR$^{1'}$ or —N(R$^{1'}$)$_2$; (ii) R$^{1a}$ is H and R$^{1b}$ is H, CH$_3$, CH$_2$CH$_3$, CH$_2$CH$_2$CH$_3$, CH(CH$_3$)$_2$, CH$_2$CH(CH$_3$)$_2$, CH(CH$_3$)CH$_2$CH$_3$, CH$_2$-indol-3-yl, —CH$_2$CH$_2$SCH$_3$, CH$_2$OH, CH(OH)CH$_3$, CH$_2$SH, CH$_2$CO$_2$H, CH$_2$C(═O) NH$_2$, CH$_2$CH$_2$COOH, CH$_2$CH$_2$C(═O)NH$_2$, CH$_2$CH$_2$CH$_2$NH$_2$, —CH$_2$CH$_2$CH$_2$NHC(═NH)NH$_2$, CH$_2$Ph, CH$_2$((4'-OH)-Ph), CH$_2$-imidazol-4-yl, or lower cycloalkyl; or (iii) R$^{1b}$ is H and R$^{1a}$ is H, CH$_3$, CH$_2$CH$_3$, $CH_2CH_2CH_3$, $CH(CH_3)_2$, $CH_2CH(CH_3)_2$, $CH(CH_3)CH_2CH_3$, $CH_2$-indol-3-yl, $—CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $—CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1-C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4; (vii) $R^{1b}$ is hydrogen and $R^{1a}$ and $R^8$ together are $(CH_2)_n$ so as to form a cyclic ring that includes the adjoining N and C atoms, where n is 2 to 4;

(b) $R^{5a}$ and $R^{5b}$ are selected as follows: (i) $R^{5a}$, $R^{5b}$ are independently selected from hydrogen, $C_1-C_{10}$ alkyl, cycloalkyl, $—(CH_2)_c(NR^{1'})_2$, hydroxyalkyl $(C_1-C_6)$, $—CH_2SH$, $—(CH_2)_2S(=O)_dMe$, $—(CH_2)_3NHC(=NH)NH_2$, (1H-indol-3-yl)methyl, (1H-imidazol-4-yl)methyl, $—(CH_2)_eCOR^{1'''}$, aryl and arylalkyl($C_1-C_3$), where c is 1 to 6, d is 0 to 2, e is 0 to 3, and said aryl groups are optionally substituted with a group selected from hydroxyl, $C_1-C_{10}$ alkyl, $C_1-C_6$ alkoxy, halogen, nitro and cyano, and where $R^{1'}$ is independently hydrogen or $C_1-C_6$ alkyl and $R^{1'''}$ is $—OR^{1'}$ or $—N(R^{1'})_2$; (ii) $R^{5a}$ and $R^{5b}$ both are $C_1-C_6$ alkyl; (iii) $R^{5a}$ and $R^{5b}$ together are $(CH_2)_m$ so as to form a spiro ring, where m is 2 to 5;

(c) $R^2$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, and substituted heteroaryl;

(d) $R^8$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(e) Q is any nucleic acid base and analogues, either a naturally occurring or modified purine or pyrimidine base.

A fifteenth embodiment of the invention is directed to a compound represented by formula I-3-1-1:

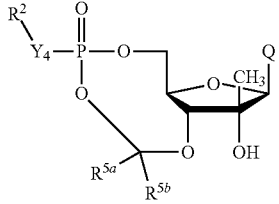

I-3-1-1 wherein (a) $Y_4$ is O, S, Se, or $NR^{8'''}$ where $R^{8'''}$ is hydrogen, alkyl, or aryl as defined below;

(b) $R^2$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, and substituted heteroaryl;

(c) $R^{8'''}$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(d) $R^{5a}$ and $R^{5b}$ are selected as follows: (i) $R^{5a}$, $R^{5b}$ are independently selected from hydrogen, $C_1-C_{10}$ alkyl, cycloalkyl, $—(CH_2)_c(NR^{1'})_2$, hydroxyalkyl $(C_1-C_6)$, $—CH_2SH$, $—(CH_2)_2S(=O)_dMe$, $—(CH_2)_3NHC(=NH)NH_2$, (1H-indol-3-yl)methyl, (1H-imidazol-4-yl)methyl, $—(CH_2)_eCOR^{1'''}$, aryl and arylalkyl($C_1-C_3$), where c is 1 to 6, d is 0 to 2, e is 0 to 3, and said aryl groups are optionally substituted with a group selected from hydroxyl, $C_1-C_{10}$ alkyl, $C_1-C_6$ alkoxy, halogen, nitro and cyano, and where $R^{1'}$ is independently hydrogen or $C_1-C_6$ alkyl and $R^{1'''}$ is $—OR^{1'}$ or $—N(R^{1'})_2$; (ii) $R^{5a}$ and $R^{5b}$ both are $C_1-C_6$ alkyl; (iii) $R^{5a}$ and $R^{5b}$ together are $(CH_2)_m$ so as to form a spiro ring, where m is 2 to 5;

(e) Q is any nucleic acid base and analogues, either a naturally occurring or modified purine or pyrimidine base.

A sixteenth embodiment of the invention is directed to a compound represented by formula I-3-1-2:

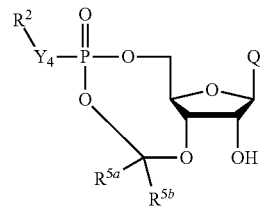

I-3-1-2 wherein (a) $Y_4$ is O, S, Se, or $NR^{8'''}$ where $R^{8'''}$ is hydrogen, alkyl, or aryl as defined below;

(b) $R^2$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, and substituted heteroaryl;

(c) $R^{8'''}$ is selected from hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(d) $R^{5a}$ and $R^{5b}$ are selected as follows: (i) $R^{5a}$, $R^{5b}$ are independently selected from hydrogen, $C_1-C_{10}$ alkyl, cycloalkyl, $—(CH_2)_c(NR^{1'})_2$, hydroxyalkyl $(C_1-C_6)$, $—CH_2SH$, $—(CH_2)_2S(=O)_dMe$, $—(CH_2)_3NHC(=NH)NH_2$, (1H-indol-3-yl)methyl, (1H-imidazol-4-yl)methyl, $—(CH_2)_eCOR^{1'''}$, aryl and arylalkyl($C_1-C_3$), where c is 1 to 6, d is 0 to 2, e is 0 to 3, and said aryl groups are optionally substituted with a group selected from hydroxyl, $C_1-C_{10}$ alkyl, $C_1-C_6$ alkoxy, halogen, nitro and cyano, and where $R^{1'}$ is independently hydrogen or $C_1-C_6$ alkyl and $R^{1'''}$ is $—OR^{1'}$ or $—N(R^{1'})_2$; (ii) $R^{5a}$ and $R^{5b}$ both are $C_1-C_6$ alkyl; (iii) $R^{5a}$ and $R^{5b}$ together are $(CH_2)_m$ so as to form a spiro ring, where m is 2 to 5;

(e) Q is any nucleic acid base and analogues, either a naturally occurring or modified purine or pyrimidine base.

A seventeenth embodiment of the invention is directed to a compound represented by formula I-3-1-3:

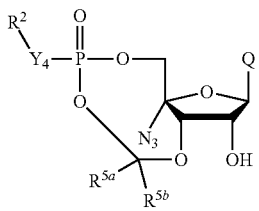

I-3-1-3 wherein (a) $Y_4$ is O, S, Se, or $NR^{8'''}$ where $R^{8'''}$ is hydrogen, alkyl, or aryl as defined below;

(b) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(c) $R^{8'''}$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(d) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(e) Q is any nucleic acid base and analogues, either a naturally occurring or modified purine or pyrimidine base.

An eighteenth embodiment of the invention is directed to a compound represented by formula I-3-1-4:

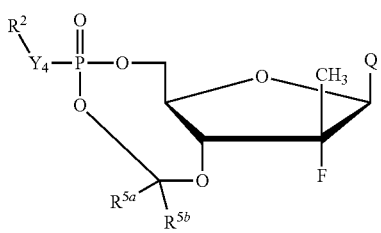

I-3-1-4 wherein (a) $Y_4$ is O, S, Se, or $NR^{8'''}$ where $R^{8'''}$ is hydrogen, alkyl, or aryl as defined below;

(b) $R^2$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, and substituted heteroaryl;

(c) $R^{8'''}$ is selected from hydrogen, $C_1$-$C_{10}$ alkyl, $C_1$-$C_{10}$ alkyl optionally substituted with a lower alkyl, alkoxyalkyl, di(lower alkyl)-aminoalkyl, $C_1$-$C_{10}$ haloalkyl, $C_3$-$C_{10}$ cycloalkyl, cycloalkyl alkyl, cycloheteroalkyl, aryl such as phenyl, heteroaryl such as pyridinyl, substituted aryl, substituted heteroaryl, OH, alkoxy, aryloxy, heteroaryloxy, alkylamino, arylamino, and heteroarylamino;

(d) $R^{5a}$ and $R^{5b}$ are selected as follows: (i) $R^{5a}$, $R^{5b}$ are independently selected from hydrogen, $C_1$-$C_{10}$ alkyl, cycloalkyl, —$(CH_2)_c(NR^{1'})_2$, hydroxyalkyl ($C_1$-$C_6$), —$CH_2SH$, —$(CH_2)_2S(=O)_dMe$, —$(CH_2)_3NHC(=NH)NH_2$, (1H-indol-3-yl)methyl, (1H-imidazol-4-yl)methyl, —$(CH_2)_eCOR^{1'''}$, aryl and arylalkyl($C_1$-$C_3$), where c is 1 to 6, d is 0 to 2, e is 0 to 3, and said aryl groups are optionally substituted with a group selected from hydroxyl, $C_1$-$C_{10}$ alkyl, $C_1$-$C_6$ alkoxy, halogen, nitro and cyano, and where $R^{1'}$ is independently hydrogen or $C_1$-$C_6$ alkyl and $R^{1'''}$ is —$OR^{1'}$ or —$N(R^{1'})_2$; (ii) $R^{5a}$ and $R^{5b}$ both are $C_1$-$C_6$ alkyl; (iii) $R^{5a}$ and $R^{5b}$ together are $(CH_2)_m$ so as to form a spiro ring, where m is 2 to 5;

(e) Q is any nucleic acid base and analogues, either a naturally occurring or modified purine or pyrimidine base.

A nineteenth embodiment of the invention is directed to a compound represented by formula I-2-1-2a:

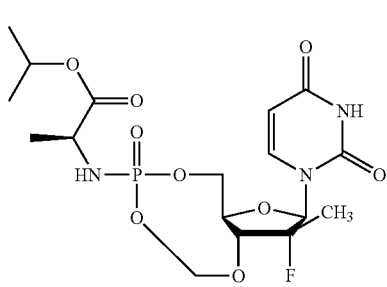

I-2-1-2a

A twentieth embodiment of the invention is directed to a compound represented by formula I-2-1-2b:

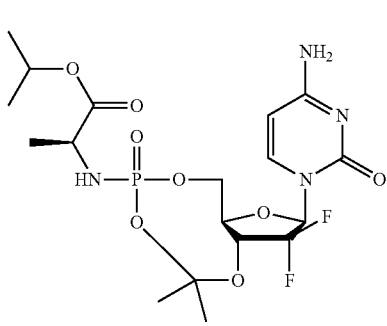

I-2-1-2b

A twenty first embodiment of the invention is directed to a compound represented by formula I-2-1-2c:

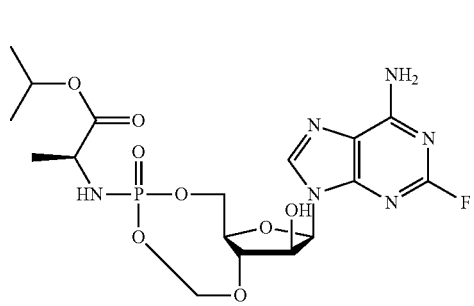

I-2-1-2c

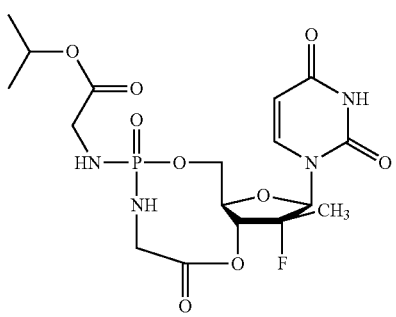

I-2-1-2g

A twenty second embodiment of the invention is directed to a compound represented by formula I-2-1-2d:

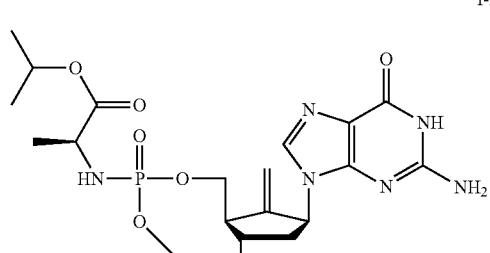

I-2-1-2d

A twenty-sixth embodiment of the invention is directed to a compound represented by formula I-2-1-2h:

A twenty-third embodiment of the invention is directed to a compound represented by formula I-2-1-2e:

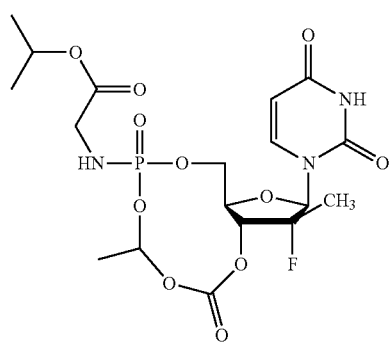

I-2-1-2h

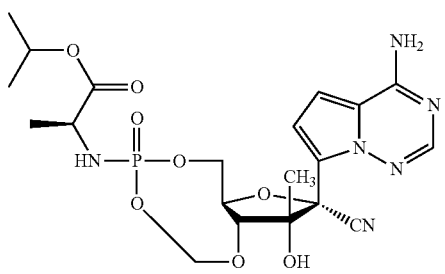

I-2-1-2e

A twenty-fourth embodiment of the invention is directed to a compound represented by formula I-2-1-2f:

A twenty-seventh embodiment of the invention is directed to a compound represented by formula I-2-1-2i:

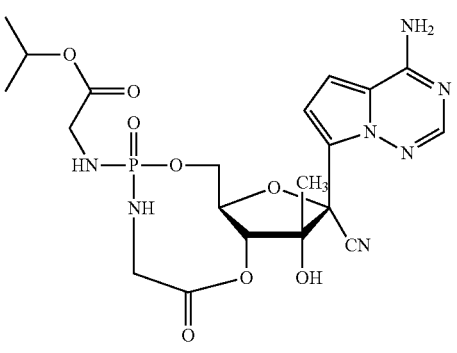

I-2-1-2i

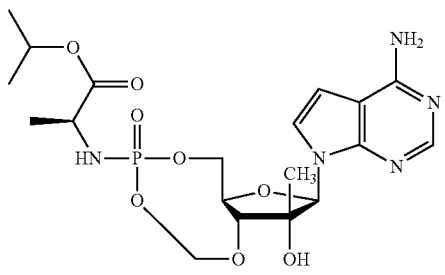

I-2-1-2f

A twenty-fifth embodiment of the invention is directed to a compound represented by formula I-2-1-2g:

A twenty-eighth embodiment of the invention is directed to a compound represented by formula I-2-1-2j:

I-2-1-2j

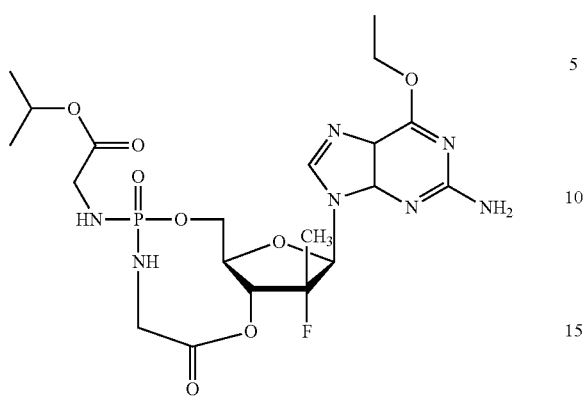

A twenty-ninth embodiment of the invention is directed to a compound represented by formula I-2-1-2k:

I-2-1-2k

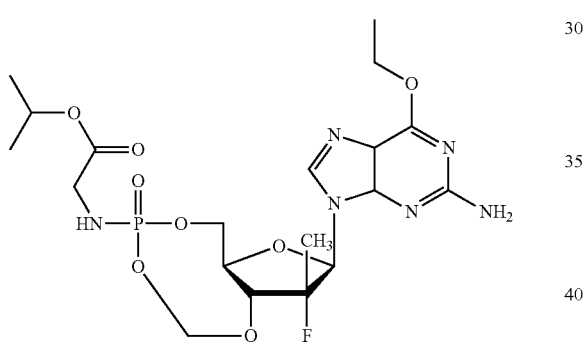

A thirtieth embodiment of the invention is directed to a compound represented by formula I-2-1-2l:

I-2-1-2l

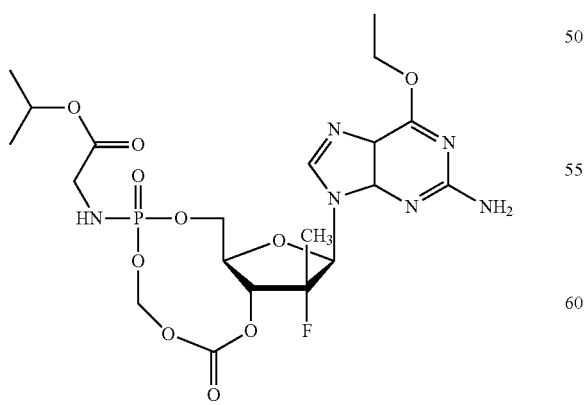

A thirty-first embodiment of the invention is directed to a compound represented by formula I-3-1-1a:

I-3-1-1a

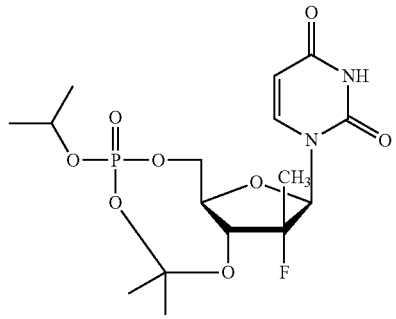

A thirty-second embodiment of the invention is directed to a compound represented by formula I-3-1-1b:

I-3-1-1b

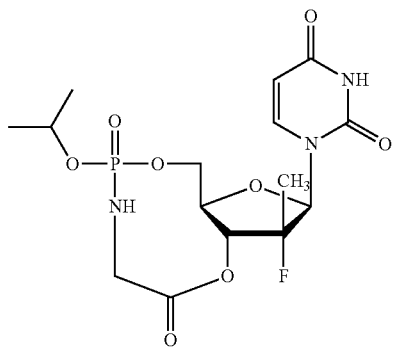

A thirty-third embodiment of the invention is directed to a compound represented by formula I-3-1-1c:

I-3-1-1c

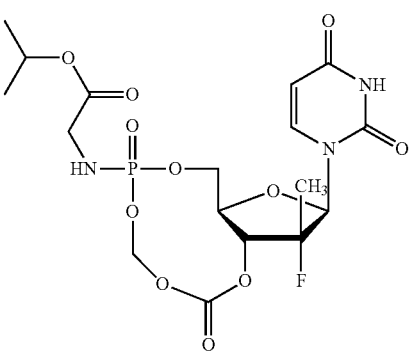

A thirty-fourth embodiment of the invention is directed to a compound represented by formula I-3-1-1d:

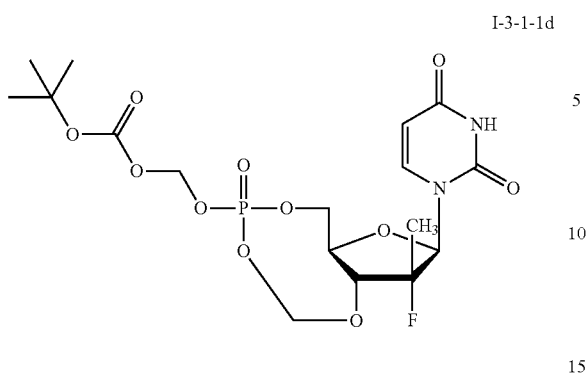
A thirty-fifth embodiment of the invention is directed to a compound represented by formula I-3-1-1e:
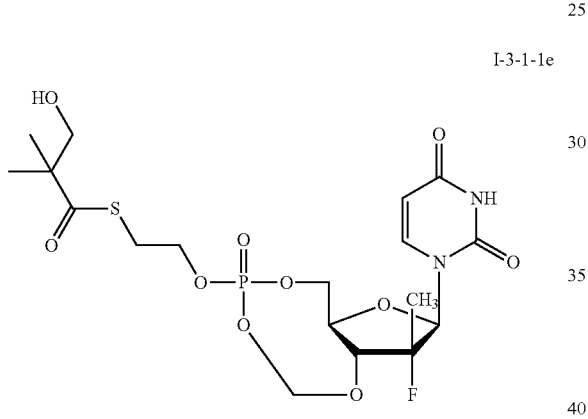
A thirty-sixth embodiment of the invention is directed to a compound represented by formula I-3-1-1f:
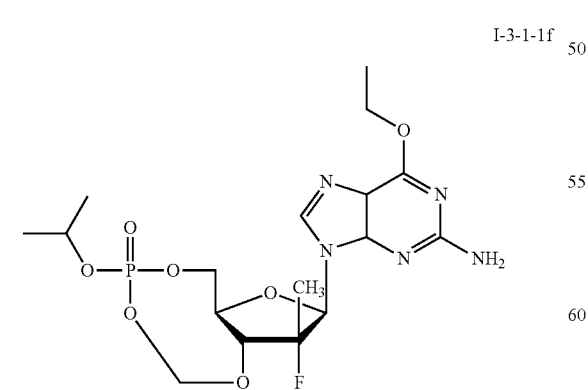
In other embodiments, non-limiting examples of nucleosides that can be derivatized to bc-ProTides shown in Formula I-1 include:
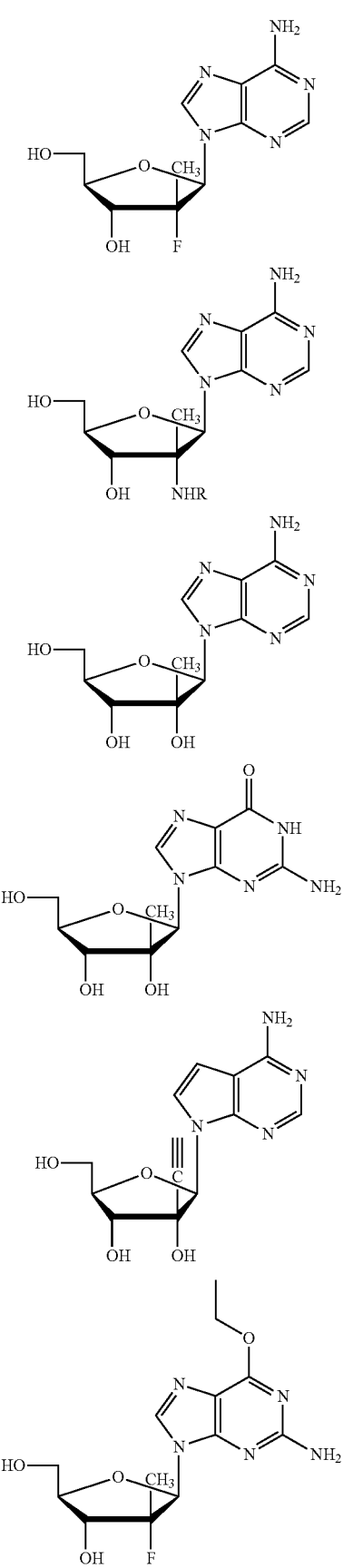

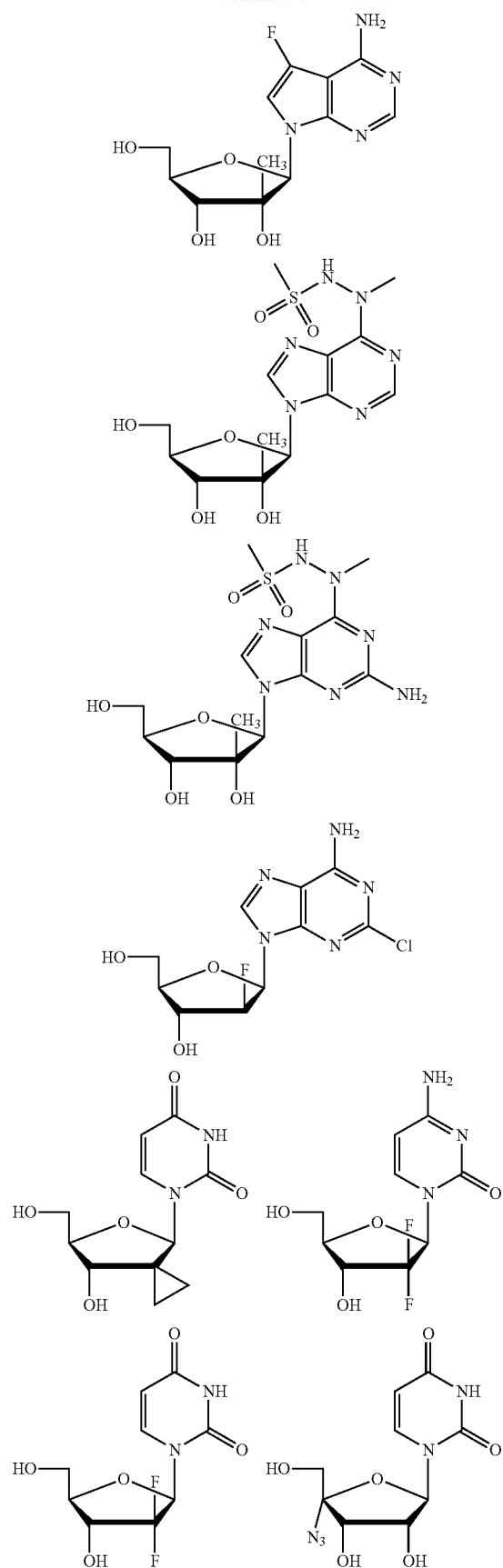
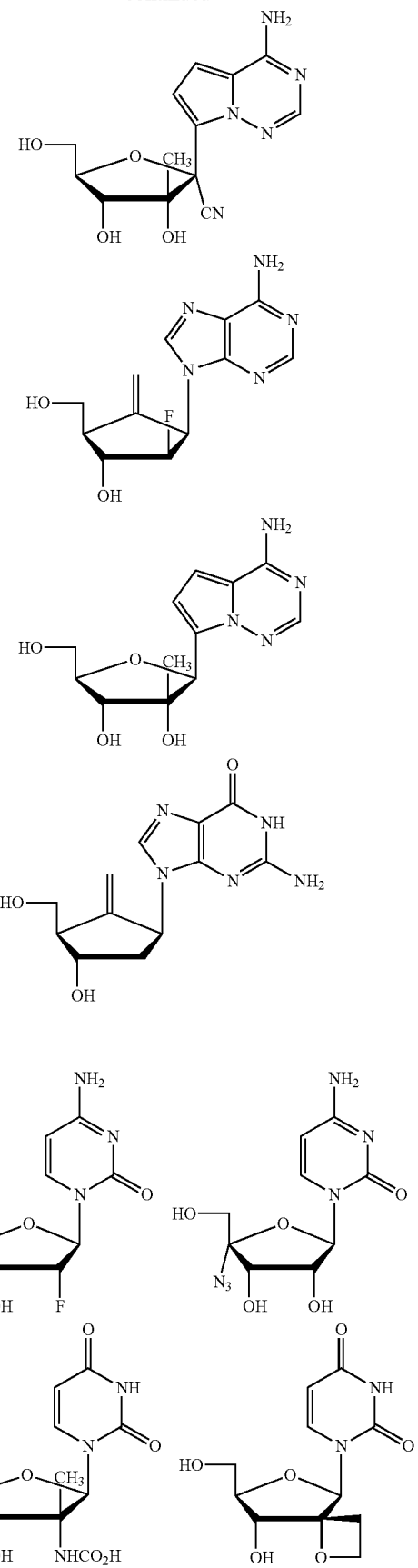

51
-continued
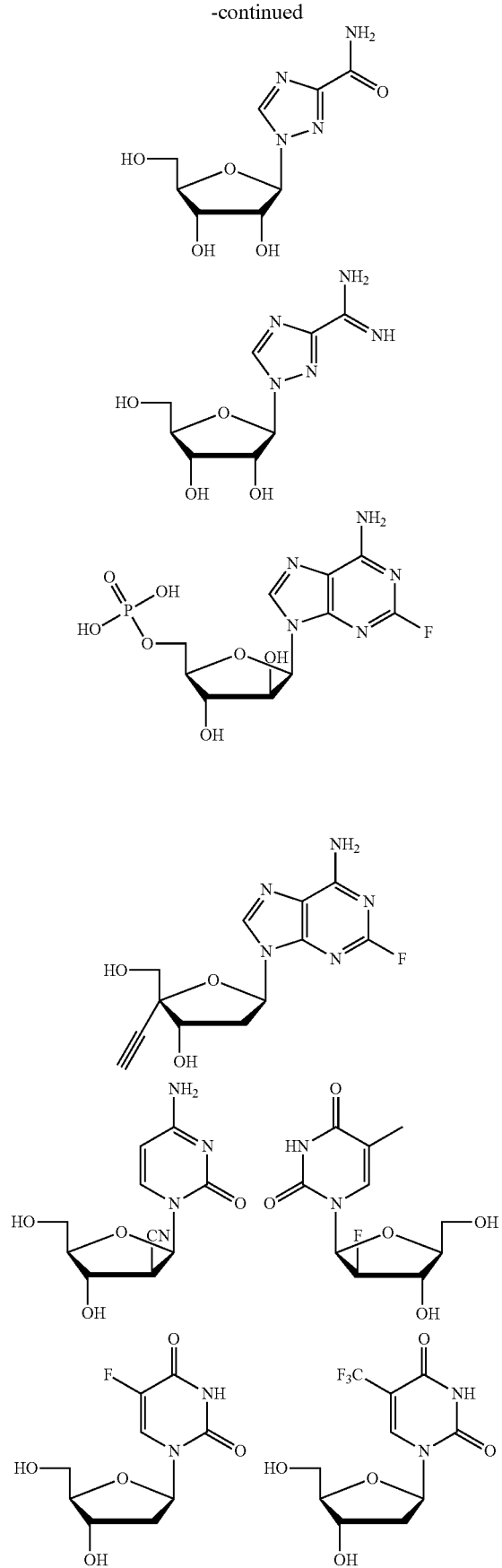
52
-continued
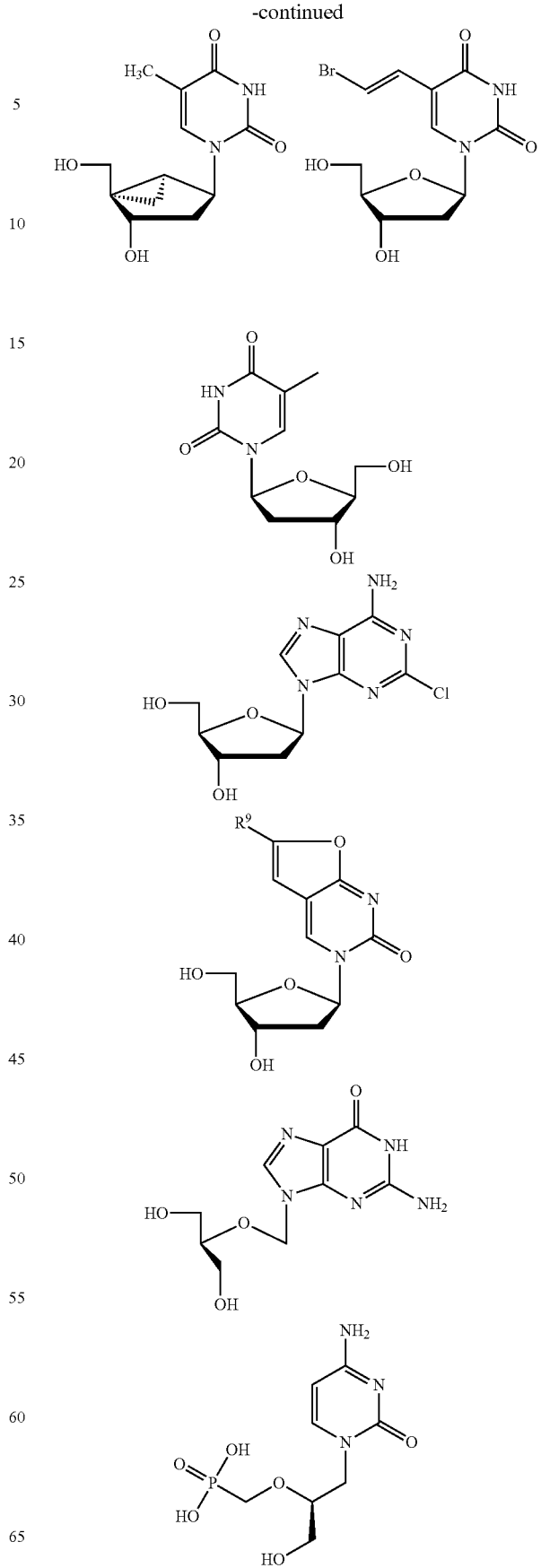

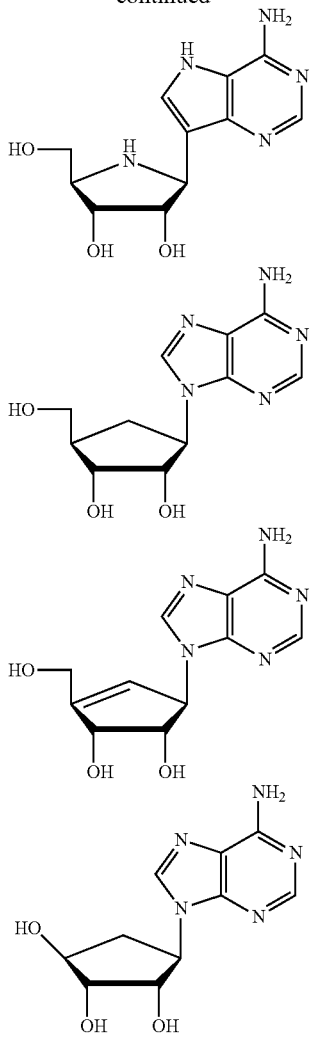

Process for Preparation of Compounds

Another embodiment of this invention represents processes for preparation of these compounds provided herein, which can also be prepared by any other methods apparent to those skilled in the art. Exemplary methods are provided in Scheme I to VII.

In certain embodiments, the compounds provided herein can be prepared by intermolecular cyclization by alkylation, acetal formation, ketal formation, and etc. as provided in Scheme I, wherein $Lg^1$ and $Lg^2$ are leaving groups selected from alkoxyl, halogen, sulfate, and other leaving groups apparent to those skilled in the art. One or more protection steps may be included in the method provided in scheme I.

Scheme I

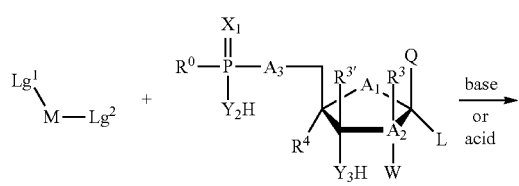

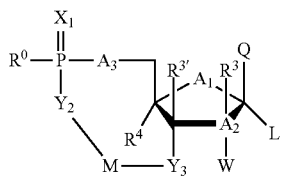

In certain embodiments, the compounds provided herein can be prepared by stepwise intermolecular cyclization via an activation step as provided in Scheme II. Lg can be halogen, or OH, which can be activated as a leaving group by activating agents such as DCC, EDCI, HATU, and others, or known to those of skill in art. $Nu^1$ is OH, SH, or $NHR^{8'}$. $Lg^2$ can be alkylthio and arylthio which can be activated to corresponding sulfates ($Lg^{2'}$). One or more protection and deprotection steps may be included in the method provided in scheme II.

Scheme II

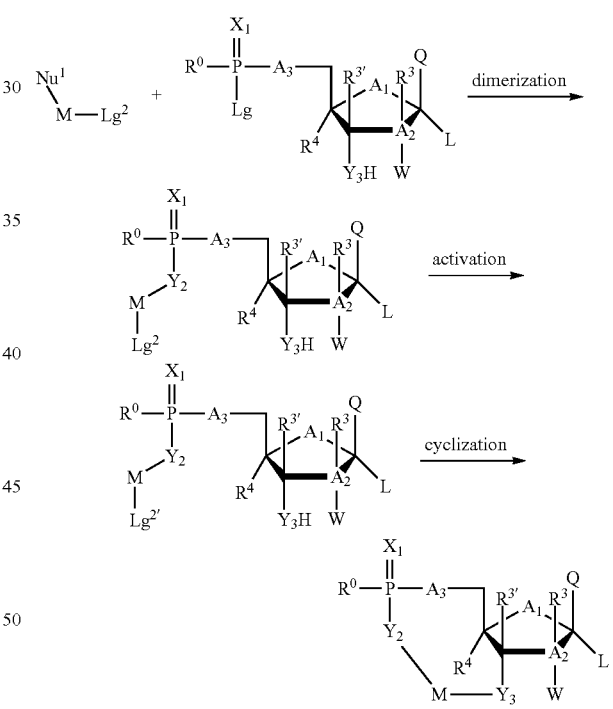

In certain embodiments, the compounds provided herein can be prepared by stepwise intermolecular cyclization via an activation step as provided in Scheme III. $Lg^1$ can be halogen, or OH, which can be activated as a leaving group by activating agents such as sulfonyl halides, and others known to those skilled in the art. $Y_2$ can be O, S, or $NHR^{8'}$. $Y_3$ can be O, S, or $NHR^{8''}$. Lg can be alkylthio and arylthio which can be activated to corresponding sulfates ($Lg^{2'}$). One or more protection and deprotection steps may be included in the method provided in scheme III.

Scheme III

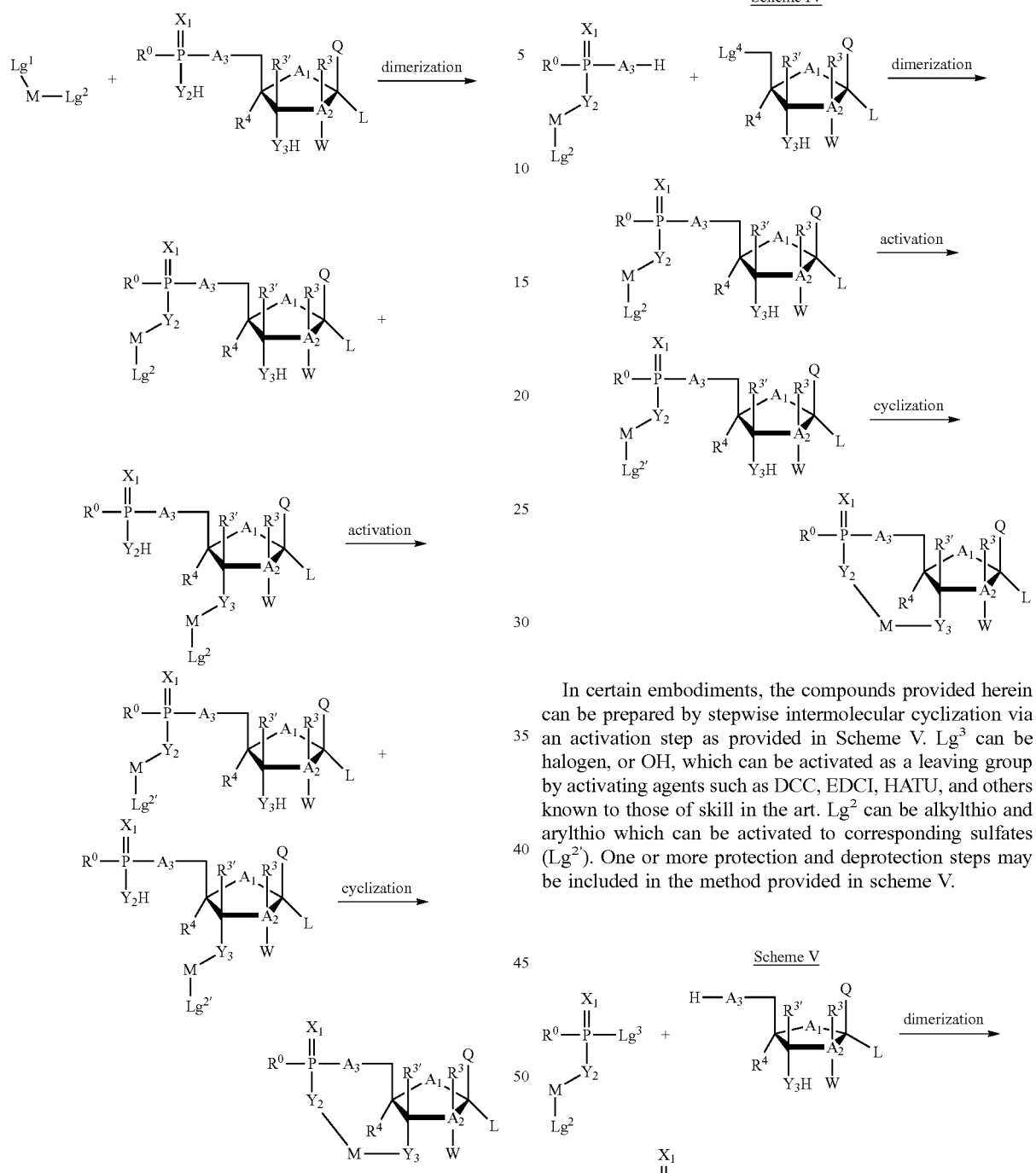

In certain embodiments, the compounds provided herein can be prepared by stepwise intermolecular cyclization via an activation step as provided in Scheme IV. $Lg^4$ can be halogen, or OH, which can be activated as a leaving group such as mesylate, tosylate, triflate and others known to those skilled in the art. $Lg^2$ can be alkylthio and arylthio which can be activated to corresponding sulfates ($Lg^{2'}$). One or more protection and deprotection steps may be included in the method provided in scheme IV.

Scheme IV

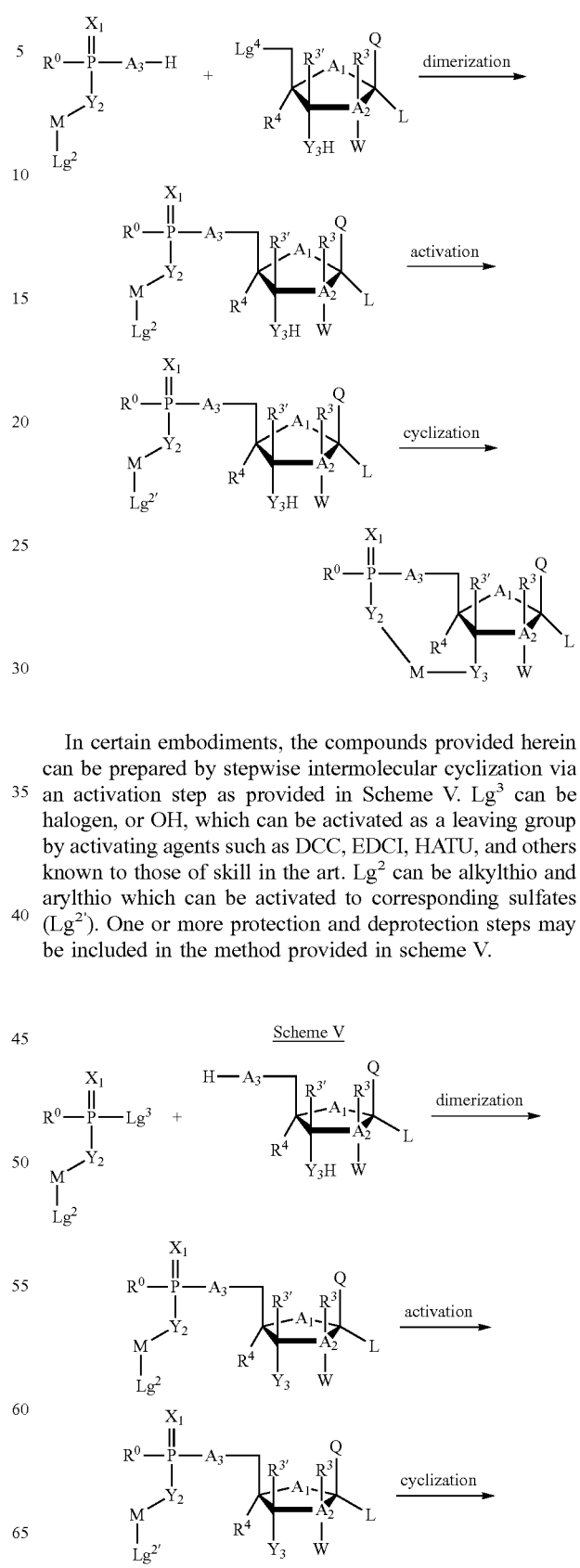

In certain embodiments, the compounds provided herein can be prepared by stepwise intermolecular cyclization via an activation step as provided in Scheme V. $Lg^3$ can be halogen, or OH, which can be activated as a leaving group by activating agents such as DCC, EDCI, HATU, and others known to those of skill in the art. $Lg^2$ can be alkylthio and arylthio which can be activated to corresponding sulfates ($Lg^{2'}$). One or more protection and deprotection steps may be included in the method provided in scheme V.

Scheme V

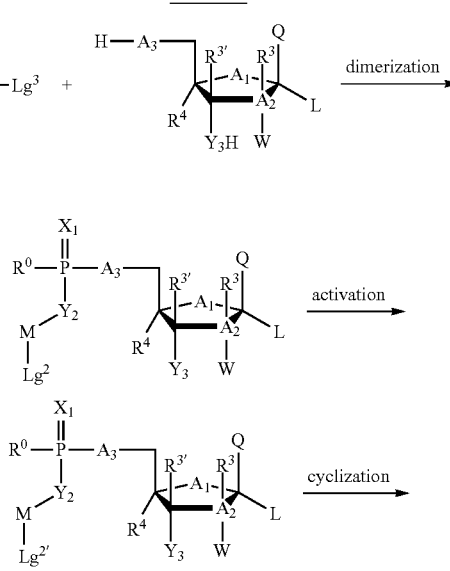

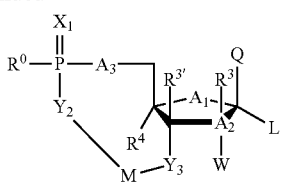

In certain embodiments, the compounds provided herein can be prepared by stepwise intermolecular cyclization via an activation step as provided in Scheme VI. $Lg^3$ can be halogen. $Lg^2$ can be alkoxyl or OH, which can be activated by reagents such as DCC, EDCI, HATU, and others to a leaving group $Lg^{2'}$ known to those of skill in the art. One or more protection and deprotection steps may be included in the method provided in scheme VI.

Scheme VI

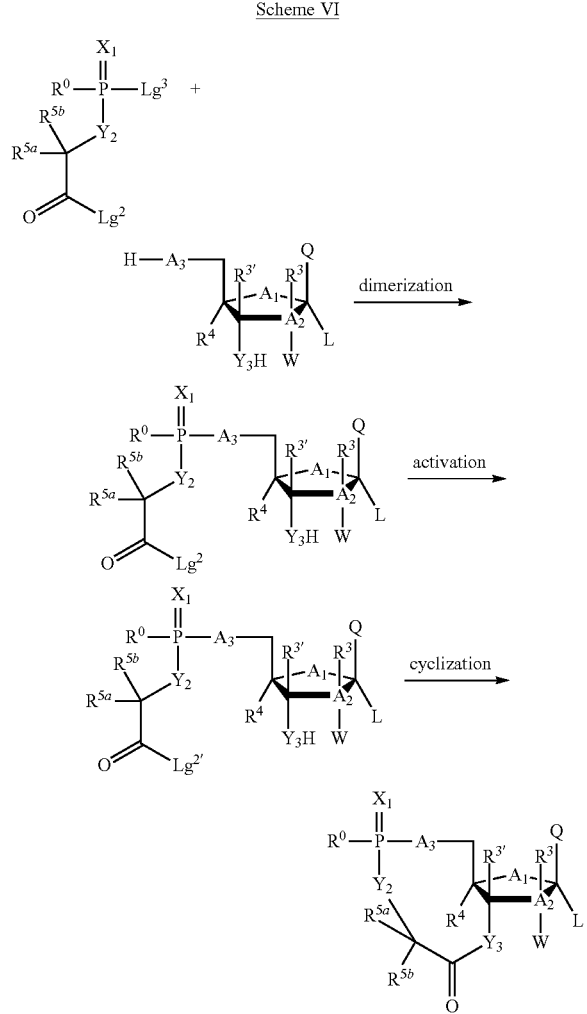

In certain embodiments, the compounds provided herein can be prepared by intermolecular cyclization as provided in Scheme VII. $Lg^2$ and $Lg^3$ can be halogen.

Scheme VII

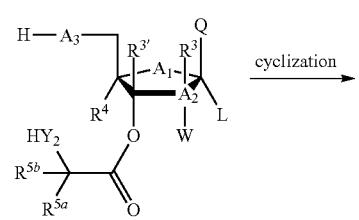

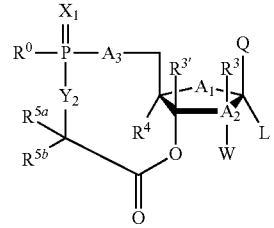

EXAMPLES

The following examples further illustrate embodiments of the disclosed invention, which are not limited by these examples.

Example 1: Compound 1

Preparation of (2S)-isopropyl 2-(((6aR,8R,9R,9aR)-8-(2,4-dioxo-3,4-dihydropyrimidin-1(2H)-yl)-9-fluoro-9-methyl-4-oxidotetrahydro-6H-furo[3,2-f][1,3,5,2]trioxaphosphocin-4-yl)amino)propanoate
(Scheme 1-A to C)

Method A (Scheme 1-A):
Preparation of Intermediate 1-1
In a round bottom flask, disodium p-nitrophenyl phosphate hexahydrate (0.5 mmol, 1 mol/eq) and isopropyl L-valinate hydrochloride (3 mol/eq) are dissolved in a mixture of tert-butanol (9 ml) and H$_2$O (2 ml). A few drops of triethylamine (Et$_3$N) are added to the solution to facilitate dissolution. An appropriate amount of N,N'-dicyclohexyl-carbodiimide (DCC) (3 mol/eq) is dissolved in 1 ml of tert-butanol and is dropwise added to the reaction mixture. The reaction mixture is refluxed carefully for 3-4 h while stirring. The progress of the reaction is monitored by TLC (i-PrOH:NH$_3$:H$_2$O). Upon completion, the reaction mixture is cooled down and the solvent is removed by rotary evaporation. The product is isolated by silica column chromatography to afford intermediate 1-1.

Preparation of Intermediate 1-2
To a solution of intermediate 1-1 (0.5 mmol, 1 mol/eq) in DMF (20 mL) is added chloromethyl methyl sulfide (1.1 mol/eq). The reaction mixture is stirred at 25° C. under N$_2$ for 1 h. The solution is diluted with EtOAc (50 mL) and aqueous HCl solution (1%, 40 mL). The organic layer is separated and washed with H$_2$O (50 mL). Then, it is dried over anhydrous MgSO$_4$, and concentrated under reduced pressure. Purification by silica gel column chromatography (EtOAc/MeOH) affords intermediate 1-2.

Method B (Scheme 1-B):
Preparation of Intermediate 1-3
To a stirred solution of p-nitrophenyl dichlorophosphate (1.00 mol/eq) and isopropyl valinate hydrochloride (1.00 mol/eq) in anhydrous DCM is added, dropwise at −78° C.

under an argon atmosphere, anhydrous TEA (2.00 mol/eq). Following the addition the reaction mixture is stirred at −78° C. for 1 h, then at room temperature for 2 h. Formation of the desired compound is monitored by $^{31}$P NMR. After this period the solvent is removed under reduced pressure and the residue is extracted with dry diethyl ether. The precipitate is filtered under nitrogen and the solution is concentrated to give an oil, which is purified by flash column chromatography (eluting with ethyl acetate/hexanes, 60/40) to give intermediate 1-3.

Preparation of Intermediate 1-1'

To a stirred solution of intermediate 1-3 (1.00 mol/eq) in anhydrous Et$_2$O is added, dropwise at 0° C., 1M tetrabutylammonium hydroxide in H$_2$O (2.00 mol/eq). The reaction mixture is stirred at 0° C. for 1.5 h. Formation of the desired compound is monitored by $^{31}$P NMR. After this period the solvent is removed under reduced pressure and the residue is used for next step.

Preparation of Intermediate 1-2

To a solution of crude intermediate 1-1 or 1-1' (0.5 mmol, 1 mol/eq) in DMF (20 mL) is added chloromethyl methyl sulfide (1.1 mol/eq). The reaction mixture is stirred at 25° C. under N$_2$ for 1 h. The solution is diluted with EtOAc (50 mL) and aqueous HCl solution (1%, 40 mL). The organic layer is separated and washed with H$_2$O (50 mL). Then, it is dried over anhydrous MgSO$_4$, and concentrated under reduced pressure. Purification by silica gel column chromatography (EtOAc/MeOH, 6:4) affords intermediate 1-2.

Preparation of Intermediate 1-5

To a solution of 1-((2R,3R,4R,5R)-3-fluoro-4-hydroxy-5-(hydroxymethyl)-3-methyltetrahydrofuran-2-yl)pyrimidine-2,4(1H,3H)-dione (0.5 mmol, 1 mol/eq) in anhydrous THF (1.5 mL) is added 1.0 M t-butyl magnesium chloride (1.05 mmol, 2.1 mol/eq) at rt. The resulting mixture is stirred at rt for 0.5 h, and intermediate 1-2 (1.0 mmol) in THF (1.5 mL) is added dropwise. The reaction mixture is stirred for 2 h, and then quenched by adding saturated aqueous ammonium chloride (20 mL), and extracted twice with EtOAc (20 mL×2). The organic layers are combined, dried from MgSO$_4$, and concentrated till dryness to give a residue, which is separated by silica gel chromatography to give intermediate 1-5.

Alternatively 3'-OH can be transiently protected by Cbz, and then deprotected before oxidation/cyclization by hydrogenation.

Preparation of Compound 1

Condition A: Intermediate 1-5 (10 mmol, 1.0 mol/eq) is dissolved in anhydrous dichloromethane (200 mL) containing triethylamine (2.2 mol/eq) at room temperature, and then predried molecular sieves (3 Å) is added. The mixture is stirred in an ice-bath. A solution of sulfuryl chloride (1 mol/eq) in anhydrous dichloromethane is added dropwise to the reaction mixture during 30 minutes. The ice-bath is removed and the reaction mixture is stirred further till completion as shown by TLC analysis. The solid is removed by filtration, and the filtrate is washed with saturated aqueous sodium bicarbonate solution, followed by brine, and then dried over Na$_2$SO$_4$, filtered, concentrated. The obtained crude mixture is purified by silica gel column chromatography to give the compound 1.

Condition B: Intermediate 1-5 (10 mmol, 1.0 mol/eq) is dissolved in anhydrous 1,2-dichloroethane (200 mL) containing triethylamine (2.2 mol/eq). The solution is cooled in an ice-bath. Under N$_2$ atmosphere, bromine (1.1 eq.) is added very slowly. Stirring is continued at room temperature for additional 1 h. The reaction mixture is poured slowly into saturated aqueous sodium bicarbonate solution (50 mL) and separated. The organic phase is washed with water (3×100 mL), brine (100 mL) and dried over Na$_2$SO$_4$, filtered, concentrated. The obtained crude mixture is purified by silica gel column chromatography to give compound 1.

Condition C: To a cooled mixture of thoroughly dried intermediate 1-5 (5.00 mmol) and powdered 5 Å molecular sieves (~200 mg) in anhydrous 1,2-dichloroethane (DCE, 50 mL) at 0° C. is added a freshly prepared solution of N-iodosuccinimide (NIS, 1.12 g, 5.00 mmol) and fresh trifluoromethanesulfonic acid (TfOH, 64 µL, 0.72 mmol) in DCE/Et$_2$O (1:1 v/v, 25 mL). The addition of more TfOH (1 or 2×0.72 mmol) may be necessary to complete the reaction. After filtration of the suspension, the filtrate is diluted with CH$_2$Cl$_2$ (150 mL) and washed, sequentially, with aqueous 1 M sodium bisulfite (100 mL) and a saturated aqueous solution of NaHCO$_3$ (100 mL). The organic layer is dried over anhydrous Na$_2$SO$_4$ and then filtered. The filtrate is evaporated till dryness to give a residue, and is purified by silica gel column chromatography to give compound 1.

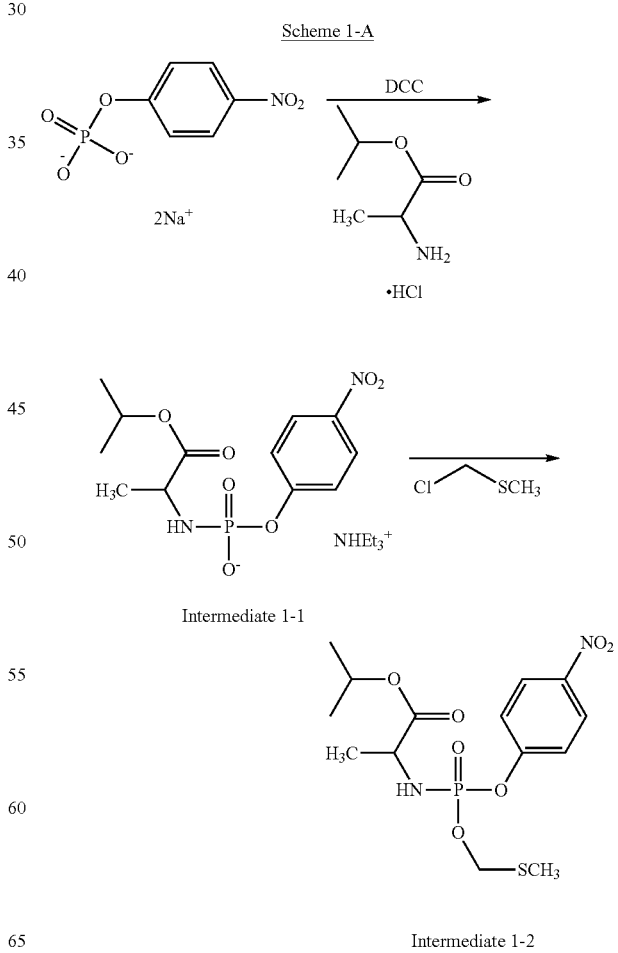

Scheme 1-A

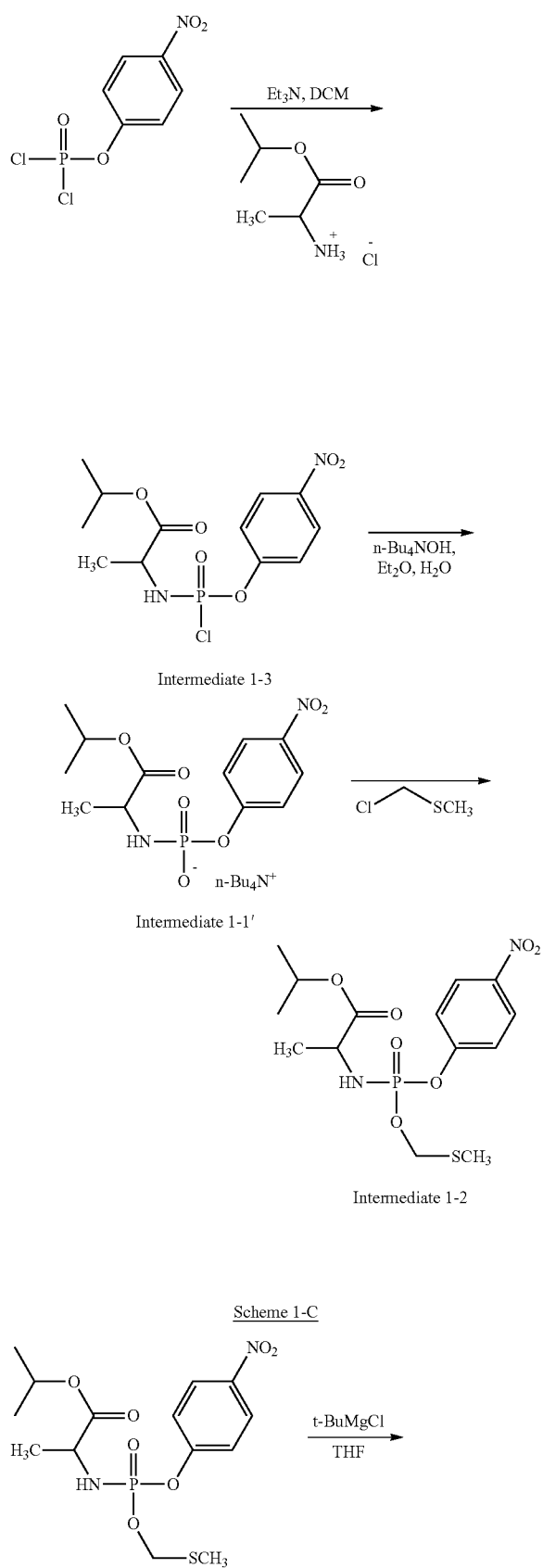

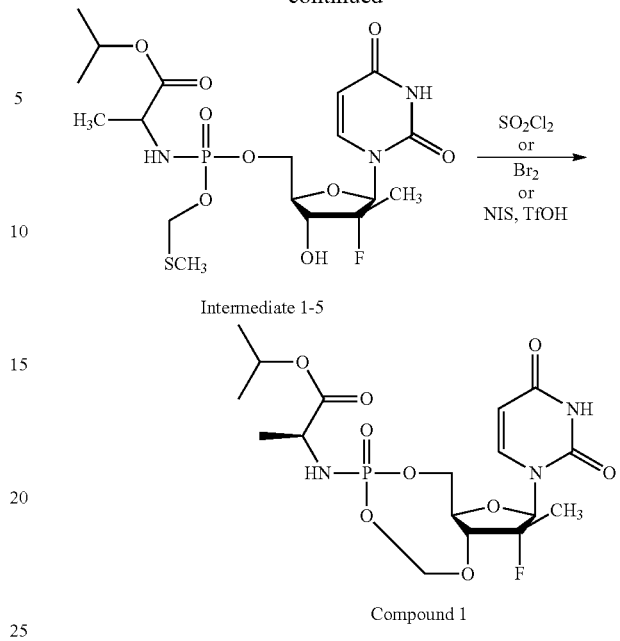

Intermediate 1-5

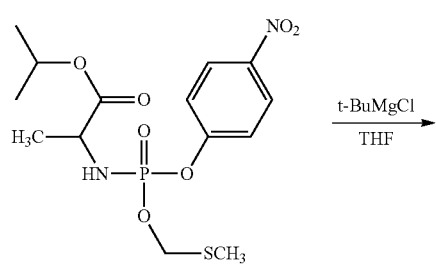

Compound 1

Example 2: Compound 2

Preparation of isopropyl 2-((((6aR,8R,9R,9aR)-8-(6-amino-9H-purin-9-yl)-9-hydroxy-9-methyl-4-oxido-tetrahydro-6H-furo[3,2-f][1,3,5,2]trioxaphosphocin-4-yl)amino)propanoate (Scheme 2-A and B)

Method A:
Preparation of Intermediate 2-1

In a dry flask, to N-(9-((2R,3R,4R,5R)-3,4-dihydroxy-5-(hydroxymethyl)-3-methyltetrahydrofuran-2-yl)-9H-purin-6-yl)benzamide (1 mmol, 1 mol/eq) in anhydrous DMF (5 mL) stirred at 0° C. under nitrogen is added di-t-butylsilyl ditriflate (1.1 mol/eq) dropwise. The resulting mixture is stirred at the same temperature till completion as showed by TLC analysis. The reaction is diluted with EtOAc (50 mL), and washed with H₂O (50 mL×3). Then, it is dried over anhydrous MgSO₄, and concentrated under reduced pressure. Purification by silica gel column chromatography (DCM/MeOH) affords intermediate 2-1.

Preparation of Intermediate 2-2

In a dry flask, intermediate 2-1 (1 mmol, 1 mol/eq) is dissolved in DCM (10 mL), and then DIPEA (1.4 mol/eq), catalytic amount of tetra-t-butylammonium iodide (0.05 mol/eq), and benzyloxymethyl chloride (1.2 mol/eq) are added. The reaction is stirred under reflux till completion as showed by TLC analysis. The reaction is then cooled to −15° C. (HF)x.pyridine (3.7 mmol) (diluted (6 x) in pyridine at 0° C.) is slowly added. The reaction is stirred under nitrogen till completion as showed by TLC analysis. Volatiles are evaporated under vacuum to give a residue. Purification by silica gel column chromatography (DCM/MeOH) affords intermediate 2-2.

Preparation of Intermediate 2-3

To a solution of intermediate 2-2 (1 mmol, 1 mol/eq) in trimethyl phosphate (3 mL) at 0° C. under nitrogen is added dropwise P(O)Cl₃ (2 mol/eq). The mixture is stirred at this temperature till near completion as indicated by TLC analysis (i-PrOH/H₂O/NH₃—H₂O, 6:3:1). The reaction is quenched by addition of 0.2 M triethylammonium bicarbonate buffer (pH 7.5, 10 mL). The resulting solution is stirred at 0° C. for 1 h, then warmed up to rt, and washed with EtOAc (×3). The aqueous solution is lyophilized till dryness to give intermediate 2-3 as a slightly colored foam.

Preparation of Intermediate 2-4

In a two neck flask, intermediate 2-3 (1 mol/eq) and isopropyl L-valinate hydrochloride (3 mol/eq) are dissolved in a mixture of tert-butanol (9 ml) and H$_2$O (2 ml). A few drops of triethylamine (Et$_3$N) are added to the solution to facilitate dissolution. An appropriate amount of N,N'-dicyclohexylcarbodiimide (DCC) (3 mol/eq) is dissolved in 1 ml of tert-butanol and is dropwise added to the reaction mixture. The reaction mixture is refluxed while stirring. The progress of the reaction is monitored by TLC (i-PrOH:NH$_3$:H$_2$O). Upon completion, the reaction mixture is cooled down and the solvent is removed by rotary evaporation. The product is isolated by silica column chromatography to afford intermediate 2-4.

Preparation of Intermediate 2-5

To a solution of intermediate 2-4 (0.5 mmol, 1 mol/eq) in DMF (100 mL) are added potassium carbonate (15 mmol, 30 mol/eq) and dibromomethane (7.2 mmol, 14.4 mol/eq), and the resulting solution is stirred at rt for 15 h. After removing the volatiles under reduced pressure, the residue is dissolved in DCM, and washed with saturated aqueous sodium bicarbonate solution and brine. The organic layers is then dried from anhydrous magnesium sulfate, and concentrated till dryness to give a residue, which is separated by a silica gel column to give intermediate 2-5.

Preparation of Compound 2

Intermediate 2-5 (0.1 mmol, 1 mol/eq) is dissolved in EtOAc-EtOH (1:1, 50 mL) in a dried flask, 10% wet palladium-carbon is then added. The mixture is purged with nitrogen twice, and hydrogenated (with a balloon filled with H$_2$) at ambient temperature. After completion (monitored by TLC analysis), the solid is removed by filtration over a Celite layer. The filtrate is concentrated by evaporation under vacuum to provide the crude product. Column chromatography on silica gel (MeOH/DCM) affords compound 2.

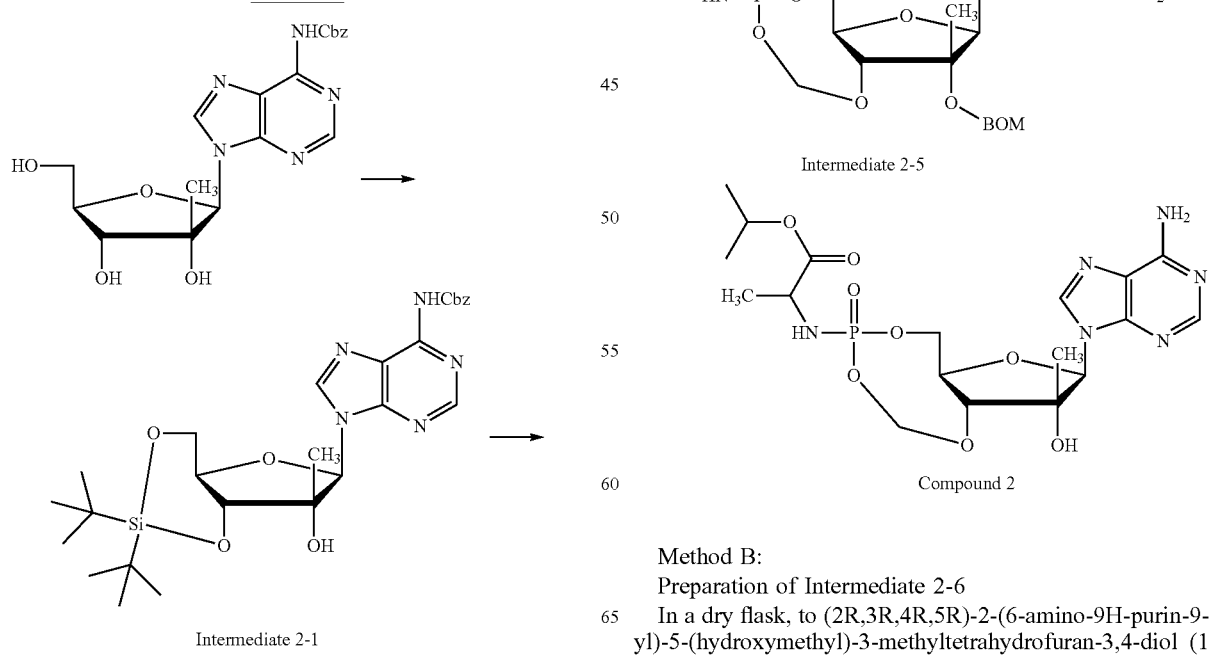

Method B:

Preparation of Intermediate 2-6

In a dry flask, to (2R,3R,4R,5R)-2-(6-amino-9H-purin-9-yl)-5-(hydroxymethyl)-3-methyltetrahydrofuran-3,4-diol (1 mmol, 1 mol/eq) in anhydrous DMF (5 mL) stirred at 0° C.

under nitrogen is added di-t-butylsilyl ditriflate (1.1 mol/eq) dropwise. The resulting mixture is stirred at the same temperature till completion as shown by TLC analysis. To the reaction is added imidazole (5 mol/eq) at 0° C., and the resulting mixture is stirred for additional 5 min, and then warmed up to rt. TBSCl (1.2 mol/eq) is added, the reaction is then stirred at 60° C. under nitrogen till completion as shown by TLC analysis. The reaction is diluted with EtOAc (50 mL) and H₂O (50 mL). The organic layer is collected and washed with H₂O (50 mL×2). Then, it is dried over anhydrous MgSO₄, and concentrated under reduced pressure. Purification by silica gel column chromatography (DCM/MeOH) affords intermediate 2-6.

Preparation of Intermediate 2-7

Intermediate 2-6 is selectively deprotected at 3' and 5' by treatment with (HF)$_x$.pyridine. Intermediate 2-6 (0.74 mmol, 1 mol/eq) is dissolved in DCM, and stirred at −15° C. (HF)$_x$.pyridine (3.7 mmol, 5 mol/eq) diluted (6 x) in pyridine at 0° C. is slowly added. The reaction is stirred under nitrogen till completion as shown by TLC analysis. The reaction mixture is diluted by addition of DCM (50 mL), washed with H₂O (50 mL). Then, it is dried over anhydrous MgSO₄, and concentrated under reduced pressure. Purification by silica gel column chromatography (DCM/MeOH) affords intermediate 2-7.

Preparation of Intermediate 2-8

To a solution of intermediate 2-7 (1 mmol, 1 mol/eq) in trimethyl phosphate (3 mL) at 0° C. under nitrogen is added dropwise P(O)Cl₃ (2 mol/eq). The mixture is stirred at this temperature till near completion as indicated by TLC analysis (i-PrOH/H₂O/NH₃—H₂O, 6:3:1). To this mixture is then added L-valanyl isopropyl ester hydrochloride (1.5 mol/eq) in CH₃CN (4 mL), followed by addition of DIPEA (10 mol/eq). The reaction is stirred at 0° C. and then at rt for 1 h. Water (0.6 mL) is added, and the reaction mixture is stirred for another 15 min. The reaction is concentrated till dryness as a residue.

The above residue is dissolved in DMF (10 mL) is added chloromethyl methyl sulfide (1.1 mol/eq) and DIPEA (7 mol/eq). The reaction mixture is stirred at 25° C. under N₂ for 1 h. The solution is diluted with EtOAc (50 mL) and aqueous HCl solution (1%, 40 mL). The organic layer is separated and washed with H₂O (50 mL). Then, it is dried over anhydrous MgSO₄, and concentrated under reduced pressure. Purification by silica gel column chromatography (EtOAc/MeOH) affords intermediate 2-8.

Preparation of Intermediate 2-9

Intermediate 2-8 (1 mmol, 1.0 mol/eq) is dissolved in anhydrous 1,2-dichloroethane (20 mL) containing triethylamine (3.0 mol/eq). The solution is cooled in an ice-bath. Under N₂ atmosphere, bromine (1.1 eq.) is added very slowly. Stirring is continued at room temperature for additional 1 h. The reaction mixture is poured slowly into saturated aqueous sodium bicarbonate solution (50 mL) and separated. The organic phase is washed with water (50 mL×3), brine (50 mL) and dried over Na₂SO₄, filtered, concentrated. The obtained crude mixture is purified by silica gel column chromatography to give intermediate 2-9.

Preparation of Compound 2

Intermediate 2-9 (1 mol/eq) is added to a dried round bottom flask equipped with a stirring bar and 1 M tetrabutylammonium fluoride (TBAF) in THF (2 mol/eq) buffered with a mixture of acetic acid (2.6 mol/eq) and acetic anhydride (2.6 mol/eq). The reaction is monitored by TLC until deprotection is complete. The reaction is then quenched with water (3 mol/eq). The reaction mixture is concentrated till dryness under vacuum to give a crude product, which is purified by flash chromatography to afford compound 2.

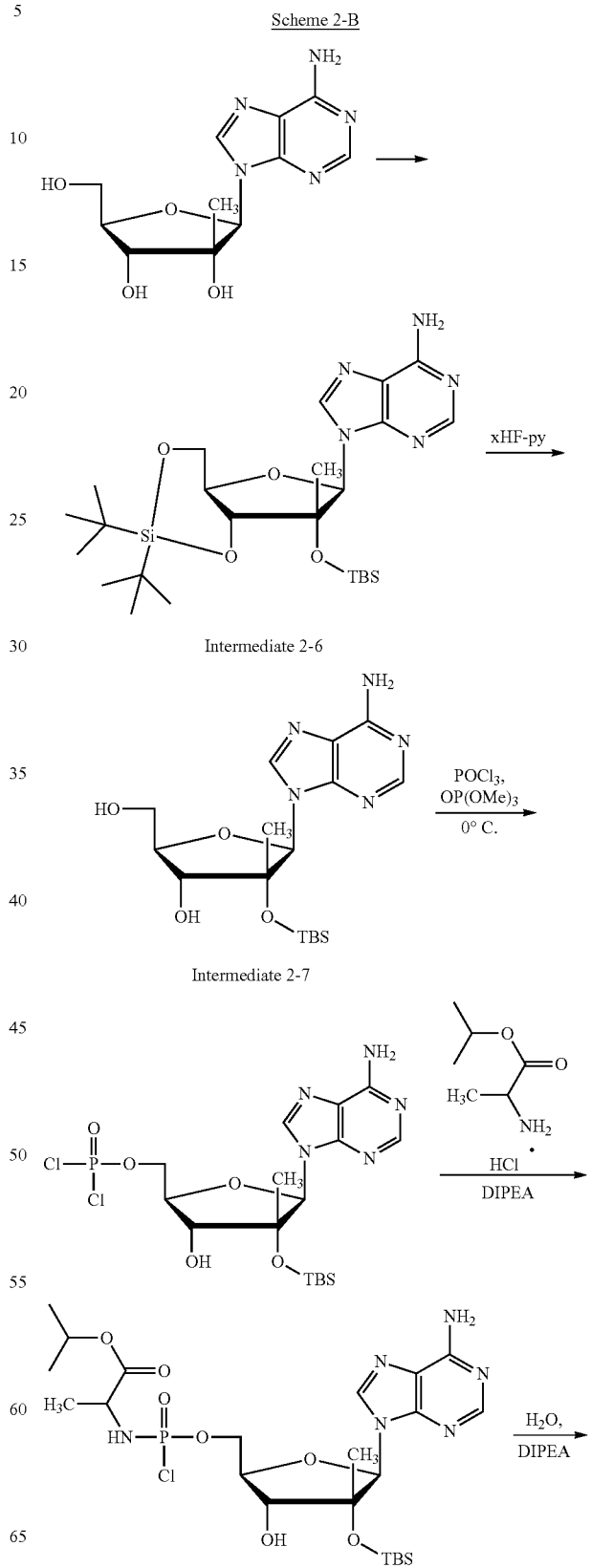

Scheme 2-B

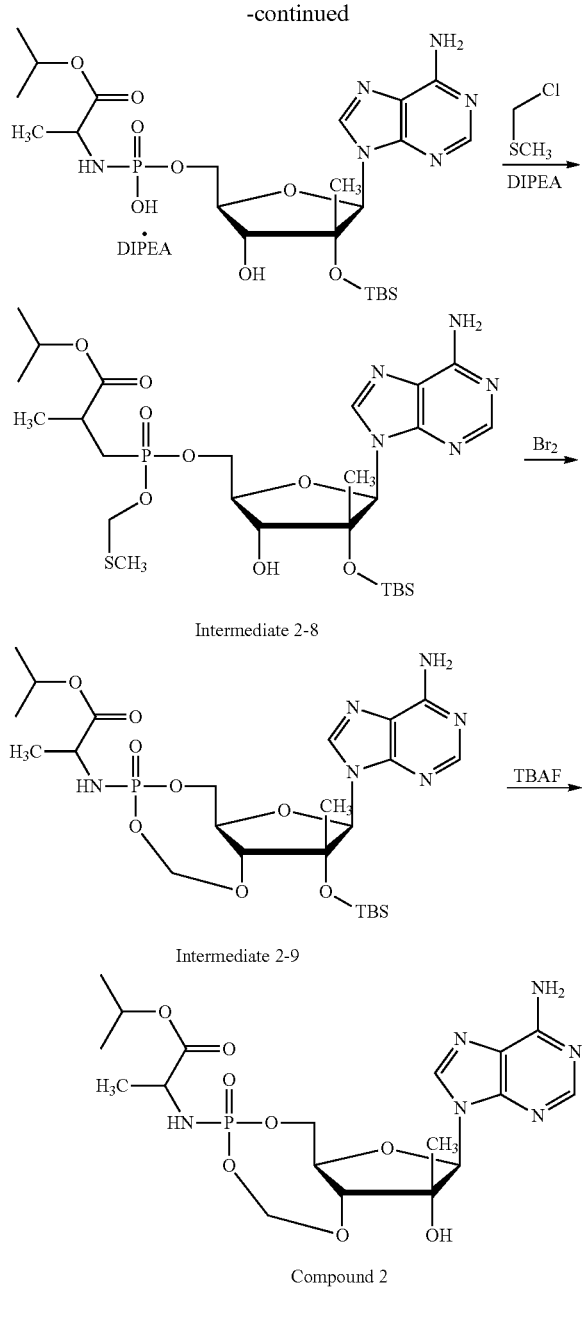

Intermediate 2-8

Intermediate 2-9

Compound 2 progress of the reaction is monitored by TLC (i-PrOH:NH₃:H₂O). Upon near completion, the reaction mixture is cooled down and the solvent is removed by rotary evaporation to provide crude intermediate 3-1.

Preparation of Compound 3

To a round bottom flask containing intermediate 3-1 (1 mmol, 1 mol/eq) are added 2,2-dimethoxypropane (30 mL), toluene (30 ml), and PPTS.H₂O (3 mol/eq), and the mixture is stirred under reflux under N₂. The reaction is monitored by TLC analysis, and concentrated till dryness upon near completion. Silica gel column chromatography of the crude reaction product provided compound 3.

Scheme 3

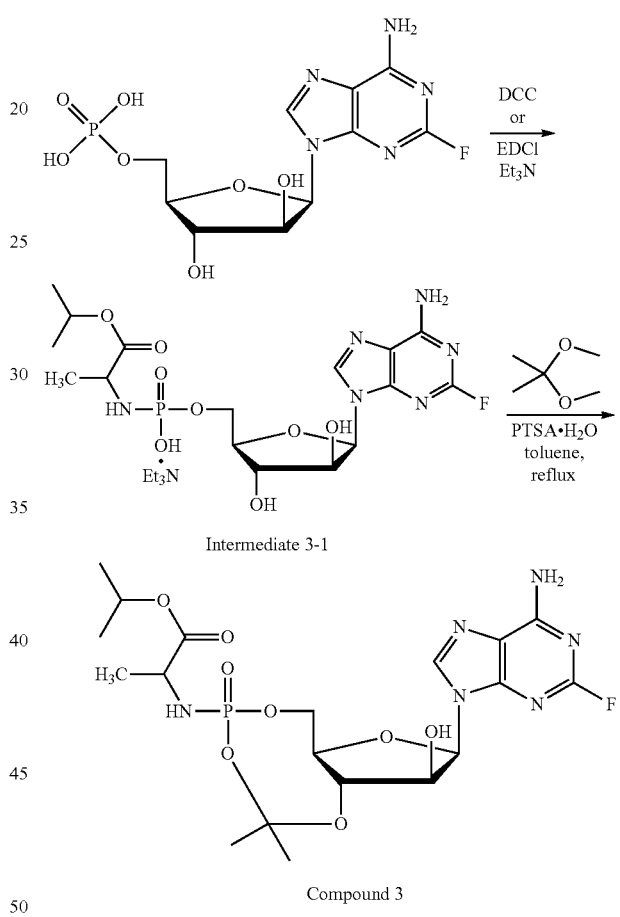

Intermediate 3-1

Compound 3

Example 3: Compound 3

Preparation of isopropyl 2-((((6aR,8R,9S,9aS)-8-(6-amino-2-fluoro-9H-purin-9-yl)-9-hydroxy-2,2-dimethyl-4-oxidotetrahydro-6H-furo[3,2-f][1,3,5,2]trioxaphosphocin-4-yl)amino)propanoate (Scheme 3)

Preparation of Intermediate 3-1

In a two neck flask, fludarabine phosphate (0.5 mmol, 1 mol/eq) and isopropyl L-valinate hydrochloride (3 mol/eq) are dissolved in a mixture of tert-butanol (9 ml) and H₂O (2 ml). Triethylamine (10 mol/eq) are added to the mixture to facilitate dissolution. An appropriate amount of N,N'-dicyclohexylcarbodiimide (DCC) (3 mol/eq) is dissolved in 1 ml of tert-butanol and is dropwise added to the reaction mixture. The reaction mixture is refluxed while stirring. The Example 4: Compound 4

Preparation of (2S)-isopropyl 2-((((6aR,8R,9aR)-8-(4-amino-2-oxopyrimidin-1(2H)-yl)-9,9-difluoro-4-oxidotetrahydro-6H-furo[3,2-f][1,3,5,2]trioxaphosphocin-4-yl)amino)propanoate (Scheme 4)

Preparation of Intermediate 4-1

To gemcitabine hydrochloride (1 mmol, 1 mol/eq) in anhydrous pyridine (10 mL) stirred at 0° C. under nitrogen are added t-butyldimethylsilyl chloride (1.1 mol/eq) and imidazole (1.5 mol/eq). The reaction mixture is stirred at rt and the reaction progress is monitored by TLC analysis. Upon completion, methanol (8 mL) is added, and the reaction is further stirred for 1 h. Volatiles of the reaction are then evaporated under vacuum, and the residue is separated by silica gel column chromatography (EtOAc/hexanes) to provide 5'-O-silylated gemcitabine.

This protected nucleoside is then dissolved in DCM (20 mL), and to the resulting mixture are added DMAP (3 mol/eq) and CbzCl (2.5 mol/eq) at 0° C. under nitrogen. Upon completion (monitored by TLC analysis), the reaction mixture is diluted by addition of DCM (100 mL), and washed with 1.0 M HCl aqueous solution and then water. The organic layer is collected, dried over anhydrous MgSO$_4$, and concentrated till dryness. The residue is separated by silica gel column chromatography (EtOAc/hexanes) to provide intermediate 4-1.

Preparation of Intermediate 4-2

To a solution of intermediate 4-1 (1 mmol, 1 mol/eq) in anhydrous THF (10 mL) stirred at 0° C. under nitrogen is added triethylamine hydrofluoride (6 mol/eq). The reaction is then warmed up to rt, and continued till completion (as monitored by TLC analysis). Volatiles are evaporated under vacuum, and the residue is dissolved in EtOAc (50 mL), washed with cold sodium bicarbonate aqueous solution (30 mL), brine (30 mL), and dried over anhydrous MgSO$_4$ and filtered. The filtrate is concentrated under vacuum till dryness, and the residue is separated by silica gel column chromatography (methanol/DCM) to provide intermediate 4-2.

Preparation of Intermediate 4-3

To intermediate 4-2 (1 mmol, 1 mol/eq) and DBU (2.4 mol/eq) in anhydrous acetonitrile (20 mL) stirred at 0° C. under nitrogen is slowly added intermediate 1-2 (1.2 mol/eq) dissolved in DCM (20 mL). Upon completion as indicated by TLC analysis, volatiles are evaporated in vacuo and the residue is purified by silica gel column chromatography (0 to 5% MeOH/DCM) to afford intermediate 4-3.

Preparation of Intermediate 4-4

Intermediate 4-3 (0.5 mmol, 1 mol/eq) is dissolved in EtOAc-EtOH (1:1, 50 mL) in a dried flask, 10% wet palladium-carbon is then added. The mixture is purged with nitrogen twice, and hydrogenated (with a balloon filled with H$_2$) at ambient temperature. After completion (monitored by TLC analysis), the solid is removed by filtration. The filtrate is concentrated by evaporation under vacuum to provide the crude product. Column chromatography on silica gel (MeOH/DCM) affords intermediate 4-4.

Preparation of Compound 4

Intermediate 4-4 (1 mmol, 1.0 mol/eq) is dissolved in anhydrous 1,2-dichloroethane (20 mL) containing triethylamine (2.2 mol/eq). The solution is cooled in an ice-water bath. Under N$_2$ atmosphere, bromine (1.1 mol/eq) is added very slowly. Stirring is continued at room temperature for additional 1 hour. The reaction mixture is poured slowly into saturated aqueous sodium bicarbonate solution (10 mL) and separated. The organic phase is washed with water (20 mL×3), then brine (20 mL), and dried over Na$_2$SO$_4$, filtered, and concentrated till dryness. The obtained crude mixture is purified by silica gel column chromatography to give the compound 4.

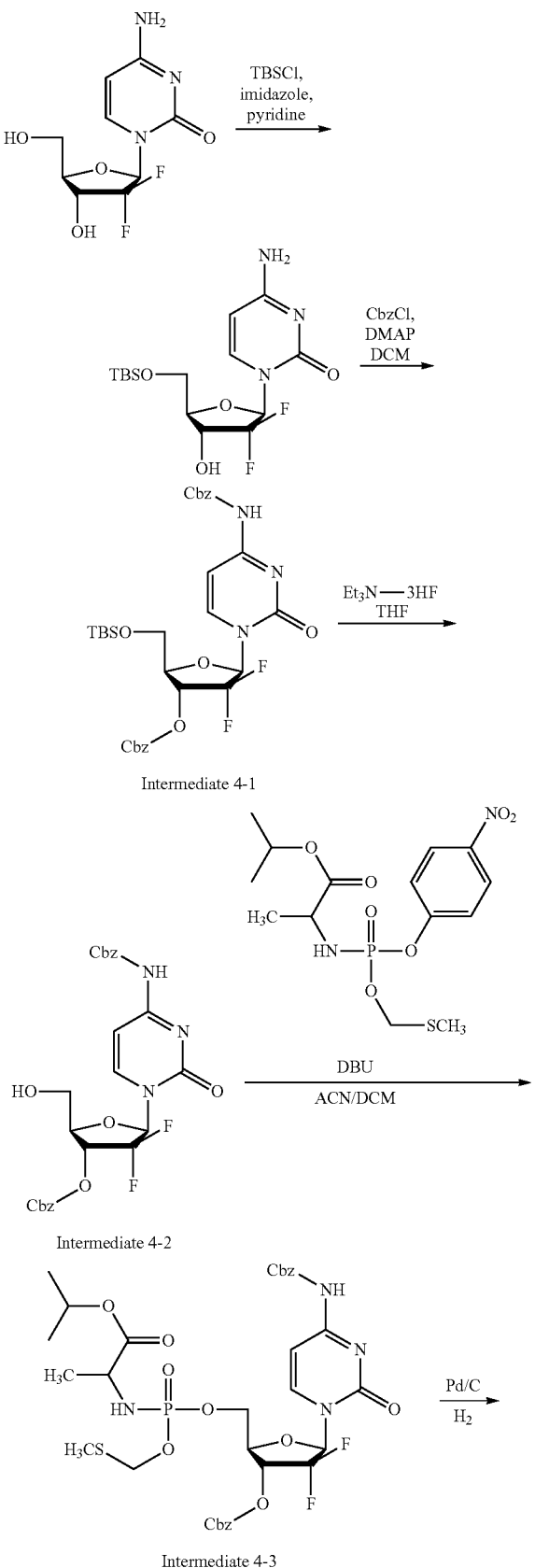

Scheme 4

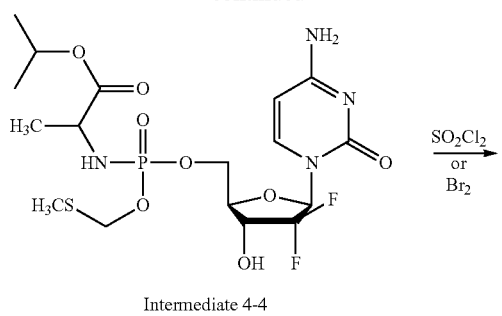

Intermediate 4-4

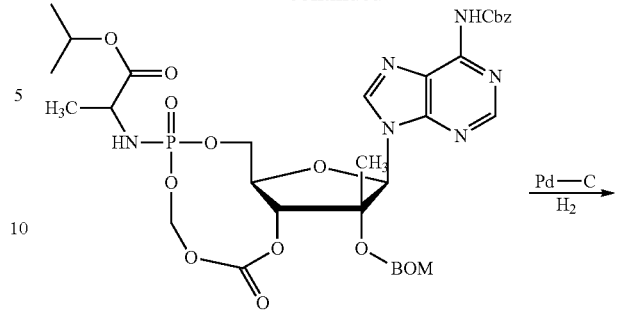

Intermediate 5-1

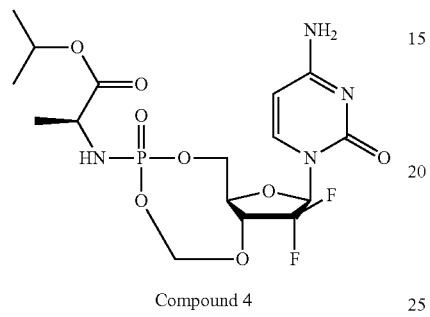

Compound 4

Example 5: Compound 5

Preparation of isopropyl 2-(((8aR,10R,11R,11aR)-10-(6-amino-9H-purin-9-yl)-11-hydroxy-11-methyl-6-oxido-2-oxotetrahydro-8H-furo[3,2-h][1,3,5,7,2]tetraoxaphosphecin-6-yl)amino)propanoatee (Scheme 5)

Intermediate 5-1 can be prepared from intermediate 2-4. Cleavage of Cbz and BOM by hydrogenation affords compound 5 (Scheme 5).

Scheme 5

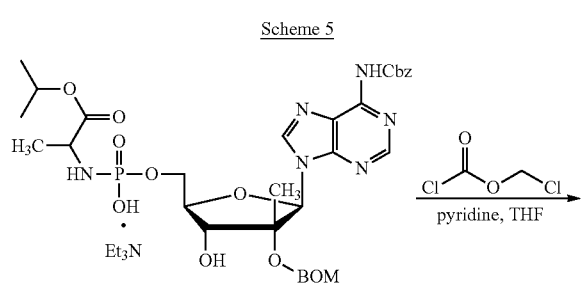

Intermediate 2-4

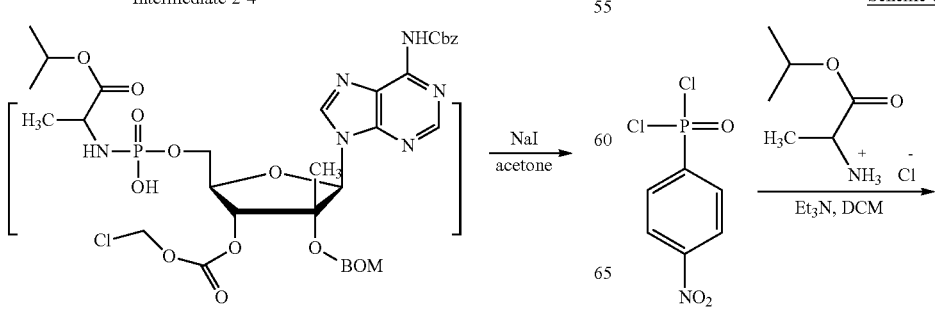

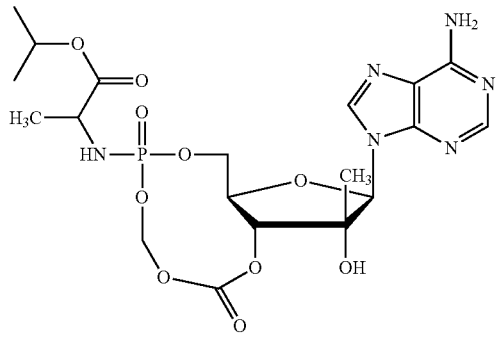

Compound 5

Example 6: Compound 6

Preparation of isopropyl 2-(((7aR,9R,10R,10aR)-9-(2,4-dioxo-3,4-dihydropyrimidin-1(2H)-yl)-10-fluoro-10-methyl-5-oxido-2-oxohexahydro-2H-furo[3,2-g][1,6,3,2]dioxazaphosphonin-5(9H)-yl)amino)acetate (Scheme 6 A-C)

Intermediate 6-3 can be prepared by a general method similar to that for intermediate 4-4 using Cbz as a transient global protecting group for a nucleoside. Lactonization by intramolecular transesterification affords compound 6 (Scheme 6-A).

Scheme 6-A

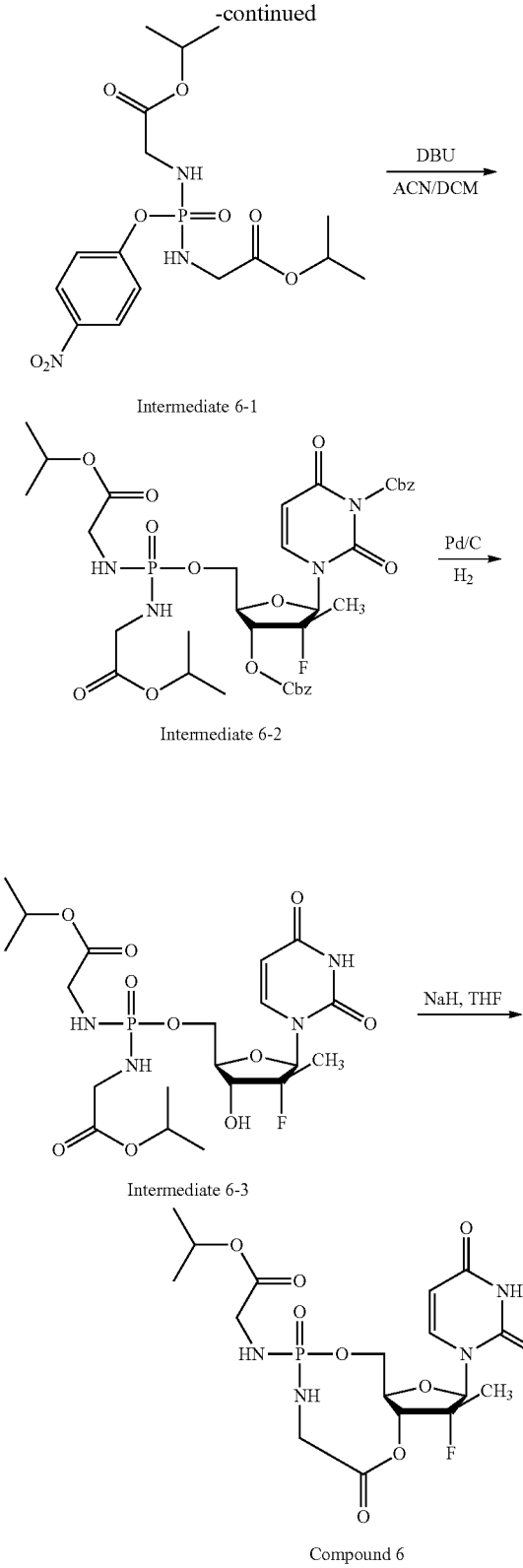

Intermediate 6-1

Intermediate 6-2

Intermediate 6-3

Compound 6

Alternatively, 3'-O-aminoacyl can be installed at early stage, and compound 6 can be synthesized by phosphorylation and then intramolecular phosphoramidate formation (Scheme 6-B), or by one pot phosphorylation and phosphoramidate formation (Scheme 6-C).

Scheme 6-B

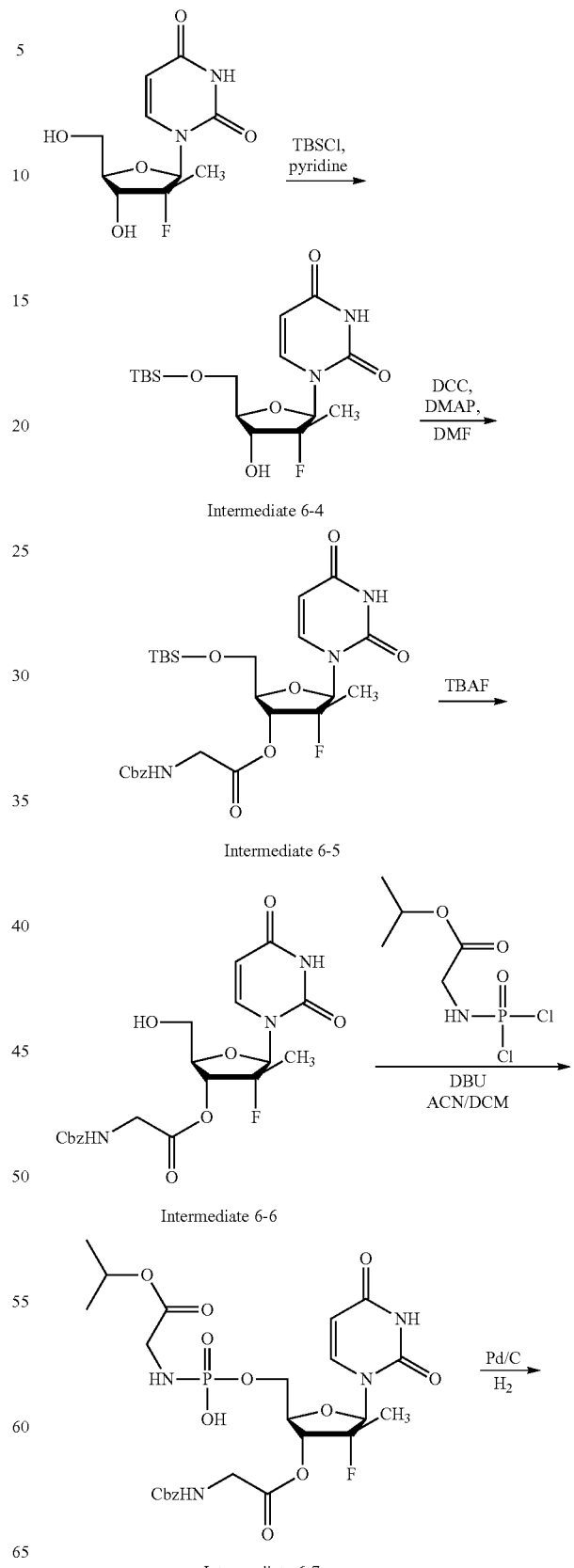

Intermediate 6-4

Intermediate 6-5

Intermediate 6-6

Intermediate 6-7

-continued

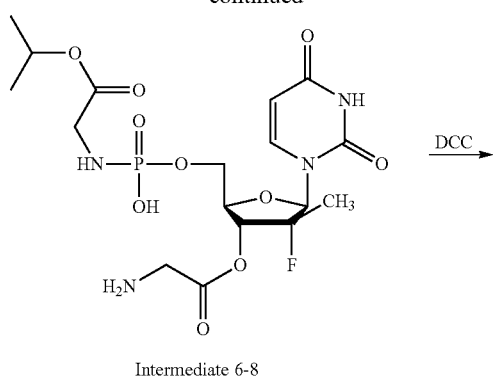

Intermediate 6-8

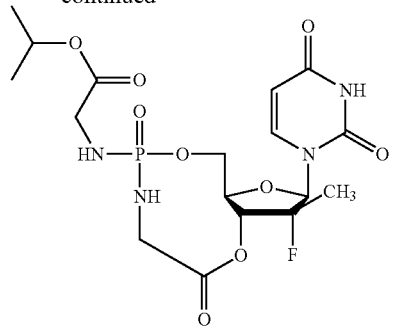

Compound 6

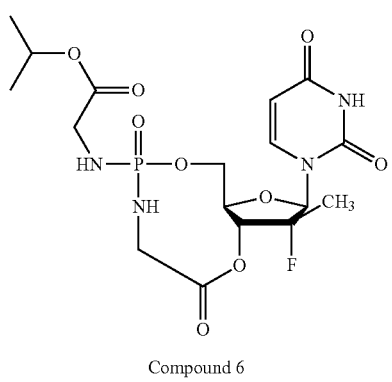

Compound 6

Scheme 6-C

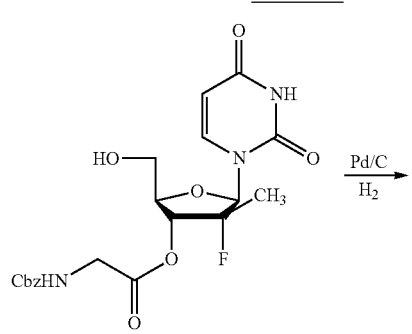

Intermediate 6-6

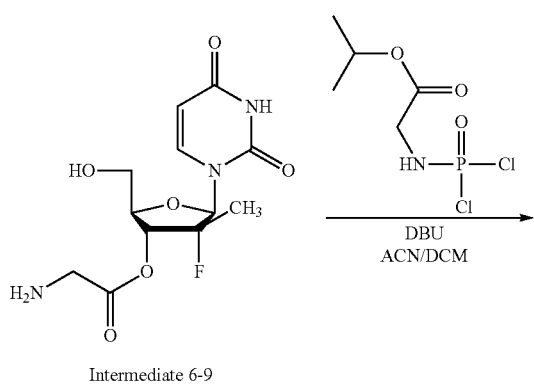

Intermediate 6-9

Example 7: Biological Assays

The assays to measure antiviral and anti-neoplastic activities of these compounds are described below.

A. Assay for Inhibition of HCV RNA Replication:

The compounds of the present invention (such as compound 1, 2, 5, and 6) are evaluated for their ability to affect the replication of Hepatitis C Virus RNA in cultured hepatoma (HuH-7) cells containing a subgenomic HCV Replicon. The details of the assays are described below (WO 2008/079206 and WO 2007/027248).

Protocol a (WO 2008/079206):

The assay is an in situ Ribonuclease protection, Scintillation Proximity based-plate assay (SPA). 10,000-40,000 cells are plated in 100-200 μL of media containing 0.8 mg/mL G418 in 96-well cytostar plates (Amersham). Compounds are added to cells at various concentrations up to 100 μM in 1% DMSO at time 0 to 18 h and then cultured for 24-96 h. Cells are fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells are washed, treated with RNAse, washed, heated to 65° C. and counted in a Top-Count Inhibition of replication is read as a decrease in counts per minute (cpm).

Human HuH-7 hepatoma cells, which are selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Protocol b (WO 2007/027248):

A human hepatoma cell line (Huh-7) containing replicating HCV subgenomic replicon with a luciferase reporter gene (luc-ubi-neo) is used to evaluate anti-HCV activity of the compounds. In this assay, level of luciferase signal correlates with the viral RNA replication directly. The HCV replicon-reporter cell line (NK/luc-ubi-neo) is cultured in DMEM medium supplemented with 10% fetal bovine serum and 0.5 mg/ml Geneticin (G418). Cells are maintained in a subconfluent state to ensure high levels of HCV replicon RNA synthesis.

To evaluate the antiviral activity of compounds, serial dilutions are prepared with concentrations ranging from 300 to 0.14 μM. Diluted compounds are transferred to a 96-well plate followed by the addition of replicon cells (6000 cells per well). Cells are incubated with the compounds for 48 h after which luciferase activity is measured. Reduction of luciferase signal reflects the decrease of HCV replicon RNA in the treated cells and is used to determine the $EC_{50}$ value (concentration which yielded a 50% reduction in luciferase activity).

B. The ability of the compounds of the present invention to inhibit HIV infectivity and HIV spread is measured in the following assays (WO 2008/079206).

a. HIV Infectivity Assay

Assays are performed with a variant of HeLa Magi cells expressing both CXCR4 and CCR5 selected for low background β-galactosidase (β-gal) expression. Cells are infected for 48 h, and β-gal production from the integrated LHV-1 LTR promoter is quantified with a chemiluminescent substrate (Galactolight Plus, Tropix, Bedford, Mass.) Inhibitors are titrated (in duplicate) in twofold serial dilutions starting at 100 µM; percent inhibition at each concentration is calculated in relation to the control infection.

b. Inhibition of HIV Spread

The ability of the compounds of the present invention to inhibit the spread of the human immunedeficiency virus (BQN) is measured by the method described in U.S. Pat. No. 5,413,999 (May 9, 1995), and J. P. Vacca, et al., Proc. Natl. Acad. Sci., 91: 4096-4100 (1994), which are incorporated by reference herein in their entirety.

C. The following assays are employed to measure the activity of the compounds of the present invention against other RNA-dependent RNA viruses:

a. Determination of In Vitro Antiviral Activity of the Compounds Against Rhinovirus (Cytopathic Effect Inhibition Assay):

Assay conditions are described in the article by Sidwell and Huffman, "Use of disposable microtissue culture plates for antiviral and interferon induction studies," Appl. Microbiol. 22: 797-801 (1971).

Viruses:

Rhinovirus type 2 (RV-2), strain HGP, is used with KB cells and media (0.1% $NaHCO_3$, no antibiotics) as stated in the Sidwell and Huffman reference. The virus, obtained from the ATCC, is from a throat swab of an adult male with a mild acute febrile upper respiratory illness.

Rhinovirus type 9 (RV-9), strain 211, and rhinovirus type 14 (RV-14), strain Tow, can be obtained from the American Type Culture Collection (ATCC) in Rockville, Md. RV-9 is from human throat washings and RV-14 is from a throat swab of a young adult with upper respiratory illness.

Both of these viruses are used with HeLa Ohio-1 cells which are human cervical epitheloid carcinoma cells. MEM (Eagle's minimum essential medium) with 5% Fetal Bovine serum (FBS) and 0.1% $NaHCO_3$ is used as the growth medium. Antiviral test medium for all three virus types is MEM with 5% FBS, 0.1% $NaHCO_3$, 50 µg gentamicin/mL, and 10 mM MgCl2- 2000 µg/mL is the highest concentration used to assay the compounds of the present invention. Virus is added to the assay plate approximately 5 min after the test compound. Proper controls are also run. Assay plates are incubated with humidified air and 5% $CO_2$ at 37° C. Cytotoxicity is monitored in the control cells microscopically for morphologic changes. Regression analysis of the virus CPE data and the toxicity control data gives the $ED_{50}$ (50% effective dose) and $CC_{50}$ (50% cytotoxic concentration). The selectivity index (SI) was calculated by the formula: $SI=CC_{50} \div ED_{50}$.

b. Determination of In Vitro Antiviral Activity of the Compounds Against Dengue, Banzi, and Yellow Fever (CPE Inhibition Assay)

Assay details are provided in the Sidwell and Huffman reference above.

Viruses:

Dengue virus type 2, New Guinea strain, can be obtained from the Center for Disease Control. Two lines of African green monkey kidney cells are used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, can be obtained from ATCC. Vero cells are used with both of these viruses and for assay.

Cells and Media:

MA-104 cells (BioWhittaker, Inc., Walkersville, Md.) and Vero cells (ATCC) are used in Medium 199 with 5% FBS and 0.1% $NaHCO_3$ and without antibiotics.

Assay medium for dengue, yellow fever, and Banzi viruses is MEM, 2% FBS, 0.18% $NaHCO_3$ and 50 µg gentamicin/mL.

Antiviral testing of the compounds of the present invention is performed according to the Sidwell and Huffman reference and similar to the above rhinovirus antiviral testing. Adequate cytopathic effect (CPE) readings are achieved after 5-6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, can be obtained from the Center for Disease Control. Vero cells are grown and used as described above. Test medium is MEM, 1% FBS, 0.1% $NaHCO_3$ and 50 µg gentamicin/mL.

Antiviral testing of the compounds of the present invention is performed following the methods of Sidwell and Huffman which are similar to those used to assay for rhinovirus activity. Adequate cytopathic effect (CPE) readings are achieved after 5-6 days.

d. Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method is used which is described in "Microtiter Assay for Interferon: Microspectrophotometric Quantitation of Cytopathic Effect," Appl. Environ. Microbiol. 31: 35-38 (1976). A Model EL309 microplate reader (Bio-Tek Instruments Inc.) is used to read the assay plate. ED50's and CD50's were calculated as above.

D. Anti-HBV Assay

Compounds of the present invention can be assayed for anti-HBV activity according to any assay known to those of skill in the art.

E. Cytotoxicity Assay:

Protocol a. Cell cultures are prepared in appropriate media at concentrations of approximately $1.5 \times 10^5$ cells/mL for suspension cultures in 3 day incubations and $5.0 \times 10^4$ cells/mL for adherent cultures in 3 day incubations. 99 µL of cell culture is transferred to wells of a 96-well tissue culture treated plate, and 1 µL of 100-times final concentration of the test compound in DMSO is added. The plates are incubated at 37° C. and 5% $CO_2$ for a specified period of time. After the incubation period, 20 µL of CellTiter 96 Aqueous One Solution Cell Proliferation Assay reagent (MTS) (Promega) is added to each well and the plates are incubated at 37° C. and 5% $CO_2$ for an additional period of time up to 3 h. The plates are agitated to mix well and absorbance at 490 nm is read using a plate reader. A standard curve of suspension culture cells is prepared with known cell numbers just prior to the addition of MTS reagent. Metabolically active cells reduce MTS to formazan. Formazan absorbs at 490 nm. The absorbance at 490 nm in the presence of compound is compared to absorbance in cells without any compound added (Cory, A. H. et al, "Use of an aqueous soluble tetrazolium/formazan assay for cell growth assays in culture," Cancer Commun. 3: 207 (1991)).

Protocol b (WO 2007/027248). A Huh-7 cell line carrying a luciferase reporter gene (driven by a HIV LTR promoter) stably integrated into the chromosome is used to analyze the cytotoxic effect of the selected compounds. This cell line (LTR-luc) is maintained in DMEM medium with 10% FBS. Reduction of luciferase activity in the treated cells correlated with the cytotoxic effect of the test compound and is used to calculate the $CC_{50}$ value (concentration that inhibited cell growth by 50%).

F: Anticancer Assay

Compounds synthesized as anti-cancer agents including compound 3 and 4 can each be tested in leukemic cell lines to assess their anticancer efficacy. The compounds can be tested using the MTS assay reagents from Promega (Cell-Titer96 Aqueous One solution proliferation assay). The compounds can be tested between 10 μM and 0.002 μM in four fold dilutions (WO 2006/100439).

Example 8: Assay for the Release of Active Metabolite in Liver Cells

Compounds can be assayed for accumulation in targeted cells of a subject according to any assay known to those of skill in the art. In certain embodiments, a liver cell of the subject can be used to assay for the liver accumulation of compound or a derivative thereof, e.g. a nucleoside, nucleoside phosphate or nucleoside triphosphate derivative thereof Example 9: Pharmaceutical Formulations As a specific embodiment of an oral composition of a compound of the present invention, 50 mg of the compound of Example 1-6 is formulated with sufficient finely divided lactose to provide a total amount of 580 to 590 mg to fill a size 0 hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth herein above may be applicable as a consequence of variations in the responsiveness of the human being treated for severity of the viral infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:
1. The compound of Formula I-1, its stereoisomers, isotope-enriched analogues, pharmaceutically acceptable salts, hydrates, solvates, or crystalline or polymorphic forms thereof, wherein the bc-ProTide is represented as in I-1:

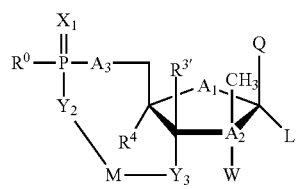

I-1

Q is any nucleic acid base or its analogues, either a naturally occurring or modified purine or pyrimidine base selected from the group consisting of:

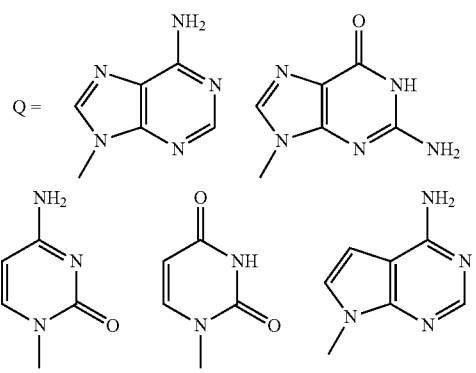

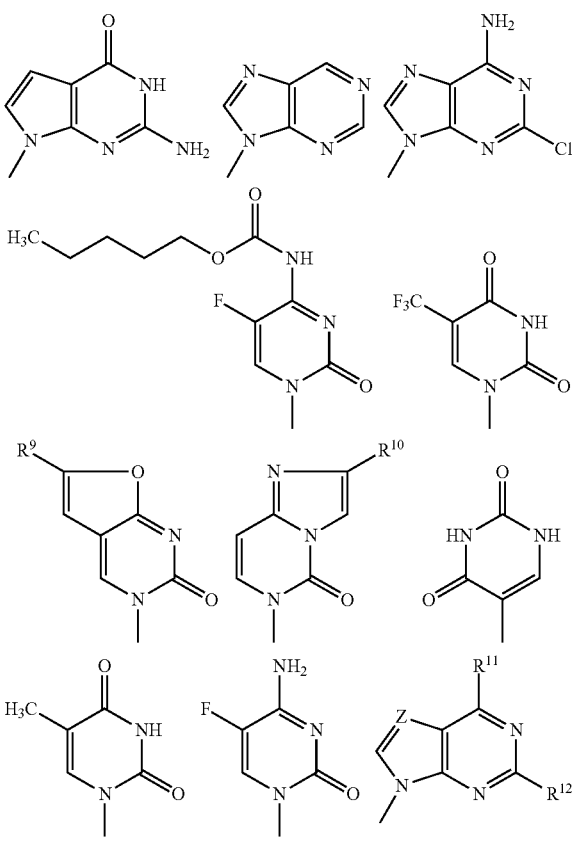

-continued

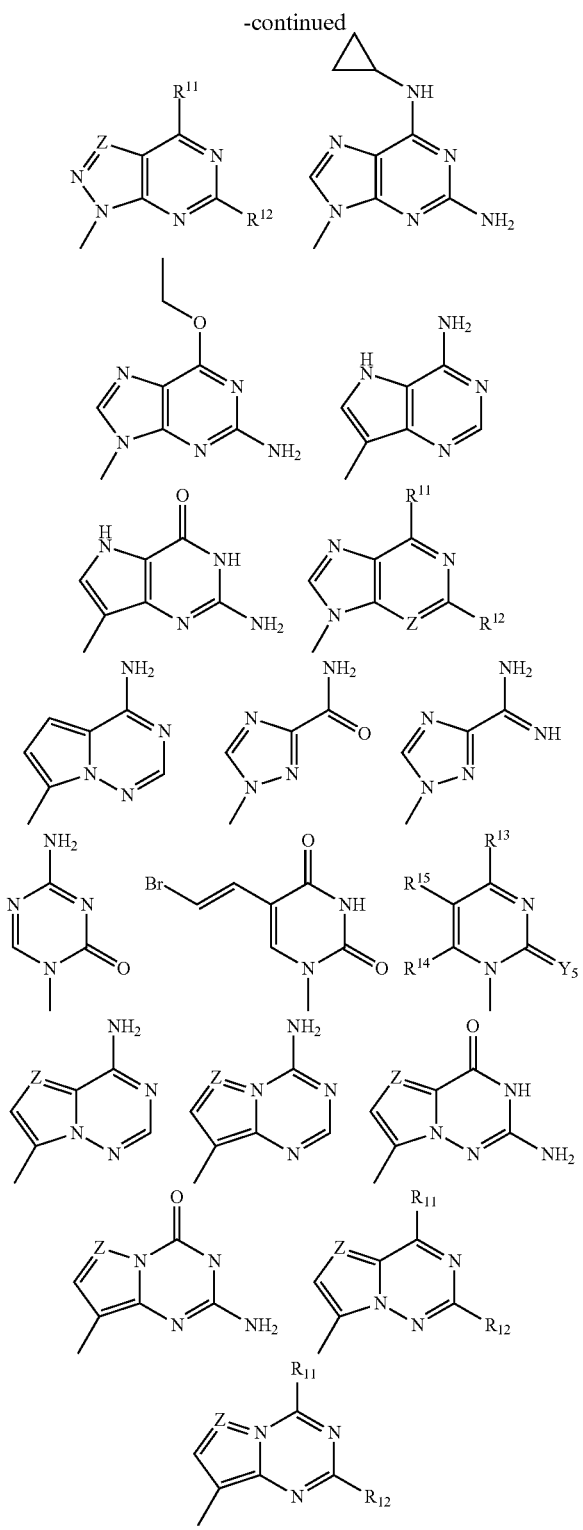

wherein:
(i) Z is N or $CR^{16}$; (ii) $R^9$, $R^{10}$, $R^{11}$, $R^{12}$, $R^{13}$, $R^{14}$ and $R^{15}$ are independently H, F, Cl, Br, I, OH, OR', SH, SR', SeH, SeR', $NH_2$, NHR', NHOH, NHOR', NHOR', NR'OR', NR'$_2$, $NHNH_2$, NR'$NH_2$, NR'NHR', NHNR'$_2$, NR'NR'$_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CN, $CO_2H$, $CO_2R'$, $CONH_2$, CONHR', CONR'$_2$, $CH=CHCO_2H$, or $CH=CHCO_2R'$, wherein R' is selected from the group consisting of H, an optionally substituted $C_1$-$C_{20}$ alkyl, an optionally substituted lower alkyl, an optionally substituted cycloalkyl, an optionally substituted alkynyl of $C_2$-$C_6$, an optionally substituted lower alkenyl of $C_2$-$C_6$, an optionally substituted aryl, an optionally substituted heteroaryl, an optionally substituted sulfonyl and optionally substituted acyl, and alternatively, in the instance of NR'$_2$, each R' comprise at least one C atom that are joined to form a heterocycle comprising at least two carbon atoms; (iii) $Y_5$ is selected from O, S, and Se; (iv) $R^{16}$ is H, halogen (including F, Cl, Br, I), OH, OR', SH, SR', $NH_2$, NHR', NR'$_2$, $NO_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CN, $CO_2H$, $CO_2R'$, $C(=O)NH_2$, $C(=O)NHR'$, $C(=O)NR'_2$, $CH=CHCO_2H$, or $CH=CHCO_2R'$, aryl, or heteroaryl;

$A_1$ is selected from O, S, Se, $NR^6$, $C=CH_2$, and $CR^{7a}R^{7b}$, where (i) $R^6$ is $R^{6'}$ or $C(=O)R^{6'}$ where $R^{6'}$ is H, alkyl, aryl, heteroaryl, OH, alkoxy, aryloxy, heteroaryloxy, alkylamino, arylamino, or heteroarylamino, and $R^{7a}$ and $R^{7b}$ are independently selected from H, OH, SH, F, Cl, CN, alkyl, aryl, and heteroaryl; (ii) $CR^{7a}R^{7b}$ is $C(CH_2)_m$ so as to form a spiro ring where m is 2 to 5, or is a substituted or unsubstituted spiro epoxide, aziridine, or oxetane; (iii) $R^4$ is $CH_2$ so as to form a substituted bicyclo[3.1.0]hexane including $A_1CR^4$;

$A_2R^3W$ is selected as follows:
(i) $A_2R^3W$ is $CH_2$, $CR^{7a}R^{7b}$, $C=CH_2$, or $C=CR^{7a}R^{7b}$ where $R^{7a}$ and $R^{7b}$ are independently selected from H, F, Cl, CN, alkyl, aryl, and heteroaryl; (ii) $A_2R^3W$ is $C(CH_2)_m$ where m is 2 to 5 so as to form a spiro ring or is a substituted or unsubstituted spiro epoxide, aziridine, or oxetane;
(iii) W is H, F, halogen, OH, OMe, CN, $NHR^6$ or $N_3$ where $A_2R^3$ is $CR^3$, and $R^6$ is $R^{6'}$ or $C(=O)R^{6'}$ where $R^{6'}$ is H, alkyl, aryl, heteroaryl, alkoxy, aryloxy, heteroaryloxy, alkylamino, arylamino, or heteroarylamino;
(iv) $R^3$ is H, $CH_3$, $CH_2F$, $CHF_2$, $CF_3$, F, halogen, OH, CN, $C_1$-$C_6$ alkyl, aryl or heteroaryl, where $A_2W$ is CW;
$R^{3'}$ is H, $CH_3$, $CH_2F$, $CHF_2$, $CF_3$, F, halogen, CN, $C_1$-$C_6$ alkyl, aryl, alkoxy carbonyl, or thioalkoxy carbonyl, $C_1$-$C_{10}$ alkylcarbamoyl ($C_1$-$C_{10}$ alkylaminocarbonyl), arylcarbamoyl, or heteroarylcarbamoyl;
$A_3$ is selected as follows:
(i) $A_3$ is O, S, Se, or $NR^6$ where $R^6$ is H, $OR^{6'}$, alkyl, aryl, $C(=O)R^{6'}$, or $CO_2R^{6'}$, where $R^{6'}$ is H, alkyl, aryl, or heteroaryl; (ii) $A_3CH_2$ can be optionally replaced with $CH_2A_3$, or $CF_2A_3$, so as to represent a phosphonate or phosphonamidate;
L and $R^4$ are independently selected from H, a lower alkyl, CN, vinyl, O-(lower alkyl), —$(CH_2)_pOH$, where p is 1 to 6, $CH_2F$, $N_3$, $CH_2CN$, $CH_2NH_2$, $CH_2NHCH_3$, $CH_2N(CH_3)_2$, optionally substituted alkynyl, or halogen, including F, Cl, Br, or I;
$PR^0$ is selected from:
(i) phosphate, or phosphoramidate represented by $PY_4R^2$ where $Y_4$ is O, S, Se, or $NR^{8'''}$; (ii) phosphoramidate of amino acid esters or amides, or of esters or amides of modified amino acids, represented by $PY_1[C(R^{1a}R^{1b})]_d C(=X_2)Y_4R^2$ where d=1 to 4, $Y_1$ is $NR^8$, $X_2$ is O, S or Se, and $Y_4$ is O, S, Se, or $NR^{8'''}$;

$X_1$ is O, S or Se;

M is a molecular bridge selected from $CR^{5a}R^{5b}$ and $(CR^{5a}R^{5b})OC(=O)$;

$Y_1, Y_2, Y_3$, and $Y_4$ are selected as follows:
(i) $Y_1$ is selected from O, S, Se, and $NR^8$; (ii) $Y_2$ is selected from O, S, Se, and $NR^{8'}$; (iii) $Y_3$ is selected from O, S, Se, and $NR^{8''}$; (iv) $Y_4$ is selected from O, S, Se, and $NR^{8'''}$; (v) $R^8$ and $R^{1a}$ or $R^{1b}$ together are $(CH_2)_n$ so as to form a cyclic ring that includes the adjoining N and C atoms, where n is 2 to 4, and $Y_1$ is $NR^8$; (vi) $R^{8'}$ and $R^{5a}$ or $R^{5b}$ together are $(CH_2)_n$ so as to form a cyclic ring that includes the adjoining N and C atoms, where n is 2 to 4 and $Y_2$ is $NR^{8'}$; (vii) $R^{8''}$ and $R^{5a}$ or $R^{5b}$ together are $(CH_2)_n$ so as to form a cyclic ring that includes the adjoining N and C atoms, where n is 2 to 4, and $Y_3$ is $NR^{8''}$;

$R^2$, $R^8$, $R^{8'}$, $R^{8''}$, and $R^{8'''}$ is independently hydrogen, $C_1-C_{10}$ alkyl, $C_1-C_{10}$ alkyl optionally substituted with a lower alkyl, alkoxyalkyl, di(lower alkyl)-aminoalkyl, $C_1-C_{10}$ haloalkyl, $C_3-C_{10}$ cycloalkyl, cycloalkyl alkyl, cycloheteroalkyl, phenyl, substituted phenyl, pyridyl, or substituted pyridyl; $R^8$, $R^{8'}$, $R^{8''}$, or $R^{8'''}$ in $Y_x$ can be the same or different groups where x is 1 to 4;

$R^{1a}$ and $R^{1b}$ are selected as follows:
(i) $R^{1a}$ and $R^{1b}$ are independently selected from hydrogen, $C_1-C_{10}$ alkyl, cycloalkyl, $-(CH_2)_cNR^{1'}{}_2$, hydroxy($C_1$-$C_6$)alkyl, $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl, heteroaryl, arylalkyl($C_1-C_3$), and heteroarylalkyl($C_1-C_3$), where c is 1 to 6, d is 0 to 2, e is 0 to 3, and said aryl groups are optionally substituted with a group selected from hydroxyl, $C_1-C_{10}$ alkyl, $C_1-C_6$ alkoxy, halogen, nitro and cyano, and where $R^{1'}$ is independently hydrogen or $C_1-C_{20}$ alkyl, and $R^{1'''}$ is $-OR^{1'}$ or $-N(R^{1'})_2$; (ii) $R^{1a}$ is H and $R^{1b}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; or (iii) $R^{1b}$ is H and $R^{1a}$ is H, $CH_3$, $CH_2CH_3$, $CH_2CH_2CH_3$, $CH(CH_3)_2$, $CH_2CH(CH_3)_2$, $CH(CH_3)CH_2CH_3$, $CH_2$-indol-3-yl, $-CH_2CH_2SCH_3$, $CH_2OH$, $CH(OH)CH_3$, $CH_2SH$, $CH_2CO_2H$, $CH_2C(=O)NH_2$, $CH_2CH_2COOH$, $CH_2CH_2C(=O)NH_2$, $CH_2CH_2CH_2CH_2NH_2$, $-CH_2CH_2CH_2NHC(=NH)NH_2$, $CH_2Ph$, $CH_2((4'-OH)-Ph)$, $CH_2$-imidazol-4-yl, or lower cycloalkyl; (iv) $R^{1a}$ and $R^{1b}$ both are $C_1-C_6$ alkyl; (v) $R^{1a}$ and $R^{1b}$ together are $(CH_2)_m$ so as to form a spiro ring, where m is 2 to 5; (vi) $R^{1a}$ is hydrogen and $R^{1b}$ and $R^8$ together are $(CH_2)_n$ so as to form a cyclic ring that includes the adjoining N and C atoms, where n is 2 to 4 and $Y_1$ is $NR^8$; (vii) $R^{1b}$ is hydrogen and $R^{1a}$ and $R^8$ together are $(CH_2)_n$ so as to form a cyclic ring that includes the adjoining N and C atoms, where n is 2 to 4 and $Y_1$ is $NR^8$;

$R^{5a}$ and $R^{5b}$ are selected as follows:
(i) $R^{5a}$, $R^{5b}$ are independently selected from hydrogen, $C_1-C_{10}$ alkyl, cycloalkyl, $-(CH_2)_c(NR^{1'})_2$, hydroxyalkyl ($C_1-C_6$), $-CH_2SH$, $-(CH_2)_2S(=O)_dMe$, $-(CH_2)_3NHC(=NH)NH_2$, (1H-indol-3-yl)methyl, (1H-imidazol-4-yl)methyl, $-(CH_2)_eCOR^{1'''}$, aryl, arylalkyl($C_1-C_3$), heteroaryl and heteroarylalkyl ($C_1-C_3$), where c is 1 to 6, d is 0 to 2, e is 0 to 3, and said aryl groups are optionally substituted with a group selected from hydroxyl, $C_1-C_{10}$ alkyl, $C_1-C_6$ alkoxy, halogen, nitro and cyano, and where $R^{1'}$ is independently hydrogen or $C_1-C_6$ alkyl and $R^{1'''}$ is $-OR^{1'}$ or $-N(R^{1'})_2$; (ii) $R^{5a}$ and $R^{5b}$ both are $C_1-C_6$ alkyl; (iii) $R^{5a}$ and $R^{5b}$ together are $(CH_2)_m$ so as to form a spiro ring, where m is 2 to 5; (iv) $R^{5a}$ is hydrogen and $R^{5b}$ and $R^{8'}$ together are $(CH_2)_n$ so as to form a cyclic ring that includes the adjoining N and C atoms where $Y_2$ is $NR^{8'}$, and n is 2 to 4; (v) $R^{5b}$ is hydrogen and $R^{5a}$ and $R^{8'}$ together are $(CH_2)_n$ so as to form a cyclic ring that includes the adjoining N and C atoms, where $Y_2$ is $NR^{8'}$, and n is 2 to 4; (vi) $R^{5a}$ is hydrogen and $R^{5b}$ and $R^{8''}$ together are $(CH_2)_n$ so as to form a cyclic ring that includes the adjoining N and C atoms where $Y_3$ is $NR^{8''}$, and n is 2 to 4; (vii) $R^{5b}$ is hydrogen and $R^{5a}$ and $R^{8''}$ together are $(CH_2)_n$ so as to form a cyclic ring that includes the adjoining N and C atoms, where $Y_3$ is $NR^{8''}$, and n is 2 to 4.

2. The compound of claim 1, its stereoisomers, isotope-enriched analogue, pharmaceutically acceptable salt, hydrate, solvate, or crystalline or polymorphic form thereof, wherein the bc-ProTide is represented by Formula II:

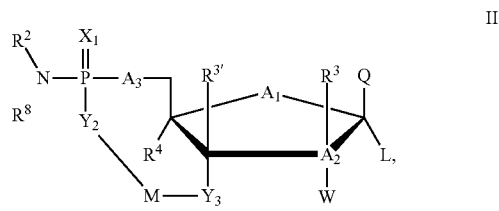

where in $Y_2$-M-$Y_3$ is selected from

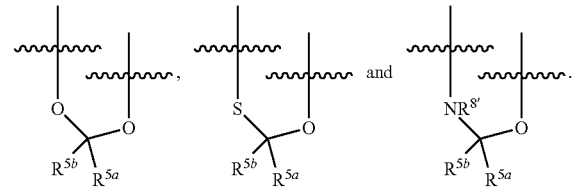

3. The compound of claim 1, its stereoisomers, isotope-enriched analogue, pharmaceutically acceptable salt, hydrate, solvate, or crystalline or polymorphic form thereof, wherein the bc-ProTide is represented by Formula III:

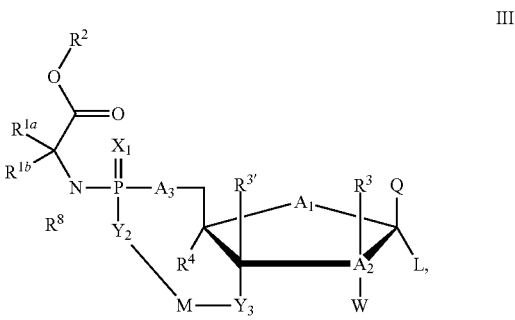

where in $Y_2$-M-$Y_3$ is selected from

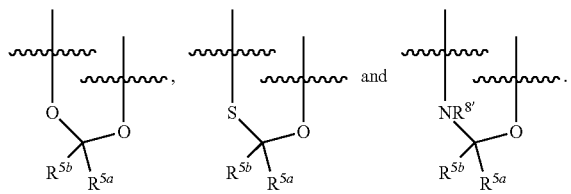

4. The compound of claim 1, its stereoisomers, isotope-enriched analogue, pharmaceutically acceptable salt, hydrate, solvate, or crystalline or polymorphic form thereof, wherein the bc-ProTide is represented by Formula III:

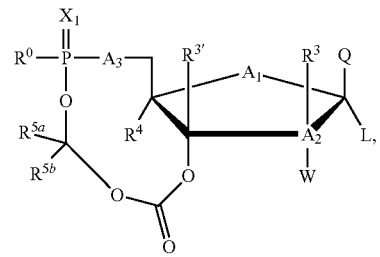

where $P(X_1)R^0$ is selected from:
(i) phosphate, or phosphoramidate represented by $PY_4R^2$ where $Y_4$ is O, S, Se, or $NR^{8'''}$, (ii) phosphoramidate of amino acid esters or amides, or of esters or amides of modified amino acids, represented by $PY_1[C(R^{1a}R^{1b})]_d C(=X_2)Y_4R^2$ where $Y_1$ is $NR^8$, d is 1 to 4, $X_2$ is O, S or Se, and $Y_4$ is O, S, Se, or $NR^{8'''}$.

5. A pharmaceutical composition comprising one or more of compounds in claim 1, optionally in combination with a pharmaceutically acceptable carrier, additive or excipient.

6. The pharmaceutical composition according to claim 1 further in combination with at least one additional antiviral agent.

\* \* \* \* \*

UNITED STATES PATENT AND TRADEMARK OFFICE
CERTIFICATE OF CORRECTION

PATENT NO. : 9,828,409 B2
APPLICATION NO. : 14/658194
DATED : November 28, 2017
INVENTOR(S) : Minghong Zhong It is certified that error appears in the above-identified patent and that said Letters Patent is hereby corrected as shown below:

In the Specification

Column 4, Line 48, "$NR^8$" should be changed to -- $NR^{8''}$ --.

Column 6, Line 11, "S, or $NR^{8'''}$" should be changed to -- S, $NR^{8'}$ or $NR^{8'''}$ --.

Column 8, Line 66, "alkylheteroaryl" should be changed to -- heteroarylalkyl --.

Column 14, Line 30, "$NR^8$" should be changed to -- $NR^{8''}$ --.

Column 14, Line 39, "$(=O)-Y-Y_3$" should be changed to -- $(=O)-Y_3$ --.

Column 16, Line 24, "$R^1$" should be changed to -- $R^{1'}$ --.

Column 17, Line 1, "$NR^8$" should be changed to -- $NR^{8''}$ --.

Column 22, Line 12, "$R^5$" should be changed to -- $R^{5a}$ --.

Column 23, Line 56, "$R^1$" should be changed to -- $R^{1'}$ --.

Column 29, Line 7, "$R^1$" should be changed to -- $R^{1'}$ --.

Column 33, Line 16, "$R^8$ and $R^{8'}$" should be changed to -- $R^{8'}$ and $R^{8'''}$ --.

Column 34, Line 43, "$R^8$ and $R^{8'}$" should be changed to -- $R^{8'}$ and $R^{8'''}$ --.

Column 35, Line 42, "$(COH_2)_m$" should be changed to -- $(CH_2)_m$ --.

Column 36, Line 27, "$(CH_2)_x NR''_2$" should be changed to -- $(CH_2)_c NR''_2$ --.

Signed and Sealed this
Tenth Day of July, 2018

Andrei Iancu
*Director of the United States Patent and Trademark Office*

Column 36, Line 34, "$R^1$" should be changed to -- $R^{1'}$ --.

Column 37, Line 46, "$R^1$" should be changed to -- $R^{1'}$ --.

Column 38, Line 58, "$R^1$" should be changed to -- $R^{1'}$ --.

Column 54, Line 12, ", or known" should be changed to -- known --.

Column 62, Line 39, "benzamide" should be changed to -- carbamic acid benzyl ester --.

Column 68, Line 12, "provided" should be changed to -- provides --.

Column 77, Line 52, "MgCl2- 2000" should be changed to -- $MgCl_2$- 2000 --.

In the Claims

Column 84, Line 25, the formula II reading

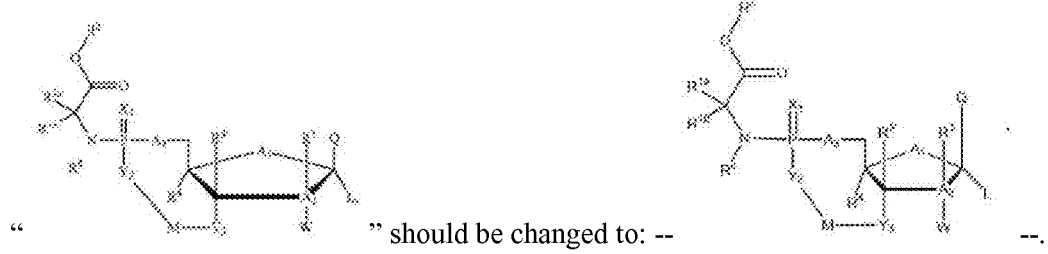

Column 84, Line 55, the formula III reading

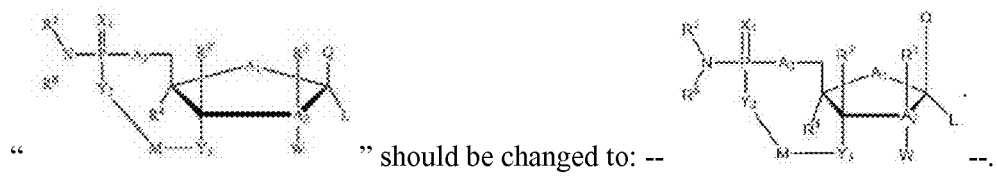

Column 85, Line 26, "Formula III" should be changed to -- Formula V --.

Column 86, Line 23, "claim 1" should be changed to -- claim 5 --.